US012781391B2

(12) United States Patent
Luo et al.

(10) Patent No.: US 12,781,391 B2
(45) Date of Patent: Nov. 3, 2026

(54) DYNAMIC HUMAN ANTIBODY LIGHT CHAIN LIBRARIES

(71) Applicant: Adagene Inc., Grand Cayman (KY)

(72) Inventors: Peter Peizhi Luo, Lansdale, PA (US); Yan Li, Suzhou (CN); Fangyong Du, Suzhou (CN)

(73) Assignee: Adagene Inc., Grand Cayman (KY)

(*) Notice: Subject to any disclaimer, the term of this patent is extended or adjusted under 35 U.S.C. 154(b) by 791 days.

(21) Appl. No.: 18/153,067

(22) Filed: Jan. 11, 2023

(65) Prior Publication Data

US 2023/0287597 A1 Sep. 14, 2023

Related U.S. Application Data

(62) Division of application No. 16/640,673, filed as application No. PCT/CN2017/098333 on Aug. 21, 2017, now Pat. No. 11,585,014.

(51) Int. Cl.
*C40B 40/08* (2006.01)
*C07K 16/00* (2006.01)

(52) U.S. Cl.
CPC ............ *C40B 40/08* (2013.01); *C07K 16/005* (2013.01); *C07K 2317/565* (2013.01)

(58) Field of Classification Search
None
See application file for complete search history.

(56) References Cited

U.S. PATENT DOCUMENTS 4,816,567 A 3/1989 Cabilly et al.
5,545,806 A 8/1996 Lonberg et al.
5,545,807 A 8/1996 Surani et al.
5,569,825 A 10/1996 Lonberg et al.
5,625,126 A 4/1997 Lonberg et al.
5,633,425 A 5/1997 Lonberg et al.
5,648,237 A 7/1997 Carter
5,661,016 A 8/1997 Lonberg et al.
5,731,168 A 3/1998 Carter et al.
5,789,199 A 8/1998 Joly et al.
(Continued)

FOREIGN PATENT DOCUMENTS

CN 103603057 A 2/2014
EP 440146 A2 8/1991
(Continued)

OTHER PUBLICATIONS

Better et al., (1989). "Expression of engineered antibodies and antibody fragments in microorganisms," Meth. Enzymol., 178:476-496.

(Continued)

*Primary Examiner* — Christian C Boesen
(74) *Attorney, Agent, or Firm* — Morrison & Foerster LLP

(57) ABSTRACT

Provided herein are libraries containing polynucleotides, where one of the polynucleotides encodes an antibody light chain with specific hypervariable regions HVR-L1, HVR-L2, and HVR-L3. Further provided herein are libraries containing polynucleotides encoding a plurality of unique antibodies, wherein each antibody comprises a heavy chain variable region and a light chain variable region. Also provided are antibodies, polypeptide libraries, vector libraries, cells, non-human animals, antibody light chains, methods of making an antibody library, kits, and methods of generating a bispecific antibody related thereto.

13 Claims, 3 Drawing Sheets

Specification includes a Sequence Listing.

(56) References Cited

U.S. PATENT DOCUMENTS

| | | | |
|---|---|---|---|
| 5,807,706 | A | 9/1998 | Carter et al. |
| 5,821,333 | A | 10/1998 | Carter et al. |
| 5,840,523 | A | 11/1998 | Simmons et al. |
| 5,959,177 | A | 9/1999 | Hein et al. |
| 6,040,498 | A | 3/2000 | Stomp et al. |
| 6,417,429 | B1 | 7/2002 | Hein et al. |
| 6,420,548 | B1 | 7/2002 | Vezina et al. |
| 7,125,978 | B1 | 10/2006 | Vezina et al. |
| 7,642,228 | B2 | 1/2010 | Carter et al. |
| 7,695,936 | B2 | 4/2010 | Carter et al. |
| 8,216,805 | B2 | 7/2012 | Carter et al. |
| 11,578,426 | B2 | 2/2023 | Luo et al. |
| 11,585,014 | B2 | 2/2023 | Luo et al. |
| 12,385,162 | B2 | 8/2025 | Luo et al. |
| 2003/0036092 | A1 | 2/2003 | Iverson et al. |
| 2003/0100023 | A1 | 5/2003 | Iverson et al. |
| 2004/0072740 | A1 | 4/2004 | Iverson et al. |
| 2005/0266000 | A1 | 12/2005 | Bond et al. |
| 2013/0089553 | A1 | 4/2013 | Carter et al. |
| 2014/0179547 | A1 | 6/2014 | Fischer et al. |
| 2016/0145604 | A1 | 5/2016 | Du et al. |
| 2020/0248336 | A1 | 8/2020 | Luo et al. |
| 2020/0362019 | A1 | 11/2020 | Luo et al. |
| 2024/0240358 | A1 | 7/2024 | Luo et al. |

FOREIGN PATENT DOCUMENTS

| | | | |
|---|---|---|---|
| EP | 1457559 | A1 | 9/2004 |
| JP | H4-211395 | A | 8/1992 |
| JP | 2013534130 | A | 9/2013 |
| JP | 2013539461 | A | 10/2013 |
| WO | WO-1991010741 | A1 | 7/1991 |
| WO | WO-1993008829 | A1 | 5/1993 |
| WO | WO-1996033735 | A1 | 10/1996 |
| WO | WO-1996034096 | A1 | 10/1996 |
| WO | WO-1998024893 | A2 | 6/1998 |
| WO | WO-2003044198 | A1 | 5/2003 |
| WO | WO-2006120230 | A2 | 11/2006 |
| WO | WO-2007056441 | A2 | 5/2007 |
| WO | WO-2009120922 | A2 | 10/2009 |
| WO | WO-2012009568 | A2 | 1/2012 |
| WO | WO-2012023053 | A2 | 2/2012 |
| WO | WO-2014139130 | A1 | 9/2014 |
| WO | WO-2016062989 | A1 | 4/2016 |
| WO | WO-2017049296 | A1 | 3/2017 |

OTHER PUBLICATIONS

Bruggemann et al., (1993). "Designer Mice: The Production of Human Antibody Repertoires in Transgenic Animals," Year in Immunol., 7:33-40.
Chen et al., (1999). "Selection and Analysis of an Optimized Anti-VEGF Antibody: Crystal Structure of an Affinity-matured Fab in Complex with Antigen", J. Mol. Biol., 293:865-881.
Chen et al., (2008). "Construction of a Large Phage-Displayed Human Antibody Domain Library with a Scaffold Based on a Newly Identified Highly Soluble, Stable Heavy Chain Variable Domain," J. Mol. Biol., 382:779-789.
Chen et al., (2009). "Construction of a human antibody domain (VH) library," Methods Mol Biol., 525:81-99.
Clackson et al., (1991). "Making antibody fragments using phage display libraries," Nature, 352:624-628.
Ericsson et al., (2006). "Thermofluor-based High-Throughput Stability Optimization of Proteins for Structural Studies," Analytical Biochemistry, 357: 289-298.
Extended European Search Report and Opinion for European Patent Application No. 17922355.7, mailed on Mar. 18, 2021, 8 pages.
Fellouse et al., (2004). "Synthetic Antibodies From a Four-Amino-Acid Code: A Dominant Role for Tyrosine in Antigen Recognition," Proc. Nat. Acad. Sci. USA, 101(34):12467-12472.
Fischer et al., (2015). "Exploiting light chains for the scalable generation and platform purification of native human bispecific IgG," Nat. Commun., 6(6113):1-12.
Fishwild et al., (1996). "High-avidity human IgGK monoclonal antibodies from a novel strain of minilocus transgenic mice," Nature Biotechnol., 14:845-851.
Gerngross, (2004). "Advances in the Production of Human Therapeutic Proteins in Yeasts and Filamentous Fungi," Nat. Biotech., 22:1409-1414.
Graham et al., (1977). "Characteristics of a Human Cell Line Transformed by DNA From Human Adenovirus Type 5," J. Gen Virol., 36:59-72.
Ho et al., (2006). "Isolation of anti-CD22 Fv with high affinity by Fv display on human cells," PNAS, 103:9637-9642.
Hongo et al., (1995). "Development and characterization of murine monoclonal antibodies to the latency-associated peptide of transforming growth factor beta 1," Hybridoma, 14(3):253-260.
International Search Report and Written Opinion for International Patent Application No. PCT/CN2017/098299, mailed on May 24, 2018, 10 pages.
International Search Report and Written Opinion for International Patent Application No. PCT/CN2017/098333, mailed on May 25, 2018, 10 pages.
Jakobovits et al., (1993). "Analysis of homozygous mutant chimeric mice: deletion of the immunoglobulin heavy-chain joining region blocks B-cell development and antibody production," Proc. Nat'l Acad. Sci. USA, 90:2551-2555.
Jakobovits et al., (1993). "Germ-line transmission and expression of a human-derived yeast artificial chromosome," Nature, 362:255-258.
James et al., (2003). "Conformational diversity and protein evolution—a 60-year-old hypothesis revisited," Trends Biochem Sci., 28(7):361-368.
Jeong et al., (2007). "APEx 2-hybrid, a quantitative protein-protein interaction assay for antibody discovery and engineering," PNAS, 104: 8247-8252.
Kohler et al., (1975). "Continuous Cultures of Fused Cells Secreting Antibody of Predefined Specificity," Nature, 256:495-497.
Lavinder et al., (2009). "High-Throughput Thermal Scanning: A General, Rapid Dye-Binding Thermal Shift Screen for Protein Engineering," J. Am. Chem. Soc., 131:3794-3795.
Lee et al., (2004). "Bivalent Antibody Phage Display Mimics Natural Immunoglobulin," J. Immunol. Methods, 284(1-2):119-132.
Lee et al., (2004). "High-affinity Human Antibodies From Phage-Displayed Synthetic Fab Libraries With a Single Framework Scaffold," J. Mol. Biol., 340(5):1073-1093.
Lei et al., (1987). "Characterization of the Erwinia Carotovora pelB Gene and Its Product Pectate Lyase," J. Bacteriol., 169:4379-4383.
Li et al., (2006). "Optimization of Humanized IgGs in Glycoengineered Pichia Pastoris," Nat. Biotech., 24:210-215.
Lonberg et al., (1994). "Antigen-specific human antibodies from mice comprising four distinct genetic modifications," Nature, 368:856-859.
Lonberg et al., (1995). "Human Antibodies From Transgenic Mice," Intern. Rev. Immunol., 13:65-93.
Marks et al., (1991). "By-passing Immunization. Human Antibodies From V-gene Libraries Displayed on Phage," J. MoL Biol., 222:581-597.
Marks et al., (1992). "By-Passing Immunization: Building High Affinity Human Antibodies by Chain Shuffling," Bio/Technology, 10:779-783.
Mather et al., (1982). "Culture of Testicular Cells in Hormone-Supplemented Serum-Free Medium," Annals N.Y. Acad. Sci., 383:44-68.
Mather, (1980). "Establishment and Characterization of Two Distinct Mouse Testicular Epithelial Cell Lines," Biol. Reprod., 23:243-251.
Mazor et al., (2007). "Isolation of Engineered, Full-Length Antibodies From Libraries Expressed in *Escherichia coli*," Nature Biotechnology, 25:563-565.
Millstein et al., (1983). "Hybrid Hybridomas and Their Use in Immunohistochemistry," Nature, 305:537-40.
Morrison, (1994). "Success in specification," Nature, 368:812-813.
Neuberger, (1996). "Generating high-avidity human Mabs in mice," Nature Biotechnol., 14:826.

(56) References Cited

OTHER PUBLICATIONS

Office Action received for Japanese Patent Application No. 2020-510116 mailed on Aug. 10, 2021, 10 pages.
Office Action received for Japanese Patent Application No. 2020-510115 mailed on Sep. 14, 2021, 14 pages.
Office Action received for Japanese Patent Application No. 2020-510116 mailed on Jan. 4, 2022, 4 pages.
Phillips et al., (2011). "The Combined Use of the Thermofluor Assay and ThermoQ Analytical Software for the Determination of Protein Stability and Buffer Optimization as an Aid in Protein Crystallization," Current Protocols in Mol. Biol., 94: 10.28.1-10.28.15.
Search Report and Written Opinion for Brazilian Patent Application No. 112020003622-6, completed in Aug. 3, 2021, 5 pages.
Sidhu et al., (2004). "Phage-displayed Antibody Libraries of Synthetic Heavy Chain Complementarity Determining Regions," J. Mol Biol., 338(2):299-310.
Skerra et al., (1991). "The Functional Expression of Antibody Fv Fragments in *Ischhuchia coli*: Improved Vectors and a Generally Applicable Purification Technique," Biotechnology, 9: 273-278.
Speiss et al., (2013). "Bispecific Antibodies With Natural Architecture Produced by Co-Culture of Bacteria Expressing Two Distinct Half-Antibodies," Nat Biotechnol., 31:753-758.
Traunecker et al., (1991). "Bispecific single chain molecules (Janusins) target cytotoxic lymphocytes on HIV infected cells.," EMBO J., 10:3655-3659.
Urlaub et al., (1980). "Isolation of Chinese hamster cell mutants deficient in dihydrofolate reductase activity," Proc. Natl. Acad. Sci. USA, 77:4216-4220.
Xu et al., (2000). "Diversity in the CDR3 Region of V(H) Is Sufficient for Most Antibody Specificities," Immunity, 13:37-45.
Yang et al., (2016). "Comparison of Biosensor Platforms in the Evaluation of High Affinity Antibody-Antigen Binding Kinetics," Anal. Biochem., 508:78-96.
Yazaki et al., (2004). "Expression of Recombinant Antibodies in Mammalian Cell Lines," Methods in Molecular Biology, 248:255-268.
Ama D. (2011). "Complementarity-determining region: CDR," Netsu Sokutei, 38(1):29. 3 pages.
Sharkey et al., (2017). "Purification of common light chain IgG-like bispecific antibodies using highly linear pH gradients," mAbs, 9(2):257-268.
Moreland, L.W. (eds) (2004). "Hypervariable region," Rheumatology and Immunology Therapy. Springer, Berlin, Heidelberg. 5 pages.
Hilyard et al. (1992). "Protein Engineering of Antibody Combining Sites", in Anthony R Rees, Michael J E Sternberg, and Ronald Wetzel (eds), Protein Engineering: A Practical Approach (Oxford, 1992; online edn, Oxford Academic, Oct. 31, 2023). 26 pages.
Chothia et al. (1989). "Conformations of immunoglobulin hypervariable regions," Nature 342(6252):877-83.
Notice of Reasons for Rejection for Japanese Patent Application No. 2021-183235, dated Mar. 31, 2026, 7 pages (translation).
Ama et al., (2011). "Complementarity-determining region: CDR," Netsu Sokutei, 38:29, 6 pages (machine translation).
Chothia et al., (1989). "Conformations of immunoglobulin hypervariable regions," Nature, 342:877-883.
Hilyard et al., (1992). "Ch 11: Protein Engineering of Antibody Combining Sites," Protein Engineering: A Practical Approach, Oxford University Press, pp. 253-275.
Moreland, (2004). "Hypervariable region," Rheumatology and Immunology Therapy. 4 pages.

```
VL     DIQLTQSPSSLSASVGDRVTITCRASQSVSSYLAWYQQKPGKAPKLLIYDASNLETGVPSRFSGSGSGTDFTLTISSLQPEDFATYYCQQSYSTSHTFGQGTKVEIKR
ADG    <---------FW1--------><--HVR_L1-><-----FW2-----><-HVR_L2><-----------FW3-----------><--HVR_L3-><---FW4--->
VL     DIQLTQSPSSLSASVGDRVTITCRASQSVSSYLAWYQQKPGKAPKLLIYDASNLETGVPSRFSGSGSGTDFTLTISSLQPEDFATYYCQQSYSTSHTFGQGTKVEIKR
Kabat  <---------FW1--------><---CDR1--><-----FW2-----><-CDR2><--------------FW3-------------><--CDR3-><---FW4--->
```

DYNAMIC HUMAN ANTIBODY LIGHT CHAIN LIBRARIES

CROSS REFERENCE TO RELATED APPLICATIONS

This application is a divisional application of U.S. application Ser. No. 16/640,673 issued as a U.S. Pat. No. 11,585,014 and, having an international filing date of Aug. 21, 2017, which is a national stage application under 35 U.S.C. § 371 of International Application No. PCT/CN2017/098333, filed internationally on Aug. 21, 2017, the contents of which are hereby incorporated by reference in their entireties.

REFERENCE TO AN ELECTRONIC SEQUENCE LISTING

The content of the electronic sequence listing (6954020001012SeqList.xml; Size: 87,137 bytes; and Date of Creation: Jan. 10, 2023) is herein incorporated by reference in its entirety.

FIELD OF THE INVENTION

The present disclosure relates to libraries containing polynucleotides that encode antibody light chains (e.g., light chains of a dynamic human antibody), as well as antibody light chains, antibodies, cells, animals, methods, and kits related thereto.

BACKGROUND OF THE INVENTION

Monoclonal antibodies have become extremely useful in a wide variety of fields, including biological research, medical diagnosis, and pharmaceutical products. The variability of potential binding specificities allows for antibodies with valuable specificity and potency. However, this variability makes it difficult and laborious to screen through a huge number of antibodies to identify one or more with the desired properties.

One method of identifying an antibody of interest is to screen through an antibody library, such as a library of cloned B cell sequences, a phage display library, a yeast display library, and so forth. These libraries allow one to screen through a large number of antibodies, representing a multitude of unique antibody sequences, to identify antibodies with specific properties of interest, e.g., binding to particular target, binding affinity, selectivity, and the like. However, current libraries have particular limitations. Libraries derived from a biological source, such as a human B cell repertoire, are limited to those antibody sequences that can be cloned from the source. Synthetic libraries may include non-naturally occurring sequences as compared to biologically derived libraries, but they too are limited by the amount of antibodies that can be synthesized in a particular timeframe. Further, extremely large libraries require more time-consuming and exhaustive screening approaches; otherwise, only a fraction of the library can practically be screened for an antibody of interest.

Therefore, a need exists for the development of dynamic antibody libraries containing a robust set of dynamic units with well-defined developable sequence profiles for designing and constructing dynamic antibodies that are potentially more relevant functionally. Such libraries would greatly improve not only the diversity of the antibody binding sites on antibodies within the library, but also the efficiency of screening for antibodies harboring novel and/or conformational epitopes on a given antigen. Moreover, such libraries would increase the likelihood with which a particular antibody of interest might be identified with a high affinity and developability profile.

All references cited herein, including patent applications, patent publications, and UniProtKB/Swiss-Prot Accession numbers are herein incorporated by reference in their entirety, as if each individual reference were specifically and individually indicated to be incorporated by reference.

SUMMARY OF THE INVENTION

To meet the above and other needs, disclosed herein are antibody sequences, such as light chain hypervariable regions (HVRs) and light chain variable regions (e.g., VL regions), that allow for dynamic human antibodies. These sequences were designed to allow for antibodies with highly flexible HVR sequence loops that are able to bind their targets with high potency and/or recognize multiple useful epitopes, and/or cross-react with epitopes shared among different species at low sequence identity (around 60% sequence identity or less). Advantageously, these antibody sequences allow the creation of much smaller libraries that nonetheless contain a multitude of useful antibodies, and/or a much larger diversity at a given library size. Such libraries can be used to identify new antibodies of interest that are specific for a wide range of targets or, in some cases, cross-reactive against multiple targets of interest.

Accordingly, in one aspect, provided herein are libraries comprising polynucleotides (e.g., synthetic polynucleotides), wherein one of the polynucleotides encodes an antibody light chain variable region comprising a HVR-L1, a HVR-L2 and a HVR-L3, and wherein at least two of the HVR-L1, HVR-L2, and HVR-L3 of the antibody light chain variable region comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23. In some embodiments, at least two, at least three, at least four, at least five, at least ten, at least 50, at least 100, at least 200, at least 250, or 280 of the polynucleotides encode a light chain variable region comprising a HVR-L1, a HVR-L2 and a HVR-L3, and wherein at least two of the HVR-L1, HVR-L2, and HVR-L3 of the antibody light chain variable region comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23. In some embodiments, each of the polynucleotides encode a light chain comprising a HVR-L1, a HVR-L2 and a HVR-L3, and wherein at least two of the HVR-L1, HVR-L2, and HVR-L3 comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23.

In some embodiments, the polynucleotides contain less than about 1000 unique combinations of HVR-L1, HVR-L2, and HVR-L3 sequences. In some embodiments, the polynucleotides contain about 280 or less unique combinations of HVR-L1, HVR-L2, and HVR-L3 sequences. In some embodiments, the light chain variable region comprises a HVR-L2 comprising an amino acid sequence selected from the group consisting of SEQ ID NOS:5-9 and a HVR-L3 of the antibody comprising an amino acid sequence selected from the group consisting of SEQ ID NOS:10-23. In some embodiments, the light chain variable region comprises a HVR-L1 comprising an amino acid sequence selected from the group consisting of SEQ ID NOS:1-4 and a HVR-L2 of the antibody comprises an amino acid sequence selected from the group consisting of SEQ ID NOS:5-9. In some embodiments, the light chain variable region comprises a HVR-L1 comprising an amino acid sequence selected from the group consisting of SEQ ID NOS:1-4 and a HVR-L3 of the antibody comprising an amino acid sequence selected from the group consisting of SEQ ID NOS:10-23. In some embodiments, the light chain variable region comprises a HVR-L1 comprising an amino acid sequence selected from the group consisting of SEQ ID NOS:1-4, a HVR-L2 comprising an amino acid sequence selected from the group consisting of SEQ ID NOS:5-9, and a HVR-L3 comprising an amino acid sequence selected from the group consisting of SEQ ID NOS:10-23. In some embodiments, at least one of the HVR-L1, HVR-L2, and HVR-L3 of the antibody light chain variable region adopts multiple conformations, as assayed by structural determination and/or computational modeling. In some embodiments, at least one of the polynucleotides encoding the antibody light chain variable region is in a vector. In some embodiments, the vector is an expression vector. In some embodiments, the vector is a display vector. In some embodiments, at least one of the polynucleotides encoding the antibody light chain variable region is in a cell. In some embodiments, the cell is a bacterial, yeast, or mammalian cell (e.g., non-human animal cells or isolated human cells).

In some embodiments, the light chain variable region comprises three of a HVR-L1, a HVR-L2, and a HVR-L3 selected from the group consisting of: (1) a HVR-L1 comprising the amino acid sequence of SEQ ID NO:1, a HVR-L2 comprising the amino acid sequence of SEQ ID NO:9, and a HVR-L3 comprising an amino acid sequence selected from the group consisting of SEQ ID NOS:10-23; (2) a HVR-L1 comprising the amino acid sequence of SEQ ID NO:4, a HVR-L2 comprising the amino acid sequence of SEQ ID NO:9, and a HVR-L3 comprising an amino acid sequence selected from the group consisting of SEQ ID NOS:10-23; (3) a HVR-L1 comprising the amino acid sequence of SEQ ID NO:2, a HVR-L2 comprising the amino acid sequence of SEQ ID NO:9, and a HVR-L3 comprising an amino acid sequence selected from the group consisting of SEQ ID NOS:10-23; (4) a HVR-L1 comprising the amino acid sequence of SEQ ID NO:2, a HVR-L2 comprising an amino acid sequence selected from the group consisting of SEQ ID NOS:5-9, and a HVR-L3 comprising the amino acid sequence of SEQ ID NO:18; (5) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:23; (6) a HVR-L1 comprising the amino acid sequence of SEQ ID NO:1, a HVR-L2 sequence selected form the group consisting of SEQ ID NOS:5-9, and a HVR-L3 comprising the amino acid sequence of SEQ ID NO:20; (7) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:18; (8) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:23; (9) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:20; (10) a HVR-L1 comprising the amino acid sequence of SEQ ID NO:3, a HVR-L2 comprising the amino acid sequence of SEQ ID NO:9, and a HVR-L3 comprising an amino acid sequence selected from the group consisting of SEQ ID NOS:10-23; (11) a HVR-L1 comprising the amino acid sequence of SEQ ID NO:4, a HVR-L2 comprising the amino acid sequence of SEQ ID NO:6, and a HVR-L3 comprising an amino acid sequence selected from the group consisting of SEQ ID NOS:10-23; (12) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:23; (13) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:14; (14) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:18; (15) a HVR-L1 comprising the amino acid sequence of SEQ ID NO:3, a HVR-L2 comprising an amino acid sequence selected from the group consisting of SEQ ID NOS:5-9, and a HVR-L3 comprising the amino acid sequence of SEQ ID NO:20; (16) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:14; (17) a HVR-L1 comprising an amino acid sequence selected from the group consisting of SEQ ID NOS:1-4, a HVR-L2 comprising the amino acid sequence of SEQ ID NO:6, and a HVR-L3 comprising the amino acid sequence of SEQ ID NO:23; and (18) a HVR-L1 comprising an amino acid sequence selected from the group consisting of SEQ ID NOS:1-4, a HVR-L2 comprising the amino acid sequence of SEQ ID NO:7, and a HVR-L3 comprising the amino acid sequence of SEQ ID NO:23. In some embodiments, the light chain variable region comprises three of a HVR-L1, a HVR-L2, and a HVR-L3 selected from the group consisting of: (1) a HVR-L1 comprising the amino acid sequence of SEQ ID NO:2, a HVR-L2 comprising the amino acid sequence of SEQ ID NO:9, and a HVR-L3 comprising the amino acid sequence of SEQ ID NO:18; (2) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:23; (3) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:20; (4) a HVR-L1 comprising the amino acid sequence of SEQ ID NO:4, a HVR-L2 comprising the amino acid sequence of SEQ ID NO:9, and a HVR-L3 comprising the amino acid sequence of SEQ ID NO:14; (5) a HVR-L1 comprising the amino acid sequence of SEQ ID NO:3, a HVR-L2 comprising the amino acid sequence of SEQ ID NO:9, and a HVR-L3 comprising the amino acid sequence of SEQ ID NO:20; (6) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:18; (7) a HVR-L1 comprising the amino acid sequence of SEQ ID NO:4, a HVR-L2 comprising the amino acid sequence of SEQ ID NO:7, and a HVR-L3 comprising the amino acid sequence of SEQ ID NO:23; (8) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:23; (9) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:17; (10) a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:20; and (11) a HVR-L1 comprising the amino acid sequence of SEQ ID NO:4, a HVR-L2 comprising the amino acid sequence of SEQ ID NO:8, and a HVR-L3 comprising the amino acid sequence of SEQ ID NO: 11. In some embodiments, the light chain variable region comprises a HVR-L1, a HVR-L2, and a HVR-L3 of an antibody listed in Table 2.

In some embodiments, the light chain variable region comprises a FW-L1 comprising the amino acid sequence of SEQ ID NO:24, a FW-L2 comprising the amino acid sequence of SEQ ID NO:25, a FW-L3 comprising the amino acid sequence of SEQ ID NO:26, and a FW-L4 comprising the amino acid sequence of SEQ ID NO:27. In some embodiments, the light chain variable region comprises a sequence selected from the group consisting of SEQ ID NOS:28-50. In some embodiments, the polynucleotides encode full-length antibody light chains. In some embodiments, the libraries further comprise polynucleotides that encode antibody heavy chain variable regions. In some embodiments, the polynucleotides that encode antibody heavy chain variable regions include at least one unique sequence, at least 100 unique sequences, at least 1000 unique sequences, or least about $10^9$ unique sequences.

In another aspect, provided herein are libraries comprising polynucleotides (e.g., synthetic polynucleotides) encoding a plurality of unique antibodies, wherein each antibody comprises a heavy chain variable region and a light chain variable region, wherein the light chain variable region of each antibody of the plurality comprises an identical sequence and comprises a HVR-L1, a HVR-L2 and a HVR-L3, and wherein at least two of the HVR-L1, HVR-L2, and HVR-L3 comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23. In some embodiments, the light chain variable region comprises a HVR-L2 comprising an amino acid sequence selected from the group consisting of SEQ ID NO:5-9 and a HVR-L3 comprising an amino acid sequence selected from the group consisting of SEQ ID NO:10-23. In some embodiments, the light chain variable region comprises a HVR-L1 comprising an amino acid sequence selected from the group consisting of SEQ ID NO:1-4 and a HVR-L2 of the antibody comprises an amino acid sequence selected from the group consisting of SEQ ID NO:5-9. In some embodiments, the light chain variable region comprises a HVR-L1 comprising an amino acid sequence selected from the group consisting of SEQ ID NO:1-4 and a HVR-L3 of the antibody comprising an amino acid sequence selected from the group consisting of SEQ ID NO:10-23. In some embodiments, the light chain variable region comprises a HVR-L1 comprising an amino acid sequence selected from the group consisting of SEQ ID NO:1-4, a HVR-L2 comprising an amino acid sequence selected from the group consisting of SEQ ID NO:5-9, and a HVR-L3 comprising an amino acid sequence selected from the group consisting of SEQ ID NO:10-23. In some embodiments, the light chain variable region comprises three of a HVR-L1, a HVR-L2, and a HVR-L3 selected from the group consisting of: (1) a HVR-L1 comprising the amino acid sequence of SEQ ID NO:1, a HVR-L2 comprising the amino acid sequence of SEQ ID NO:9, and a HVR-L3 comprising an amino acid sequence selected from the group consisting of SEQ ID NOS:10-23; (2) a HVR-L1 comprising the amino acid sequence of SEQ ID NO:4, a HVR-L2 comprising the amino acid sequence of SEQ ID NO:9, and a HVR-L3 comprising an amino acid sequence selected from the group consisting of SEQ ID NOS:10-23; (3) a HVR-L1 comprising the amino acid sequence of SEQ ID NO:2, a HVR-L2 comprising the amino acid sequence of SEQ ID NO:9, and a HVR-L3 comprising an amino acid sequence selected from the group consisting of SEQ ID NOS:10-23; (4) a HVR-L1 comprising the amino acid sequence of SEQ ID NO:2, a HVR-L2 comprising an amino acid sequence selected from the group consisting of SEQ ID NOS:5-9, and a HVR-L3 comprising the amino acid sequence of SEQ ID NO:18; (5) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:23; (6) a HVR-L1 comprising the amino acid sequence of SEQ ID NO:1, a HVR-L2 sequence selected form the group consisting of SEQ ID NOS:5-9, and a HVR-L3 comprising the amino acid sequence of SEQ ID NO:20; (7) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:18; (8) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:23; (9) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:20; (10) a HVR-L1 comprising the amino acid sequence of SEQ ID NO:3, a HVR-L2 comprising the amino acid sequence of SEQ ID NO:9, and a HVR-L3 comprising an amino acid sequence selected from the group consisting of SEQ ID NOS:10-23; (11) a HVR-L1 comprising the amino acid sequence of SEQ ID NO:4, a HVR-L2 comprising the amino acid sequence of SEQ ID NO:6, and a HVR-L3 comprising an amino acid sequence selected from the group consisting of SEQ ID NOS:10-23; (12) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:23; (13) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:14; (14) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:18; (15) a HVR-L1 comprising the amino acid sequence of SEQ ID NO:3, a HVR-L2 comprising an amino acid sequence selected from the group consisting of SEQ ID NOS:5-9, and a HVR-L3 comprising the amino acid sequence of SEQ ID NO:20; (16) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:14; (17) a HVR-L1 comprising an amino acid sequence selected from the group consisting of SEQ ID NOS:1-4, a HVR-L2 comprising the amino acid sequence of SEQ ID NO:6, and a HVR-L3 comprising the amino acid sequence of SEQ ID NO:23; and (18) a HVR-L1 comprising an amino acid sequence selected from the group consisting of SEQ ID NOS:1-4, a HVR-L2 comprising the amino acid sequence of SEQ ID NO:7, and a HVR-L3 comprising the amino acid sequence of SEQ ID NO:23. In some embodiments, the light chain variable region comprises three of a HVR-L1, a HVR-L2, and a HVR-L3 selected from the group consisting of: (1) a HVR-L1 comprising the amino acid sequence of SEQ ID NO:2, a HVR-L2 comprising the amino acid sequence of SEQ ID NO:9, and a HVR-L3 comprising the amino acid sequence of SEQ ID NO:18; (2) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:23; (3) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:20; (4) a HVR-L1 comprising the amino acid sequence of SEQ ID NO:4, a HVR-L2 comprising the amino acid sequence of SEQ ID NO:9, and a HVR-L3 comprising the amino acid sequence of SEQ ID NO:14; (5) a HVR-L1 comprising the amino acid sequence of SEQ ID NO:3, a HVR-L2 comprising the amino acid sequence of SEQ ID NO:9, and a HVR-L3 comprising the amino acid sequence of SEQ ID NO:20; (6) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:18; (7) a HVR-L1 comprising the amino acid sequence of SEQ ID NO:4, a HVR-L2 comprising the amino acid sequence of SEQ ID NO:7, and a HVR-L3 comprising the amino acid sequence of SEQ ID NO:23; (8) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:23; (9) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:17; (10) a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:20; and (11) a HVR-L1 comprising the amino acid sequence of SEQ ID NO:4, a HVR-L2 comprising the amino acid sequence of SEQ ID NO:8, and a HVR-L3 comprising the amino acid sequence of SEQ ID NO: 11. In some embodiments, the light chain variable region comprises a HVR-L1, a HVR-L2, and a HVR-L3 of an antibody listed in Table 2.

In some embodiments, the light chain variable region comprises a FW-L1 comprising the amino acid sequence of SEQ ID NO:24, a FW-L2 comprising the amino acid sequence of SEQ ID NO:25, a FW-L3 comprising the amino acid sequence of SEQ ID NO:26, and a FW-L4 comprising the amino acid sequence of SEQ ID NO:27. In some embodiments, the light chain variable region comprises a sequence selected from the group consisting of SEQ ID NOS:28-50. In some embodiments, the heavy chain variable regions of the antibodies in the library have at least one unique sequence, at least 100 unique sequences, at least 1000 unique sequences, or at least about $10^9$ unique sequences. In some embodiments, the polynucleotides of the library are synthetic polynucleotides.

In another aspect, provided herein are antibodies comprising a polypeptide expressed by a polynucleotide (e.g., a synthetic polynucleotide) from the library according to any of the preceding embodiments. In some embodiments, the antibody binds at least 1 target with an equilibrium dissociation constant (Kd) of between about $10^{-7}$ and about $10^{-11}$ M.

In another aspect, provided herein are libraries comprising polypeptides in which at least one (e.g., at least one, at least two, at least five, at least 10, at least 25, at least 50, at least 75, at least 100, at least 125, at least 150, at least 175, at least 200, at least 225, at least 250, at least 275, etc.) of the polypeptides is encoded by encoded by a polynucleotide of the polynucleotide (e.g., synthetic polynucleotide) library according to any of the preceding embodiments. In some embodiments, at least two of the polypeptides are encoded by a polynucleotide of the polynucleotide library. In some embodiments, at least 100 of the polypeptides are encoded by a polynucleotide of the polynucleotide library. In some embodiments, each of the polypeptides is encoded by a polynucleotide of the polynucleotide library. In some embodiments, the at least one polypeptide is a light chain variable domain. In some embodiments, the at least one polypeptide is displayed on the surface of a phage. In some embodiments, the library comprising polypeptides further comprises at least one heavy chain variable domain polypeptide.

In another aspect, provided herein are libraries comprising vectors in which at least one (e.g., at least one, at least two, at least five, at least 10, at least 25, at least 50, at least 75, at least 100, at least 125, at least 150, at least 175, at least 200, at least 225, at least 250, at least 275, etc.) of the vectors comprises a polynucleotide of the polynucleotide library according to any of the preceding embodiments. In some embodiments, at least two of the vectors comprise a polynucleotide from the polynucleotide library. In some embodiments, at least 100 of the vectors comprise a polynucleotide from the polynucleotide library. In some embodiments, each of the vectors comprises a polynucleotide from the polynucleotide library. In some embodiments, the at least one vector encodes a light chain variable domain polypeptide. In some embodiments, the library comprising vectors further comprises a vector that encodes a heavy chain variable domain polypeptide. Also provided herein are libraries comprising populations of cells in which at least one (e.g., at least one, at least two, at least five, at least 10, at least 100, at least $10^3$, at least $10^4$, at least $10^5$, at least $10^6$, at least $10^7$, at least $10^8$, at least $10^9$, etc.) cell comprises a vector of the library according to any of the preceding embodiments. In some embodiments, at least two of the cells comprise a vector of the library. In some embodiments, at least 100 of the cells comprise a vector of the library. In some embodiments, each of the cells comprises a vector of the library. In some embodiments, the at least one cell is a bacterial, yeast, or mammalian cell (e.g., non-human animal cells or isolated human cells).

In another aspect, provided herein are phages comprising at least one polypeptide displayed on its surface, wherein the at least one polypeptide comprises an antigen binding domain that comprises an antibody light chain variable region comprising a HVR-L1, a HVR-L2 and a HVR-L3, and wherein at least two of the HVR-L1, HVR-L2, and HVR-L3 of the antibody light chain variable region comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23. In some embodiments, the antigen binding domain further comprises an antibody heavy chain variable region.

In another aspect, provided herein are non-human animals comprising the polynucleotide library according to any of the preceding embodiments. In some embodiments, the non-human animals are mammals (e.g., a mouse, rat, rabbit, camel, or non-human primate). In some embodiments, the non-human animal comprises polynucleotides, wherein one of the polynucleotides encodes an antibody light chain variable region comprising a HVR-L1, a HVR-L2 and a HVR-L3, and wherein at least two of the HVR-L1, HVR-L2, and HVR-L3 of the antibody light chain variable region comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23.

In another aspect, provided herein are antibody light chains comprising a light chain variable region comprising a HVR-L1, a HVR-L2 and a HVR-L3, and wherein at least two of the HVR-L1, HVR-L2, and HVR-L3 comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23. In some embodiments, the light chain variable region comprises a HVR-L2 comprising an amino acid sequence selected from the group consisting of SEQ ID NO:5-9 and a HVR-L3 of the antibody comprising an amino acid sequence selected from the group consisting of SEQ ID NO:10-23. In some embodiments, the light chain variable region comprises a HVR-L1 comprising an amino acid sequence selected from the group consisting of SEQ ID NO:1-4 and a HVR-L2 of the antibody comprises an amino acid sequence selected from the group consisting of SEQ ID NO:5-9. In some embodiments, the light chain variable region comprises a HVR-L1 comprising an amino acid sequence selected from the group consisting of SEQ ID NO:1-4 and a HVR-L3 of the antibody comprising an amino acid sequence selected from the group consisting of SEQ ID NO:10-23. In some embodiments, the light chain variable region comprises a HVR-L1 comprising an amino acid sequence selected from the group consisting of SEQ ID NO:1-4, a HVR-L2 comprising an amino acid sequence selected from the group consisting of SEQ ID NO:5-9, and a HVR-L3 comprising an amino acid sequence selected from the group consisting of SEQ ID NO:10-23. In some embodiments, the light chain variable region comprises three of a HVR-L1, a HVR-L2, and a HVR-L3 selected from the group consisting of: (1) a HVR-L1 comprising the amino acid sequence of SEQ ID NO:1, a HVR-L2 comprising the amino acid sequence of SEQ ID NO:9, and a HVR-L3 selected from the group consisting of SEQ ID NOS:10-23; (2) a HVR-L1 comprising the amino acid sequence of SEQ ID NO:4, a HVR-L2 comprising the amino acid sequence of SEQ ID NO:9, and a HVR-L3 comprising an amino acid sequence selected from the group consisting of SEQ ID NOS:10-23; (3) a HVR-L1 comprising the amino acid sequence of SEQ ID NO:2, a HVR-L2 comprising the amino acid sequence of SEQ ID NO:9, and a HVR-L3 comprising an amino acid sequence selected from the group consisting of SEQ ID NOS:10-23; (4) a HVR-L1 comprising the amino acid sequence of SEQ ID NO:2, a HVR-L2 comprising an amino acid sequence selected from the group consisting of SEQ ID NOS:5-9, and a HVR-L3 comprising the amino acid sequence of SEQ ID NO:18; (5) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:23; (6) a HVR-L1 comprising the amino acid sequence of SEQ ID NO:1, a HVR-L2 sequence selected form the group consisting of SEQ ID NOS:5-9, and a HVR-L3 comprising the amino acid sequence of SEQ ID NO:20; (7) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:18; (8) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:23; (9) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:20; (10) a HVR-L1 comprising the amino acid sequence of SEQ ID NO:3, a HVR-L2 comprising the amino acid sequence of SEQ ID NO:9, and a HVR-L3 comprising an amino acid sequence selected from the group consisting of SEQ ID NOS:10-23; (11) a HVR-L1 comprising the amino acid sequence of SEQ ID NO:4, a HVR-L2 comprising the amino acid sequence of SEQ ID NO:6, and a HVR-L3 comprising an amino acid sequence selected from the group consisting of SEQ ID NOS:10-23; (12) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:23; (13) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:14; (14) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:18; (15) a HVR-L1 comprising the amino acid sequence of SEQ ID NO:3, a HVR-L2 comprising an amino acid sequence selected from the group consisting of SEQ ID NOS:5-9, and a HVR-L3 comprising the amino acid sequence of SEQ ID NO:20; (16) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:14; (17) a HVR-L1 comprising an amino acid sequence selected from the group consisting of SEQ ID NOS:1-4, a HVR-L2 comprising the amino acid sequence of SEQ ID NO:6, and a HVR-L3 comprising the amino acid sequence of SEQ ID NO:23; and (18) a HVR-L1 comprising an amino acid sequence selected from the group consisting of SEQ ID NOS:1-4, a HVR-L2 comprising the amino acid sequence of SEQ ID NO:7, and a HVR-L3 comprising the amino acid sequence of SEQ ID NO:23. In some embodiments, the light chain variable region comprises three of a HVR-L1, a HVR-L2, and a HVR-L3 selected from the group consisting of: (1) a HVR- L1 comprising the amino acid sequence of SEQ ID NO:2, a HVR-L2 comprising the amino acid sequence of SEQ ID NO:9, and a HVR-L3 comprising the amino acid sequence of SEQ ID NO:18; (2) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:23; (3) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:20; (4) a HVR-L1 comprising the amino acid sequence of SEQ ID NO:4, a HVR-L2 comprising the amino acid sequence of SEQ ID NO:9, and a HVR-L3 comprising the amino acid sequence of SEQ ID NO:14; (5) a HVR-L1 comprising the amino acid sequence of SEQ ID NO:3, a HVR-L2 comprising the amino acid sequence of SEQ ID NO:9, and a HVR-L3 comprising the amino acid sequence of SEQ ID NO:20; (6) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:18; (7) a HVR-L1 comprising the amino acid sequence of SEQ ID NO:4, a HVR-L2 comprising the amino acid sequence of SEQ ID NO:7, and a HVR-L3 comprising the amino acid sequence of SEQ ID NO:23; (8) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:23; (9) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:17; (10) a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:20; and (11) a HVR-L1 comprising the amino acid sequence of SEQ ID NO:4, a HVR-L2 comprising the amino acid sequence of SEQ ID NO:8, and a HVR-L3 comprising the amino acid sequence of SEQ ID NO:11. In some embodiments, the light chain variable region comprises a HVR-L1, a HVR-L2, and a HVR-L3 of an antibody listed in Table 2. In some embodiments, the light chain variable region comprises a FW-L1 comprising the amino acid sequence of SEQ ID NO:24, a FW-L2 comprising the amino acid sequence of SEQ ID NO:25, a FW-L3 comprising the amino acid sequence of SEQ ID NO:26, and a FW-L4 comprising the amino acid sequence of SEQ ID NO:27. In some embodiments, the light chain variable region comprises a sequence selected from the group consisting of SEQ ID NOS:28-50. In some embodiments, at least one of the HVR-L1, HVR-L2, and HVR-L3 of the light chain variable region adopts multiple conformations, as assayed by structural determination and/or computational modeling.

In another aspect, provided herein are antibodies comprising a heavy chain and a light chain, wherein the light chain comprises a light chain variable region described herein. In some embodiments, the light chain variable region comprises a HVR-L1, a HVR-L2 and a HVR-L3, and wherein at least two of the HVR-L1, HVR-L2, and HVR-L3 comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23. In some embodiments, the light chain variable region comprises a HVR-L2 comprising an amino acid sequence selected from the group consisting of SEQ ID NO:5-9 and a HVR-L3 of the antibody comprising an amino acid sequence selected from the group consisting of SEQ ID NO:10-23. In some embodiments, the light chain variable region comprises a HVR-L1 comprising an amino acid sequence selected from the group consisting of SEQ ID NO:1-4 and a HVR-L2 of the antibody comprises an amino acid sequence selected from the group consisting of SEQ ID NO:5-9. In some embodiments, the light chain variable region comprises a HVR-L1 comprising an amino acid sequence selected from the group consisting of SEQ ID NO:1-4 and a HVR-L3 of the antibody comprising an amino acid sequence selected from the group consisting of SEQ ID NO:10-23. In some embodiments, the light chain variable region comprises a HVR-L1 comprising an amino acid sequence selected from the group consisting of SEQ ID NO:1-4, a HVR-L2 comprising an amino acid sequence selected from the group consisting of SEQ ID NO:5-9, and a HVR-L3 comprising an amino acid sequence selected from the group consisting of SEQ ID NO:10-23. In some embodiments, the light chain variable region comprises three of a HVR-L1, a HVR-L2, and a HVR-L3 selected from the group consisting of: (1) a HVR-L1 comprising the amino acid sequence of SEQ ID NO:1, a HVR-L2 comprising the amino acid sequence of SEQ ID NO:9, and a HVR-L3 selected from the group consisting of SEQ ID NOS:10-23; (2) a HVR-L1 comprising the amino acid sequence of SEQ ID NO:4, a HVR-L2 comprising the amino acid sequence of SEQ ID NO:9, and a HVR-L3 comprising an amino acid sequence selected from the group consisting of SEQ ID NOS:10-23; (3) a HVR-L1 comprising the amino acid sequence of SEQ ID NO:2, a HVR-L2 comprising the amino acid sequence of SEQ ID NO:9, and a HVR-L3 comprising an amino acid sequence selected from the group consisting of SEQ ID NOS:10-23; (4) a HVR-L1 comprising the amino acid sequence of SEQ ID NO:2, a HVR-L2 comprising an amino acid sequence selected from the group consisting of SEQ ID NOS:5-9, and a HVR-L3 comprising the amino acid sequence of SEQ ID NO:18; (5) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:23; (6) a HVR-L1 comprising the amino acid sequence of SEQ ID NO:1, a HVR-L2 sequence selected form the group consisting of SEQ ID NOS:5-9, and a HVR-L3 comprising the amino acid sequence of SEQ ID NO:20; (7) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:18; (8) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:23; (9) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:20; (10) a HVR-L1 comprising the amino acid sequence of SEQ ID NO:3, a HVR-L2 comprising the amino acid sequence of SEQ ID NO:9, and a HVR-L3 comprising an amino acid sequence selected from the group consisting of SEQ ID NOS:10-23; (11) a HVR-L1 comprising the amino acid sequence of SEQ ID NO:4, a HVR-L2 comprising the amino acid sequence of SEQ ID NO:6, and a HVR-L3 comprising an amino acid sequence selected from the group consisting of SEQ ID NOS:10-23; (12) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:23; (13) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:14; (14) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:18; (15) a HVR-L1 comprising the amino acid sequence of SEQ ID NO:3, a HVR-L2 comprising an amino acid sequence selected from the group consisting of SEQ ID NOS:5-9, and a HVR-L3 comprising the amino acid sequence of SEQ ID NO:20; (16) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:14; (17) a HVR-L1 comprising an amino acid sequence selected from the group consisting of SEQ ID NOS:1-4, a HVR-L2 comprising the amino acid sequence of SEQ ID NO:6, and a HVR-L3 comprising the amino acid sequence of SEQ ID NO:23; and (18) a HVR-L1 comprising an amino acid sequence selected from the group consisting of SEQ ID NOS:1-4, a HVR-L2 comprising the amino acid sequence of SEQ ID NO:7, and a HVR-L3 comprising the amino acid sequence of SEQ ID NO:23. In some embodiments, the light chain variable region comprises three of a HVR-L1, a HVR-L2, and a HVR-L3 selected from the group consisting of: (1) a HVR-L1 comprising the amino acid sequence of SEQ ID NO:2, a HVR-L2 comprising the amino acid sequence of SEQ ID NO:9, and a HVR-L3 comprising the amino acid sequence of SEQ ID NO:18; (2) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:23; (3) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:20; (4) a HVR-L1 comprising the amino acid sequence of SEQ ID NO:4, a HVR-L2 comprising the amino acid sequence of SEQ ID NO:9, and a HVR-L3 comprising the amino acid sequence of SEQ ID NO:14; (5) a HVR-L1 comprising the amino acid sequence of SEQ ID NO:3, a HVR-L2 comprising the amino acid sequence of SEQ ID NO:9, and a HVR-L3 comprising the amino acid sequence of SEQ ID NO:20; (6) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:18; (7) a HVR-L1 comprising the amino acid sequence of SEQ ID NO:4, a HVR-L2 comprising the amino acid sequence of SEQ ID NO:7, and a HVR-L3 comprising the amino acid sequence of SEQ ID NO:23; (8) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:23; (9) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:17; (10) a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:20; and (11) a HVR-L1 comprising the amino acid sequence of SEQ ID NO:4, a HVR-L2 comprising the amino acid sequence of SEQ ID NO:8, and a HVR-L3 comprising the amino acid sequence of SEQ ID NO:11. In some embodiments, the light chain variable region comprises a HVR-L1, a HVR-L2, and a HVR-L3 of an antibody listed in Table 2. In some embodiments, the light chain variable region comprises a FW-L1 comprising the amino acid sequence of SEQ ID NO:24, a FW-L2 comprising the amino acid sequence of SEQ ID NO:25, a FW-L3 comprising the amino acid sequence of SEQ ID NO:26, and a FW-L4 comprising the amino acid sequence of SEQ ID NO:27. In some embodiments, the light chain variable region comprises a sequence selected from the group consisting of SEQ ID NOS:28-50. In some embodiments, the antibody binds at least 1 target with an equilibrium dissociation constant (Kd) of between about $10^{-7}$ and about $10^{-11}$ M.

In another aspect, provided herein is a polynucleotide (e.g., a synthetic polynucleotide) encoding any of the antibody light chain variable regions described herein. In some embodiments, the polynucleotide encodes a full length antibody light chain comprising any of the antibody light chain variable regions described herein. In some embodiments, the polynucleotide encodes an antibody comprising any of the antibody light chain variable regions described herein.

In another aspect, provided herein is a library comprising antibody light chain variable regions, wherein at least one (e.g., at least one, at least two, at least three, at least four, at least five, at least ten, at least 50, at least 100 etc.) of the antibody light chain variable regions comprises the amino acid sequence of any of the antibody light chain variable regions described herein. In some embodiments, each of the antibody light chain variable regions in the library comprises the amino acid sequence of any of the antibody light chain variable regions described herein. In some embodiments, the library further comprises one or more antibody heavy chain variable regions. In some embodiments, provided herein is a library comprising full length antibody light chains, wherein at least one (e.g., at least one, at least two, at least three, at least four, at least five, at least ten, at least 50, at least 100 etc.) of the antibody light chains comprises the amino acid sequence of any of antibody light chain variable regions described herein. In some embodiments, each of the antibody light chains in the library comprises the amino acid sequence of any of the antibody light chain variable regions described herein. In some embodiments, the library further comprises one or more full length antibody heavy chains. In some embodiments, provided herein is a library comprising antibodies, wherein at least one (e.g., at least one, at least two, at least three, at least four, at least five, at least ten, at least 50, at least 100 etc.) of the antibodies comprises the amino acid sequence of any of antibody light chain variable regions described herein. In some embodiments, each of the antibodies in the library comprises the amino acid sequence of any of the antibody light chain variable regions described herein.

In another aspect, provided herein are methods of preparing a library comprising providing and assembling the polynucleotide sequences of the library according to any of the preceding embodiments.

In another aspect, provided herein are methods of making an antibody library comprising the steps: (a) selecting one, two or three light chain HVRs comprising a sequence having multiple conformations; and (b) assembling polynucleotide sequences to produce a library of polynucleotides (e.g., synthetic polynucleotides) encoding a plurality of antibody light chain variable region sequences. In some embodiments, the antibody light chain variable region sequences are human antibody sequences. In some embodiments, the antibody light chain variable region comprises a HVR-L1, a HVR-L2 and a HVR-L3, and wherein at least two of the HVR-L1, HVR-L2, and HVR-L3 of the light chain variable region comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23. In some embodiments, the light chain variable region comprises a HVR-L1 comprising an amino acid sequence selected from the group consisting of SEQ ID NOS:1-4 and a HVR-L2 of the antibody comprises an amino acid sequence selected from the group consisting of SEQ ID NOS:5-9. In some embodiments, the light chain variable region comprises a HVR-L1 comprising an amino acid sequence selected from the group consisting of SEQ ID NOS:1-4 and a HVR-L3 of the antibody comprising an amino acid sequence selected from the group consisting of SEQ ID NOS:10-23. In some embodiments, the light chain variable region comprises a HVR-L1 comprising an amino acid sequence selected from the group consisting of SEQ ID NOS:1-4, a HVR-L2 comprising an amino acid sequence selected from the group consisting of SEQ ID NOS:5-9, and a HVR-L3 comprising an amino acid sequence selected from the group consisting of SEQ ID NOS:10-23. In some embodiments, the light chain variable region comprises three of a HVR-L1, a HVR-L2, and a HVR-L3 selected from the group consisting of: (1) a HVR-L1 comprising the amino acid sequence of SEQ ID NO:1, a HVR-L2 comprising the amino acid sequence of SEQ ID NO:9, and a HVR-L3 comprising an amino acid sequence selected from the group consisting of SEQ ID NOS:10-23; (2) a HVR-L1 comprising the amino acid sequence of SEQ ID NO:4, a HVR-L2 comprising the amino acid sequence of SEQ ID NO:9, and a HVR-L3 comprising an amino acid sequence selected from the group consisting of SEQ ID NOS:10-23; (3) a HVR-L1 comprising the amino acid sequence of SEQ ID NO:2, a HVR-L2 comprising the amino acid sequence of SEQ ID NO:9, and a HVR-L3 comprising an amino acid sequence selected from the group consisting of SEQ ID NOS:10-23; (4) a HVR-L1 comprising the amino acid sequence of SEQ ID NO:2, a HVR-L2 comprising an amino acid sequence selected from the group consisting of SEQ ID NOS:5-9, and a HVR-L3 comprising the amino acid sequence of SEQ ID NO:18; (5) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:23; (6) a HVR-L1 comprising the amino acid sequence of SEQ ID NO:1, a HVR-L2 sequence selected form the group consisting of SEQ ID NOS:5-9, and a HVR-L3 comprising the amino acid sequence of SEQ ID NO:20; (7) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:18; (8) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:23; (9) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:20; (10) a HVR-L1 comprising the amino acid sequence of SEQ ID NO:3, a HVR-L2 comprising the amino acid sequence of SEQ ID NO:9, and a HVR-L3 comprising an amino acid sequence selected from the group consisting of SEQ ID NOS:10-23; (11) a HVR-L1 comprising the amino acid sequence of SEQ ID NO:4, a HVR-L2 comprising the amino acid sequence of SEQ ID NO:6, and a HVR-L3 comprising an amino acid sequence selected from the group consisting of SEQ ID NOS:10-23; (12) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:23; (13) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:14; (14) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:18; (15) a HVR-L1 comprising the amino acid sequence of SEQ ID NO:3, a HVR-L2 comprising an amino acid sequence selected from the group consisting of SEQ ID NOS:5-9, and a HVR-L3 comprising the amino acid sequence of SEQ ID NO:20; (16) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:14; (17) a HVR-L1 comprising an amino acid sequence selected from the group consisting of SEQ ID NOS:1-4, a HVR-L2 comprising the amino acid sequence of SEQ ID NO:6, and a HVR-L3 comprising the amino acid sequence of SEQ ID NO:23; and (18) a HVR-L1 comprising an amino acid sequence selected from the group consisting of SEQ ID NOS:1-4, a HVR-L2 comprising the amino acid sequence of SEQ ID NO:7, and a HVR-L3 comprising the amino acid sequence of SEQ ID NO:23. In some embodiments, the light chain variable region comprises three of a HVR-L1, a HVR-L2, and a HVR-L3 selected from the group consisting of: (1) a HVR-L1 comprising the amino acid sequence of SEQ ID NO:2, a HVR-L2 comprising the amino acid sequence of SEQ ID NO:9, and a HVR-L3 comprising the amino acid sequence of SEQ ID NO:18; (2) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:23; (3) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:20; (4) a HVR-L1 comprising the amino acid sequence of SEQ ID NO:4, a HVR-L2 comprising the amino acid sequence of SEQ ID NO:9, and a HVR-L3 comprising the amino acid sequence of SEQ ID NO:14; (5) a HVR-L1 comprising the amino acid sequence of SEQ ID NO:3, a HVR-L2 comprising the amino acid sequence of SEQ ID NO:9, and a HVR-L3 comprising the amino acid sequence of SEQ ID NO:20; (6) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:18; (7) a HVR-L1 comprising the amino acid sequence of SEQ ID NO:4, a HVR-L2 comprising the amino acid sequence of SEQ ID NO:7, and a HVR-L3 comprising the amino acid sequence of SEQ ID NO:23; (8) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:23; (9) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:17; (10) a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:20; and (11) a HVR-L1 comprising the amino acid sequence of SEQ ID NO:4, a HVR-L2 comprising the amino acid sequence of SEQ ID NO:8, and a HVR-L3 comprising the amino acid sequence of SEQ ID NO: 11. In some embodiments, the light chain variable region comprises a HVR-L1, a HVR-L2, and a HVR-L3 of an antibody listed in Table 2. In some embodiments, the light chain variable region comprises a FW-L1 comprising the amino acid sequence of SEQ ID NO:24, a FW-L2 comprising the amino acid sequence of SEQ ID NO:25, a FW-L3 comprising the amino acid sequence of SEQ ID NO:26, and a FW-L4 comprising the amino acid sequence of SEQ ID NO:27. In some embodiments, the light chain variable region comprises a sequence selected from the group consisting of SEQ ID NOS:28-50. In another aspect, provided herein are libraries comprising antigen binding domains, wherein one of the antigen binding domains comprises an antibody light chain variable region comprising a HVR-L1, a HVR-L2 and a HVR-L3, and wherein at least two of the HVR-L1, HVR-L2, and HVR-L3 of the antibody light chain variable region comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23. In some embodiments, the antigen binding domain further comprises an antibody heavy chain variable region. In some embodiments, antibody light chain variable region comprises one or more amino acid sequences according to any of the above embodiments. In some embodiments, the library comprises phages. In some embodiments, the antigen binding domain is displayed on the surface of at least one phage of the library. In some embodiments, the library comprises a plurality of phages that express an antigen binding domain according to any one of the above embodiments displayed on the phage surface.

In another aspect, provided herein are methods of generating a bispecific antibody comprising two antibody heavy chain variable regions and two identical light chain variable regions, comprising: (a) screening for a first antigen binding domain that binds to a first antigen, wherein the first antigen binding domain comprises a first antibody heavy chain variable region and a first antibody light chain variable region, and wherein the first antibody light chain variable region is encoded by a polynucleotide of the library according to any of the preceding embodiments (e.g., the first antigen binding domain comprises a first antibody heavy chain variable region and a first antibody light chain variable region, wherein the first antibody light chain variable region comprises a HVR-L1, a HVR-L2 and a HVR-L3, and wherein at least two of the HVR-L1, HVR-L2, and HVR-L3 of the antibody light chain variable region comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23); (b) screening for a second antigen binding domain that binds to a second antigen, wherein the second antigen binding domain comprises a second antibody heavy chain variable region and a second antibody light chain variable region, wherein the second antibody light chain variable region has the same sequence as the first antibody light chain variable region (e.g., the second antigen binding domain comprises a second antibody heavy chain variable region and a second antibody light chain variable region, wherein the second antibody light chain variable region comprises a HVR-L1, a HVR-L2 and a HVR-L3, and wherein at least two of the HVR-L1, HVR-L2, and HVR-L3 of the antibody light chain variable region comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23); and (c) producing a bispecific antibody comprising the first antigen binding domain and the second antigen binding domain.

In another aspect, provided herein are bispecific antibodies comprising: (a) a first binding domain comprising a first heavy chain variable region and a first light chain variable region, wherein the first binding domain binds to a first target; (b) a second binding domain comprising a second heavy chain variable region and a second light chain variable region, wherein the second binding domain binds to a second target, wherein the second light chain variable region has a sequence identical to the first light chain variable region sequence; wherein each of the first and second light chain variable regions comprise a HVR-L1, a HVR-L2 and a HVR-L3, and wherein at least two of the HVR-L1, HVR-L2, and HVR-L3 comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23. In some embodiments, the light chain variable region comprises a HVR-L2 comprising an amino acid sequence selected from the group consisting of SEQ ID NOS:5-9 and a HVR-L3 of the antibody comprising an amino acid sequence selected from the group consisting of SEQ ID NOS:10-23. In some embodiments, the light chain variable region comprises a HVR-L1 comprising an amino acid sequence selected from the group consisting of SEQ ID NOS:1-4 and a HVR-L2 of the antibody comprises an amino acid sequence selected from the group consisting of SEQ ID NOS:5-9. In some embodiments, the light chain variable region comprises a HVR-L1 comprising an amino acid sequence selected from the group consisting of SEQ ID NOS:1-4 and a HVR-L3 of the antibody comprising an amino acid sequence selected from the group consisting of SEQ ID NOS:10-23. In some embodiments, the light chain variable region comprises a HVR-L1 comprising an amino acid sequence selected from the group consisting of SEQ ID NOS:1-4, a HVR-L2 comprising an amino acid sequence selected from the group consisting of SEQ ID NOS:5-9, and a HVR-L3 comprising an amino acid sequence selected from the group consisting of SEQ ID NOS:10-23. In some embodiments, the light chain variable region comprises three of a HVR-L1, a HVR-L2, and a HVR-L3 selected from the group consisting of: (1) a HVR-L1 comprising the amino acid sequence of SEQ ID NO:1, a HVR-L2 comprising the amino acid sequence of SEQ ID NO:9, and a HVR-L3 comprising an amino acid sequence selected from the group consisting of SEQ ID NOS:10-23; (2) a HVR-L1 comprising the amino acid sequence of SEQ ID NO:4, a HVR-L2 comprising the amino acid sequence of SEQ ID NO:9, and a HVR-L3 comprising an amino acid sequence selected from the group consisting of SEQ ID NOS:10-23; (3) a HVR-L1 comprising the amino acid sequence of SEQ ID NO:2, a HVR-L2 comprising the amino acid sequence of SEQ ID NO:9, and a HVR-L3 comprising an amino acid sequence selected from the group consisting of SEQ ID NOS:10-23; (4) a HVR-L1 comprising the amino acid sequence of SEQ ID NO:2, a HVR-L2 comprising an amino acid sequence selected from the group consisting of SEQ ID NOS:5-9, and a HVR-L3 comprising the amino acid sequence of SEQ ID NO:18; (5) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:23; (6) a HVR-L1 comprising the amino acid sequence of SEQ ID NO:1, a HVR-L2 sequence selected form the group consisting of SEQ ID NOS:5-9, and a HVR-L3 comprising the amino acid sequence of SEQ ID NO:20; (7) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:18; (8) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:23; (9) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:20; (10) a HVR-L1 comprising the amino acid sequence of SEQ ID NO:3, a HVR-L2 comprising the amino acid sequence of SEQ ID NO:9, and a HVR-L3 comprising an amino acid sequence selected from the group consisting of SEQ ID NOS:10-23; (11) a HVR-L1 comprising the amino acid sequence of SEQ ID NO:4, a HVR-L2 comprising the amino acid sequence of SEQ ID NO:6, and a HVR-L3 comprising an amino acid sequence selected from the group consisting of SEQ ID NOS:10-23; (12) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:23; (13) a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:14; (14) a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:18; (15) a HVR-L1 comprising the amino acid sequence of SEQ ID NO:3, a HVR-L2 comprising an amino acid sequence selected from the group consisting of SEQ ID NOS:5-9, and a HVR-L3 comprising the amino acid sequence of SEQ ID NO:20; (16) a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:14; (17) a HVR-L1 comprising an amino acid sequence selected from the group consisting of SEQ ID NOS:1-4, a HVR-L2 comprising the amino acid sequence of SEQ ID NO:6, and a HVR-L3 comprising the amino acid sequence of SEQ ID NO:23; and (18) a HVR-L1 comprising an amino acid sequence selected from the group consisting of SEQ ID NOS:1-4, a HVR-L2 comprising the amino acid sequence of SEQ ID NO:7, and a HVR-L3 comprising the amino acid sequence of SEQ ID NO:23. In some embodiments, the light chain variable region comprises three of a HVR-L1, a HVR-L2, and a HVR-L3 selected from the group consisting of: (1) a HVR-L1 comprising the amino acid sequence of SEQ ID NO:2, a HVR-L2 comprising the amino acid sequence of SEQ ID NO:9, and a HVR-L3 comprising the amino acid sequence of SEQ ID NO:18; (2) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:23; (3) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:20; (4) a HVR-L1 comprising the amino acid sequence of SEQ ID NO:4, a HVR-L2 comprising the amino acid sequence of SEQ ID NO:9, and a HVR-L3 comprising the amino acid sequence of SEQ ID NO:14; (5) a HVR-L1 comprising the amino acid sequence of SEQ ID NO:3, a HVR-L2 comprising the amino acid sequence of SEQ ID NO:9, and a HVR-L3 comprising the amino acid sequence of SEQ ID NO:20; (6) a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:18; (7) a HVR-L1 comprising the amino acid sequence of SEQ ID NO:4, a HVR-L2 comprising the amino acid sequence of SEQ ID NO:7, and a HVR-L3 comprising the amino acid sequence of SEQ ID NO:23; (8) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:23; (9) a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:17; (10) a HVR-L1 comprising the amino acid sequence of SEQ ID NO:4, a HVR-L2 comprising the amino acid sequence of SEQ ID NO:5, and a HVR-L3 comprising the amino acid sequence of SEQ ID NO:20; and (11) a HVR-L1 comprising the amino acid sequence of SEQ ID NO:4, a HVR-L2 comprising the amino acid sequence of SEQ ID NO:8, and a HVR-L3 comprising the amino acid sequence of SEQ ID NO:11. In some embodiments, the light chain variable region comprises a HVR-L1, a HVR-L2, and a HVR-L3 of an antibody listed in Table 2. In some embodiments, the light chain variable region comprises a FW-L1 comprising the amino acid sequence of SEQ ID NO:24, a FW-L2 comprising the amino acid sequence of SEQ ID NO:25, a FW-L3 comprising the amino acid sequence of SEQ ID NO:26, and a FW-L4 comprising the amino acid sequence of SEQ ID NO:27. In some embodiments, the light chain variable region comprises a sequence selected from the group consisting of SEQ ID NOS:28-50. In some embodiments, the first heavy chain variable region is linked to a first heavy chain constant region, wherein the second heavy chain variable region is linked to a second heavy chain constant region, wherein the first antibody light chain variable region is linked to a first light chain constant region, wherein the second antibody light chain variable region is linked to a second light chain constant region, and wherein the first and the second antibody light chains have identical sequences.

In another aspect, provided herein are kits comprising the library of polynucleotides or the population of cells comprising the polynucleotides according to any of the preceding embodiments.

It is to be understood that one, some, or all of the properties of the various embodiments described above and herein may be combined to form other embodiments of the present invention. These and other aspects of the invention will become apparent to one of skill in the art. These and other embodiments of the invention are further described by the detailed description that follows.

DETAILED DESCRIPTION

Figures 1A, 1B:
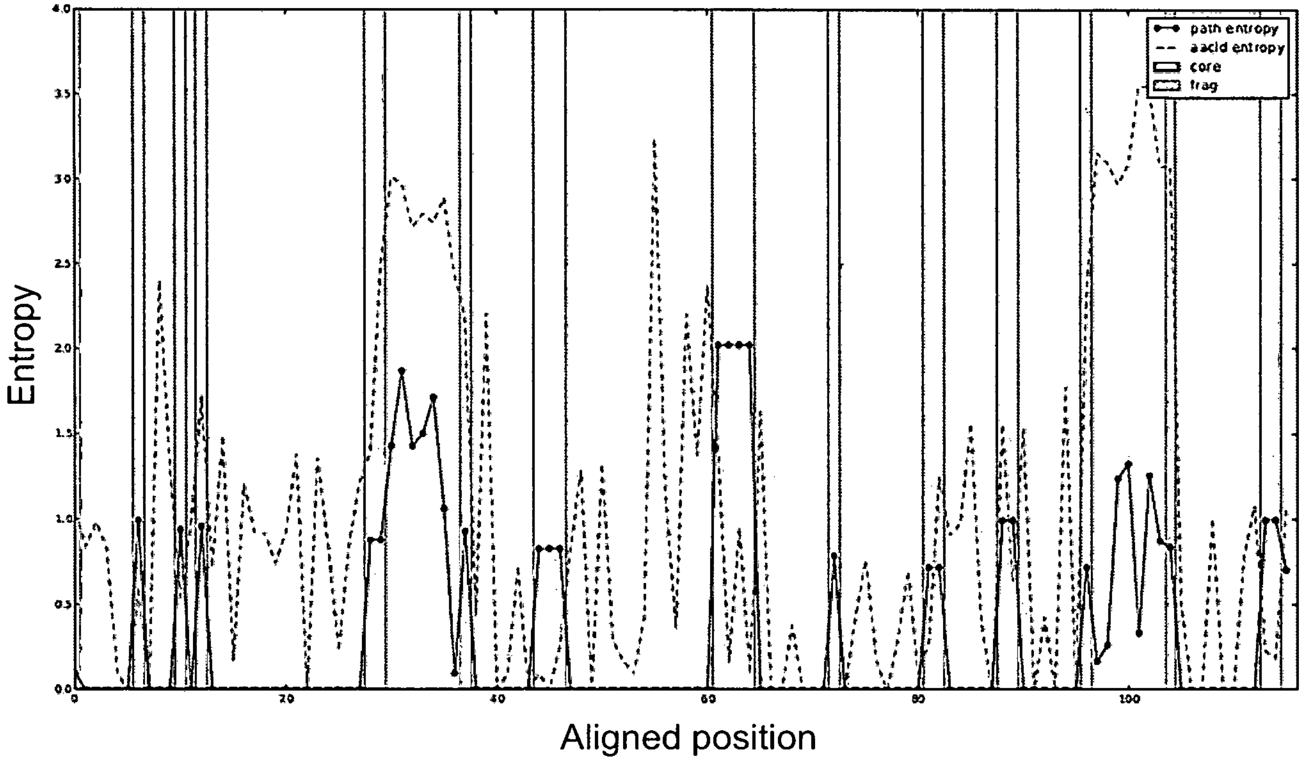
FIG. 1A shows an entropy plot by residue number for the amino acids of a VL domain. 81 VL structures of human antibodies were used to calculate the entropy.
FIG. 1B shows the definition of the hyper-variable regions (HVRs) used herein for an exemplary antibody light chain variable domain (VL) sequence (SEQ ID NO:60) in comparison to the Kabat definition of the complementarity-determining regions (CDRs) for the same VL sequence.

The present disclosure provides libraries containing (e.g., non-naturally occurring or synthetic) polynucleotides that encode antibody light chains (e.g., light chains of a dynamic human antibody). Advantageously, the antibody light chains disclosed herein include HVR sequences designed to generate highly flexible loops for more effective substrate binding and/or specificity against multiple substrates of interest. These HVR sequences are thought to allow the creation of smaller antibody libraries than existing techniques.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): PCR 2: A Practical Approach (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

II. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "antibody" is used herein in the broadest sense and specifically covers monoclonal antibodies (including full length monoclonal antibodies), polyclonal antibodies, multispecific antibodies (e.g., bispecific antibodies), and antibody fragments (e.g., a single-chain variable fragment or scFv) so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology,* 8th Ed., Daniel P. Stites, Abba I. Terr and Tristram G. Parslow (eds.), Appleton & Lange, Norwalk, CT, 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, 4th ed. (W.B. Saunders Co., 2000).

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The term "full-length antibody" (the terms "intact" antibody or "whole" antibody may be used interchangeably herein) may refer to an antibody in its substantially intact form, as opposed to an antibody fragment. Similarly, the term "full-length antibody light chain" (the terms "intact" antibody light chain or "whole" antibody light chain may be used interchangeably herein) may refer to an antibody light chain in its substantially intact form, as opposed to an antibody light chain fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature,* 256:495-97 (1975); Hongo et al., *Hybridoma,* 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); *Neuberger, Nature Biotechnol.* 14:826 (1996); and Lonberg and Huszar, *Intern. Rev. Immunol.* 13:65-93 (1995).

As used herein, "hypervariable region (HVR)" refers to the regions of an antibody domain which are hypervariable in sequence and/or form structurally defined loops. Generally, antibodies comprise six HVRs; three in the VH (H1, H2, H3), and three in the VL (L1, L2, L3). See, e.g., Xu et al., *Immunity* 13:37-45 (2000); Johnson and Wu, in *Methods in Molecular Biology* 248:1-25 (Lo, ed., Human Press, Totowa, N.J., 2003). Each VH and VL is composed of three HVRs and four framework (FW) regions arranged from amino terminus to carboxy terminus in the following order: FW1-HVR1-FW2-HVR2-FW3-HVR3-FW4. Throughout the present disclosure, the three HVRs of the light chain are referred to as HVR-L1, HVR-L2, and HVR-L3. For comparison, the definition of the HVRs (as used herein) is contrasted with the Kabat definition of the complementarity-determining regions (CDRs) (Yvonne Chen et al. (1999) "Selection and Analysis of an Optimized Anti-VEGF Antibody: Crystal Structure of an Affinity-matured Fab in Complex with Antigen", *J. Mol. Biol.* 293, 865-881) for the exemplary antibody light chain variable domain shown in FIG. 1B.

As used herein, "library" refers to a set of two or more entities having a shared class. For example, a library containing polynucleotides may refer to a set of two or more polynucleotides. The term "library" is used herein in the broadest sense and specifically covers sub-libraries that may or may not be combined.

As used herein, "unique" refers to a member of a set that is different from other members of the set. For example, a unique antibody from a library encoding a plurality of polynucleotides encoding antibodies may refer to an antibody having a particular sequence not shared by other antibodies encoded by the library. As a practical matter, it is to be understood that a "unique" member of a physical realization of a library may be present in more than one copy. For example, a library may contain a plurality of "unique" antibodies, with one or more of the "unique" antibody molecules occurring in more than one copy.

As used herein, "diversity" refers to a variety and/or heterogeneity. For example, a diversity of antibodies in a library may refer to a variety of antibodies with unique sequences present in the library.

The terms "polypeptide," "protein," and "peptide" are used interchangeably herein and may refer to polymers of two or more amino acids.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thiolate"), P(S)S ("dithioate"), (O)NR2 ("amidate"), P(O)R, P(O)OR', CO, or CH2 ("formacetal"), in which each R or R' is independently H or substituted or unsubstituted alkyl (1-20° C.) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

An "isolated" (such as an isolated polypeptide, nucleic acid, or cell) refers to a molecule that has been separated from a component of its natural environment.

A cell (e.g., a cell or population of cells comprising a synthetic polynucleotide or library of synthetic polynucleotides) or an isolated cell includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) (e.g., a synthetic polynucleotide that encodes an antibody light chain variable region of the present disclosure).

A "non-human animal" refers to any animal not classified as a human, such as domestic, farm, or zoo animals, sports, pet animals (such as dogs, horses, cats, cows, etc.), as well as animals used in research. Research animals may refer without limitation to nematodes, arthropods, vertebrates, mammals, frogs, rodents (e.g., mice or rats), fish (e.g., zebrafish or pufferfish), birds (e.g., chickens), dogs, cats, and non-human primates (e.g., rhesus monkeys, cynomolgus monkeys, chimpanzees, etc.). In preferred embodiments, the animal is one that produces antibodies.

III. Antibody Libraries and Generation of Libraries

Certain aspects of the present disclosure relate to libraries of polynucleotides, e.g., that encode an antibody heavy chain variable region (VH) or light chain variable region (VL). A library of the present disclosure can contain one or more polynucleotides encoding a light chain variable region comprising a HVR-L1, a HVR-L2, and a HVR-L3, each independently comprising a HVR sequence described herein (e.g., a HVR sequence shown in Table 1).

In some embodiments, a library of the present disclosure contains a smaller number of unique light chain HVR sequences and/or unique VL sequences than typical antibody libraries. Advantageously, such libraries can provide sufficient diversity for the identification of antibodies binding one or more of a number of antigens of interest while also allowing for more efficient screening due to the reduced library size. In some embodiments, a library of the present disclosure includes or consists of polynucleotides containing less than about 1000, less than about 900, less than about 800, less than about 700, less than about 600, less than about 500, less than about 400, or less than about 300 unique combinations of HVR-L1, HVR-L2, and HVR-L3 sequences. In certain embodiments, a library of the present disclosure includes or consists of polynucleotides containing about 280 or less unique combinations of HVR-L1, HVR-L2, and HVR-L3 sequences.

In some embodiments, a library contains a plurality of polynucleotides, with at least one of the polynucleotides encoding an antibody light chain variable region of the present disclosure (e.g., comprising a HVR-L1, HVR-L2, and HVR-L3 of the present disclosure). In some embodiments, one or more of the polynucleotides encode an antibody light chain variable region comprising a HVR-L1, a HVR-L2 and a HVR-L3, where at least one or at least two of the HVR-L1, HVR-L2, and HVR-L3 comprise an amino acid sequence selected from a HVR-L1 sequence of the present disclosure (e.g., SEQ ID NOS:1-4), a HVR-L2 sequence of the present disclosure (e.g., SEQ ID NOS:5-9), and a HVR-L3 sequence of the present disclosure (e.g., SEQ ID NOS:10-23). In some embodiments, at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 225, or at least 250 of the polynucleotides encodes an antibody light chain variable region comprising a HVR-L1, a HVR-L2 and a HVR-L3, where at least one or at least two of the HVR-L1, HVR-L2, and HVR-L3 comprise an amino acid sequence selected from a HVR-L1 sequence of the present disclosure (e.g., SEQ ID NOS:1-4), a HVR-L2 sequence of the present disclosure (e.g., SEQ ID NOS:5-9), and a HVR-L3 sequence of the present disclosure (e.g., SEQ ID NOS:10-23); and/or less than 300, or less than or equal to 280 of the polynucleotides encodes an antibody light chain variable region comprising a HVR-L1, a HVR-L2 and a HVR-L3, where at least one or at least two of the HVR-L1, HVR-L2, and HVR-L3 comprise an amino acid sequence selected from a HVR-L1 sequence of the present disclosure (e.g., SEQ ID NOS:1-4), a HVR-L2 sequence of the present disclosure (e.g., SEQ ID NOS:5-9), and a HVR-L3 sequence of the present disclosure (e.g., SEQ ID NOS:10-23). In certain embodiments, each of the polynucleotides of the library encodes an antibody light chain variable region comprising a HVR-L1, a HVR-L2 and a HVR-L3, where at least one or at least two of the HVR-L1, HVR-L2, and HVR-L3 comprise an amino acid sequence selected from a HVR-L1 sequence of the present disclosure (e.g., SEQ ID NOS:1-4), a HVR-L2 sequence of the present disclosure (e.g., SEQ ID NOS:5-9), and a HVR-L3 sequence of the present disclosure (e.g., SEQ ID NOS:10-23). In some embodiments, one or more polynucleotides of the library are in a vector (e.g., an expression vector or display vector).

In some embodiments, the polynucleotides in the library encodes an antibody light chain variable region comprising a HVR-L1, a HVR-L2 and a HVR-L3, wherein HVR-L1 comprises a sequence selected from the consisting of SEQ ID NOS:1-4). In some embodiments, the polynucleotides in the library encodes an antibody light chain variable region comprising a HVR-L1, a HVR-L2 and a HVR-L3, wherein HVR-L2 comprises a sequence selected from the consisting of SEQ ID NOS:5-9). In some embodiments, the polynucleotides in the library encodes an antibody light chain variable region comprising a HVR-L1, a HVR-L2 and a HVR-L3, wherein HVR-L1 comprises a sequence selected from the consisting of SEQ ID NOS:10-23).

The light chain HVR sequences described herein may be included in any combination in a library of the present disclosure. In some embodiments, a light chain variable region comprises a HVR-L2 comprising an amino acid sequence selected from the group consisting of SEQ ID NOS:5-9 and a HVR-L3 of the antibody comprising an amino acid sequence selected from the group consisting of SEQ ID NOS:10-23. In some embodiments, a light chain variable region comprises a HVR-L1 comprising an amino acid sequence selected from the group consisting of SEQ ID NOS:1-4 and a HVR-L2 of the antibody comprises an amino acid sequence selected from the group consisting of SEQ ID NOS:5-9. In some embodiments, a light chain variable region comprises a HVR-L1 comprising an amino acid sequence selected from the group consisting of SEQ ID NOS:1-4 and a HVR-L3 of the antibody comprising an amino acid sequence selected from the group consisting of SEQ ID NOS:10-23. In some embodiments, a light chain variable region comprises a HVR-L1 comprising an amino acid sequence selected from the group consisting of SEQ ID NOS:1-4, a HVR-L2 comprising an amino acid sequence selected from the group consisting of SEQ ID NOS:5-9, and a HVR-L3 comprising an amino acid sequence selected from the group consisting of SEQ ID NOS:10-23.

In certain embodiments, a light chain variable region comprises three of a HVR-L1, a HVR-L2, and a HVR-L3 selected from the group consisting of: a HVR-L1 comprising the amino acid sequence of SEQ ID NO:1, a HVR-L2 comprising the amino acid sequence of SEQ ID NO:9, and a HVR-L3 comprising an amino acid sequence selected from the group consisting of SEQ ID NOS:10-23; a HVR-L1 comprising the amino acid sequence of SEQ ID NO:2, a HVR-L2 comprising an amino acid sequence selected from the group consisting of SEQ ID NOS:5-9, and a HVR-L3 comprising the amino acid sequence of SEQ ID NO:18; a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NOS: 23; a HVR-L1 comprising the amino acid sequence of SEQ ID NO:1, a HVR-L2 comprising an amino acid sequence selected from the group consisting of SEQ ID NOS:5-9, and a HVR-L3 sequence comprising the amino acid sequence of SEQ ID NOS:20; a HVR-L1 selected from the group consisting of SEQ ID NOS:1-4, a HVR-L2 comprising the amino acid sequence of SEQ ID NO:9, and a HVR-L3 comprising the amino acid sequence of SEQ ID NOS:18; a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:23; a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:20; a HVR-L1 comprising the amino acid sequence of SEQ ID NO:3, a HVR-L2 comprising the amino acid sequence of SEQ ID NO:9, and a HVR-L3 comprising an amino acid sequence selected from the group consisting of SEQ ID NOS:10-23; a HVR-L1 comprising the amino acid sequence of SEQ ID NO:4, a HVR-L2 comprising the amino acid sequence of SEQ ID NO:6, and a HVR-L3 comprising an amino acid sequence selected from the group consisting of SEQ ID NOS:10-23; a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:23; a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:14; a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:18; a HVR-L1 comprising the amino acid sequence of SEQ ID NO:3, a HVR-L2 comprising an amino acid sequence selected from the group consisting of SEQ ID NOS:5-9, and a HVR-L3 comprising the amino acid sequence of SEQ ID NO:20; a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:14; a HVR-L1 comprising an amino acid sequence selected from the group consisting of SEQ ID NOS:1-4, a HVR-L2 comprising the amino acid sequence of SEQ ID NO:6, and a HVR-L3 comprising the amino acid sequence of SEQ ID NO:23; and a HVR-L1 comprising an amino acid sequence selected from the group consisting of SEQ ID NOS:1-4, a HVR-L2 comprising the amino acid sequence of SEQ ID NO:7, and a HVR-L3 comprising the amino acid sequence of SEQ ID NO:23. In certain embodiments, a light chain variable region comprises three of a HVR-L1, a HVR-L2, and a HVR-L3 selected from the group consisting of: a HVR-L1 comprising the amino acid sequence of SEQ ID NO:2, a HVR-L2 comprising the amino acid sequence of SEQ ID NO:9, and a HVR-L3 comprising the amino acid sequence of SEQ ID NO:18; a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:23; a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:20; a HVR-L1 comprising the amino acid sequence of SEQ ID NO:4, a HVR-L2 comprising the amino acid sequence of SEQ ID NO:9, and a HVR-L3 comprising the amino acid sequence of SEQ ID NO:14; a HVR-L1 comprising the amino acid sequence of SEQ ID NO:3, a HVR-L2 comprising the amino acid sequence of SEQ ID NO:9, and a HVR-L3 comprising the amino acid sequence of SEQ ID NO:20; a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:18; a HVR-L1 comprising the amino acid sequence of SEQ ID NO:4, a HVR-L2 comprising the amino acid sequence of SEQ ID NO:7, and a HVR-L3 comprising the amino acid sequence of SEQ ID NO:23; a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:23; and a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:17; a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO: 17; a HVR-L1 comprising the amino acid sequence of SEQ ID NO: 4, a HVR-L2 comprising an amino acid sequence of SEQ ID NO:5, and a HVR-L3 comprising an amino acid sequence of SEQ ID NO: 20; and a HVR-L1 comprising an amino acid sequence of SEQ ID NO: 4, a HVR-L2 comprising the amino acid sequence of SEQ ID NO: 8, and a HVR-L3 comprising an amino acid sequence of SEQ ID NO: 11. In some embodiments, a light chain variable region comprises three of a HVR-L1, a HVR-L2, and a HVR-L3 of an antibody listed in Table 2. In some embodiments, a light chain variable region comprises three of a HVR-L1, a HVR-L2, and a HVR-L3 listed in Table 1. In some embodiments, a light chain variable region comprises a sequence selected from SEQ ID NOS:28-50 or a sequence having at least 85%, at least 90%, or at least 95% sequence identity to a sequence selected from SEQ ID NOS:28-50.

In some embodiments, a light chain variable region further comprises variable region light chain framework sequences juxtaposed between the HVRs according to the formula: (FW-L1)-(HVR-L1)-(FW-L2)-(HVR-L2)-(FW-L3)-(HVR-L3)-(FW-L4). In some embodiments, one, two, three, or four of the framework sequences is/are the following:

```
                                  (SEQ ID NO: 24)
FW-L1 is
DIQLTQSPSSLSASVGDRVTITC

                                  (SEQ ID NO: 25)
FW-L2 is
WYQQKPGKAPKLLIY

                                  (SEQ ID NO: 26)
FW-L3 is
PSRFSGSGSGTDFTLTISSLQPEDFATY
```

FW-L4 is FGQGTKVEIKR (SEQ ID NO:27).

In some embodiments, a library contains a plurality of polynucleotides, with at least one of the polynucleotides encoding an antibody heavy chain variable region (e.g., comprising a HVR-H1, HVR-H2, and HVR-H3). In some embodiments, a library contains a plurality of polynucleotides that encodes at least $10^3$, at least $10^4$, at least $10^5$, at least $10^6$, at least $10^7$, at least $10^8$, at least $10^9$, at least $10^{10}$, at least $10^{11}$, or at least $10^{12}$ unique sequences of antibody heavy chain variable regions. In some embodiments, a library contains a plurality of polynucleotides that encodes at least $10^3$ unique sequences of antibody heavy chain variable regions. In some embodiments, a library contains a plurality of polynucleotides that encodes at least $10^9$ unique sequences of antibody heavy chain variable regions. In other embodiments, a library contains a polynucleotide that encodes one antibody heavy chain variable region. In some embodiments, a library contains a plurality of polynucleotides that encodes from 1 to about $10^3$ unique sequences of antibody heavy chain variable regions.

In some embodiments, one or more of the polynucleotides of a library encode(s) full-length antibody light chain(s). In other embodiments, one or more of the polynucleotides of a library encode(s) light chain Fab fragment(s). In some embodiments, one or more of the polynucleotides of a library encode(s) single-chain variable fragment(s).

In some embodiments, a library contains a plurality of polynucleotides that encodes a plurality of unique antibodies. In some embodiments, each antibody comprises a heavy chain variable region and a light chain variable region. In some embodiments, the light chain variable region of each antibody of the plurality comprises an identical sequence and comprises a HVR-L1, a HVR-L2 and a HVR-L3. In some embodiments, at least one or at least two of the HVR-L1, HVR-L2, and HVR-L3 comprise an amino acid sequence selected from a HVR-L1 sequence of the present disclosure (e.g., SEQ ID NOS:1-4), a HVR-L2 sequence of the present disclosure (e.g., SEQ ID NOS:5-9), and a HVR-L3 sequence of the present disclosure (e.g., SEQ ID NOS:10-23). The light chain HVR sequences described herein may be included in any combination in a library of the present disclosure that also includes polynucleotides encoding one or more heavy chain variable region(s).

In some embodiments, a library of the present disclosure includes one or more vectors encoding one or more polynucleotides (e.g., synthetic polynucleotides) of the present disclosure. For example, in some embodiments, the library includes one or more vectors encoding one or more polynucleotides (e.g., synthetic polynucleotides) encoding an antibody light chain variable region, wherein the antibody light chain variable region comprises a HVR-L1, a HVR-L2 and a HVR-L3, and wherein at least two of the HVR-L1, HVR-L2, and HVR-L3 of the antibody light chain variable region comprise an amino acid sequence selected from a HVR-L1 sequence selected from the group consisting of SEQ ID NOS:1-4, a HVR-L2 sequence selected from the group consisting of SEQ ID NOS:5-9, and a HVR-L3 sequence selected from the group consisting of SEQ ID NOS:10-23).

Further provided herein is a method of preparing a library, e.g., by providing and assembling the polynucleotide sequences (e.g., synthetic polynucleotide(s)) of a library of the present disclosure. Further provided herein is a method of making a library, e.g., by selecting one, two, or three light chain HVRs (e.g., one, two, or three light chain HVRs of the present disclosure) comprising a sequence having multiple conformations and assembling polynucleotide sequences to produce a library of polynucleotides (e.g., synthetic polynucleotides) encoding a plurality of antibody light chain variable region sequences. In some embodiments, the antibody light chain variable region sequences are human antibody sequences. In some embodiments, the antibody light chain variable region comprises a HVR-L1, a HVR-L2 and a HVR-L3, and at least two of the HVR-L1, HVR-L2, and HVR-L3 comprise an amino acid sequence selected from a HVR-L1 sequence of the present disclosure (e.g., SEQ ID NOS:1-4), a HVR-L2 sequence of the present disclosure (e.g., SEQ ID NOS:5-9), and a HVR-L3 sequence of the present disclosure (e.g., SEQ ID NOS:10-23).

In some embodiments, at least one of the HVR-L1, HVR-L2, and HVR-L3 of the antibody light chain variable region adopts multiple conformations. In some embodiments, the multiple conformations can be assayed or detected using techniques known in the art, including without limitation structural determination (e.g., X-ray crystallography or NMR) and/or computational modeling.

Polynucleotides encoding a set of antibody light and/or heavy chain variable regions can be cloned into any suitable vector for expression of a portion or the entire light or heavy chain sequences. In some embodiments, the polynucleotide cloned into a vector allows production of a portion or the entire light or heavy chain sequence fused to all or a portion of a viral coat protein (i.e., creating a fusion protein) and displayed on the surface of a particle or cell. Several types of vectors are available and may be used to practice this invention, for example, phagemid vectors. Phagemid vectors generally contain a variety of components including promoters, signal sequences, phenotypic selection genes, origin of replication sites, and other necessary components as are known to those of ordinary skill in the art. In some embodiments, the polynucleotides encoding a set of antibody light and/or heavy chain variable regions can closed into vectors for expressing in bacterial cells for bacterial display or in yeast cells for yeast display. Exemplary vectors are described in US PG Pub. No. US20160145604. In some embodiments, the vector is a display vector comprising, from 5' to 3', a polynucleotide encoding an amino acid sequence to be displayed on a surface (e.g., a surface of phage, bacteria, yeast, or mammalian cells), a restriction site, a second polynucleotide encoding a surface peptide capable of being displayed on the surface, and a second restriction site. In some embodiments, the second polynucleotide encodes a phage coat protein, a yeast outer wall protein, a bacterial outer membrane protein, a cell surface tether domain, or an adapter, or a truncation or derivative thereof. In certain embodiments, the second polynucleotide is gene III of filamentous phage M13, or a truncation or derivative thereof. In some embodiments, the surface peptide is for phage display, yeast display, bacterial display or mammalian display, or shuttling display therebetween. In some embodiments, when expressed, the amino acid sequence and the surface peptide are displayed as a fusion protein on the surface. In some embodiments, the vector further comprises a fusion tag 5' to the first restriction site or 3' to the second restriction site.

Certain aspects of the present disclosure relate to a population of cells containing vector(s) described herein. Antibody light and/or heavy chains encoded by polynucleotides generated by any of the techniques described herein, or other suitable techniques, can be expressed and screened to identify antibodies having desired structure and/or activity. Expression of the antibodies can be carried out, for example, using cell-free extracts (e.g., ribosome display), phage display, prokaryotic cells (e.g., bacterial display), or eukaryotic cells (e.g., yeast display). In some embodiments, the cells are bacterial cells, yeast cells, or mammalian cells. Methods for transfecting bacterial cells, yeast cells, or mammalian cells are known in the art and described in the references cited herein. Expression (e.g., from a library of the present disclosure) of polypeptides (e.g., antibody chains) in these cell types, as well as screening for antibodies of interest, are described in more detail below.

Alternatively, the polynucleotides can be expressed in an *E. coli* expression system, such as that described by Pluckthun and Skerra. (Meth. Enzymol., 1989, 178: 476; Biotechnology, 1991, 9: 273). The mutant proteins can be expressed for secretion in the medium and/or in the cytoplasm of the bacteria, as described by Better and Horwitz, Meth. Enzymol., 1989, 178: 476. In some embodiments, the single domains encoding VH and VL are each attached to the 3' end of a sequence encoding a signal sequence, such as the ompA, phoA or pelB signal sequence (Lei et al., J. Bacteriol., 1987, 169: 4379). These gene fusions are assembled in a dicistronic construct, so that they can be expressed from a single vector and secreted into the periplasmic space of *E. coli* where they will refold and can be recovered in active form. (Skerra et al., Biotechnology, 1991, 9: 273). For example, antibody heavy chain genes can be concurrently expressed with antibody light chain genes to produce antibodies or antibody fragments.

In other embodiments, the antibody sequences are expressed on the membrane surface of a prokaryote, e.g., *E. coli*, using a secretion signal and lipidation moiety as described, e.g., in US20040072740; US20030100023; and US20030036092.

Alternatively, antibodies can be expressed and screened by anchored periplasmic expression (APEx 2-hybrid surface display), as described, for example, in Jeong et al., PNAS, 2007, 104: 8247 or by other anchoring methods as described, for example, in Mazor et al., Nature Biotechnology, 2007, 25: 563.

Higher eukaryotic cells, such as mammalian cells, for example myeloma cells (e.g., NS/0 cells), hybridoma cells, Chinese hamster ovary (CHO), and human embryonic kidney (HEK) cells, can also be used for expression of the antibodies of the present disclosure. Typically, antibodies expressed in mammalian cells are designed to be secreted into the culture medium, or expressed on the surface of the cell. The antibody or antibody fragments can be produced, for example, as intact antibody molecules or as individual VH and VL fragments, Fab fragments, single domains, or as single chains (scFv).

In other embodiments, antibodies can be selected using mammalian cell display (Ho et al., PNAS, 2006, 103: 9637). In some embodiments, as described above and exemplified below, antibodies can be selected after production of a portion or the entire light or heavy chain sequence fused to all or a portion of a viral coat protein (i.e., creating a fusion protein) and displayed on the surface of a particle or cell, e.g., using phage display.

Certain aspects of the present disclosure relate to a non-human animal comprising a polynucleotide library of the present disclosure. For example, a non-human animal of the present disclosure may be modified such that its genome includes a polynucleotide encoding a light chain variable region of the present disclosure. In a non-limiting example, a transgenic mouse is generated that includes a light chain immunoglobulin locus (e.g., a VL locus) modified to express one or more of the light chain variable regions of the present disclosure. In some embodiments, the transgenic animal (e.g., mouse) expresses antibodies or light chains encoded by the polynucleotides. Techniques for modifying one or more immunoglobulin loci of a non-human animal are known in the art (e.g., methods used to generate Xenomouse™).

The screening of the antibodies derived from the libraries of the present disclosure can be carried out by any appropriate means known in the art. For example, binding activity can be evaluated by standard immunoassay and/or affinity chromatography. Screening of the antibodies of the invention for catalytic function, e.g., proteolytic function can be accomplished using a standard assays, e.g., a hemoglobin plaque assay. Determining binding affinity of an antibody to a target can be assayed in vitro using a variety of well-known techniques, e.g., a BIACORE™ instrument, which measures binding rates of an antibody to a given target or antigen based on surface plasmon resonance, or Bio-Layer Interferometry (BLI), as exemplified below using the ForteBio Octet® RED96 platform (Pall Life Sciences). In vivo assays can be conducted using any of a number of animal models and then subsequently tested, as appropriate, in humans. Cell-based biological assays are also contemplated. The antibodies or antigen binding fragments can be further selected for functional activity, for example, antagonist or agonist activity. Exemplary screening methods are described herein. For example, in some embodiments, affinity of binding between fab fragment(s) and one or more target(s) is measured using BLI by tagging antigens with human IgG1-Fc tag and capture by Anti-hIgG-Fc Capture (AHC) Biosensor. Fabs can be tagged at their C-terminus of the CH1 domain with a His6 tag, over-expressed in a host cell such as *E. coli*, and purified, e.g., using a Ni-NTA resin. Affinity can then be measured using AHC sensors (anti-human IgG-Fc capture dip and read biosensors) dipped into wells containing the purified fabs diluted, e.g., to 5-10 μg/mL with kinetic buffer.

After binders are identified by binding to the target or antigen, and/or functional assays the nucleic acid can be extracted. Extracted DNA can then be used directly to transform *E. coli* host cells or alternatively, the encoding sequences can be amplified, for example using PCR with suitable primers, and sequenced by any typical sequencing method. Variable domain DNA of the binders can be restriction enzyme digested and then inserted into a vector for protein expression.

IV. Antibodies and Antibody Production

Provided herein are antibodies identified and selected from the libraries described herein. Certain aspects of the present disclosure relate to antibody light chain or heavy chain HVRs, variable regions comprising the HVRs, and/or polynucleotide(s) encoding the same. In some embodiments, the HVRs and/or variable regions are part of an antibody fragment, full-length antibody, or single-chain variable fragment (scFv).

In some embodiments, a light chain variable region comprises one, two, or three of HVR-L1 HVR-L2 and HVR-L3 sequences listed in Table 1 below.

TABLE 1

Light chain HVR sequences

| SEQ ID NO. | Designed Sequence |
|---|---|
| HVR-L1 | |
| 1 | RASQGISSYLA |
| 2 | RASQSVSSYLA |
| 3 | RASQGVSSYLA |
| 4 | RASQSISSYLN |
| HVR-L2 | |
| 5 | AASSLQSGV |
| 6 | DASSLESGV |
| 7 | AASTLQSGV |
| 8 | DASNRATGI |
| 9 | DASNLETGV |
| HVR-L3 | |
| 10 | HCQHYAGYSAT |
| 11 | YCQQSYSTPPT |
| 12 | YCQQSYSTPRT |
| 13 | YCQQWSSHPQT |
| 14 | YCQHHYGTPLT |
| 15 | YCQQSYSTSHT |
| 16 | YCQQSYSTPNT |
| 17 | YCQQWSSSPLT |
| 18 | YCQQSYSTPLT |
| 19 | YCQQYGSSPLT |
| 20 | YCQQYYTTPLT |
| 21 | YCKQAYIPPLT |
| 22 | YCFQGSHVPRT |
| 23 | YCQQYYSTPLT |

In some embodiments, a light chain variable region comprises three of a HVR-L1, a HVR-L2, and a HVR-L3 of an antibody listed in Table 2 below.

TABLE 2

| Combinations of light chain HVR sequences | | | | | | |
|---|---|---|---|---|---|---|
| | VR1 Variable Region | | VR2 Variable Region | | VR3 Variable Region | |
| Antibody Number | Sequence | SEQ ID NO | Sequence | SEQ ID NO | Sequence | SEQ ID NO |
| 1 | RASQGISSYLA | 1 | AASSLQSGV | 5 | HCQHYAGYSAT | 10 |
| 2 | RASQGISSYLA | 1 | AASSLQSGV | 5 | YCQQSYSTPPT | 11 |
| 3 | RASQGISSYLA | 1 | AASSLQSGV | 5 | YCQQSYSTPRT | 12 |
| 4 | RASQGISSYLA | 1 | AASSLQSGV | 5 | YCQQWSSHPQT | 13 |
| 5 | RASQGISSYLA | 1 | AASSLQSGV | 5 | YCQHHYGTPLT | 14 |
| 6 | RASQGISSYLA | 1 | AASSLQSGV | 5 | YCQQSYSTSHT | 15 |
| 7 | RASQGISSYLA | 1 | AASSLQSGV | 5 | YCQQSYSTPNT | 16 |
| 8 | RASQGISSYLA | 1 | AASSLQSGV | 5 | YCQQWSSSPLT | 17 |
| 9 | RASQGISSYLA | 1 | AASSLQSGV | 5 | YCQQSYSTPLT | 18 |
| 10 | RASQGISSYLA | 1 | AASSLQSGV | 5 | YCQQYGSSPLT | 19 |
| 11 | RASQGISSYLA | 1 | AASSLQSGV | 5 | YCQQYYTTPLT | 20 |
| 12 | RASQGISSYLA | 1 | AASSLQSGV | 5 | YCKQAYIPPLT | 21 |
| 13 | RASQGISSYLA | 1 | AASSLQSGV | 5 | YCFQGSHVPRT | 22 |
| 14 | RASQGISSYLA | 1 | AASSLQSGV | 5 | YCQQYYSTPLT | 23 |
| 15 | RASQGISSYLA | 1 | DASSLESGV | 6 | HCQHYAGYSAT | 10 |
| 16 | RASQGISSYLA | 1 | DASSLESGV | 6 | YCQQSYSTPPT | 11 |
| 17 | RASQGISSYLA | 1 | DASSLESGV | 6 | YCQQSYSTPRT | 12 |
| 18 | RASQGISSYLA | 1 | DASSLESGV | 6 | YCQQWSSHPQT | 13 |
| 19 | RASQGISSYLA | 1 | DASSLESGV | 6 | YCQHHYGTPLT | 14 |
| 20 | RASQGISSYLA | 1 | DASSLESGV | 6 | YCQQSYSTSHT | 15 |
| 21 | RASQGISSYLA | 1 | DASSLESGV | 6 | YCQQSYSTPNT | 16 |
| 22 | RASQGISSYLA | 1 | DASSLESGV | 6 | YCQQWSSSPLT | 17 |
| 23 | RASQGISSYLA | 1 | DASSLESGV | 6 | YCQQSYSTPLT | 18 |
| 24 | RASQGISSYLA | 1 | DASSLESGV | 6 | YCQQYGSSPLT | 19 |
| 25 | RASQGISSYLA | 1 | DASSLESGV | 6 | YCQQYYTTPLT | 20 |
| 26 | RASQGISSYLA | 1 | DASSLESGV | 6 | YCKQAYIPPLT | 21 |
| 27 | RASQGISSYLA | 1 | DASSLESGV | 6 | YCFQGSHVPRT | 22 |
| 28 | RASQGISSYLA | 1 | DASSLESGV | 6 | YCQQYYSTPLT | 23 |
| 29 | RASQGISSYLA | 1 | AASTLQSGV | 7 | HCQHYAGYSAT | 10 |
| 30 | RASQGISSYLA | 1 | AASTLQSGV | 7 | YCQQSYSTPPT | 11 |
| 31 | RASQGISSYLA | 1 | AASTLQSGV | 7 | YCQQSYSTPRT | 12 |
| 32 | RASQGISSYLA | 1 | AASTLQSGV | 7 | YCQQWSSHPQT | 13 |
| 33 | RASQGISSYLA | 1 | AASTLQSGV | 7 | YCQHHYGTPLT | 14 |
| 34 | RASQGISSYLA | 1 | AASTLQSGV | 7 | YCQQSYSTSHT | 15 |
| 35 | RASQGISSYLA | 1 | AASTLQSGV | 7 | YCQQSYSTPNT | 16 |
| 36 | RASQGISSYLA | 1 | AASTLQSGV | 7 | YCQQWSSSPLT | 17 |

TABLE 2-continued

Combinations of light chain HVR sequences

| Antibody Number | VR1 Variable Region Sequence | SEQ ID NO | VR2 Variable Region Sequence | SEQ ID NO | VR3 Variable Region Sequence | SEQ ID NO |
|---|---|---|---|---|---|---|
| 37 | RASQGISSYLA | 1 | AASTLQSGV | 7 | YCQQSYSTPLT | 18 |
| 38 | RASQGISSYLA | 1 | AASTLQSGV | 7 | YCQQYGSSPLT | 19 |
| 39 | RASQGISSYLA | 1 | AASTLQSGV | 7 | YCQQYYTTPLT | 20 |
| 40 | RASQGISSYLA | 1 | AASTLQSGV | 7 | YCKQAYIPPLT | 21 |
| 41 | RASQGISSYLA | 1 | AASTLQSGV | 7 | YCFQGSHVPRT | 22 |
| 42 | RASQGISSYLA | 1 | AASTLQSGV | 7 | YCQQYYSTPLT | 23 |
| 43 | RASQGISSYLA | 1 | DASNRATGI | 8 | HCQHYAGYSAT | 10 |
| 44 | RASQGISSYLA | 1 | DASNRATGI | 8 | YCQQSYSTPPT | 11 |
| 45 | RASQGISSYLA | 1 | DASNRATGI | 8 | YCQQSYSTPRT | 12 |
| 46 | RASQGISSYLA | 1 | DASNRATGI | 8 | YCQQWSSHPQT | 13 |
| 47 | RASQGISSYLA | 1 | DASNRATGI | 8 | YCQHHYGTPLT | 14 |
| 48 | RASQGISSYLA | 1 | DASNRATGI | 8 | YCQQSYSTSHT | 15 |
| 49 | RASQGISSYLA | 1 | DASNRATGI | 8 | YCQQSYSTPNT | 16 |
| 50 | RASQGISSYLA | 1 | DASNRATGI | 8 | YCQQWSSSPLT | 17 |
| 51 | RASQGISSYLA | 1 | DASNRATGI | 8 | YCQQSYSTPLT | 18 |
| 52 | RASQGISSYLA | 1 | DASNRATGI | 8 | YCQQYGSSPLT | 19 |
| 53 | RASQGISSYLA | 1 | DASNRATGI | 8 | YCQQYYTTPLT | 20 |
| 54 | RASQGISSYLA | 1 | DASNRATGI | 8 | YCKQAYIPPLT | 21 |
| 55 | RASQGISSYLA | 1 | DASNRATGI | 8 | YCFQGSHVPRT | 22 |
| 56 | RASQGISSYLA | 1 | DASNRATGI | 8 | YCQQYYSTPLT | 23 |
| 57 | RASQGISSYLA | 1 | DASNLETGV | 9 | HCQHYAGYSAT | 10 |
| 58 | RASQGISSYLA | 1 | DASNLETGV | 9 | YCQQSYSTPPT | 11 |
| 59 | RASQGISSYLA | 1 | DASNLETGV | 9 | YCQQSYSTPRT | 12 |
| 60 | RASQGISSYLA | 1 | DASNLETGV | 9 | YCQQWSSHPQT | 13 |
| 61 | RASQGISSYLA | 1 | DASNLETGV | 9 | YCQHHYGTPLT | 14 |
| 62 | RASQGISSYLA | 1 | DASNLETGV | 9 | YCQQSYSTSHT | 15 |
| 63 | RASQGISSYLA | 1 | DASNLETGV | 9 | YCQQSYSTPNT | 16 |
| 64 | RASQGISSYLA | 1 | DASNLETGV | 9 | YCQQWSSSPLT | 17 |
| 65 | RASQGISSYLA | 1 | DASNLETGV | 9 | YCQQSYSTPLT | 18 |
| 66 | RASQGISSYLA | 1 | DASNLETGV | 9 | YCQQYGSSPLT | 19 |
| 67 | RASQGISSYLA | 1 | DASNLETGV | 9 | YCQQYYTTPLT | 20 |
| 68 | RASQGISSYLA | 1 | DASNLETGV | 9 | YCKQAYIPPLT | 21 |
| 69 | RASQGISSYLA | 1 | DASNLETGV | 9 | YCFQGSHVPRT | 22 |
| 70 | RASQGISSYLA | 1 | DASNLETGV | 9 | YCQQYYSTPLT | 23 |
| 71 | RASQSVSSYLA | 2 | AASSLQSGV | 5 | HCQHYAGYSAT | 10 |
| 72 | RASQSVSSYLA | 2 | AASSLQSGV | 5 | YCQQSYSTPPT | 11 |

TABLE 2-continued

Combinations of light chain HVR sequences

| Antibody Number | VR1 Variable Region Sequence | SEQ ID NO | VR2 Variable Region Sequence | SEQ ID NO | VR3 Variable Region Sequence | SEQ ID NO |
|---|---|---|---|---|---|---|
| 73 | RASQSVSSYLA | 2 | AASSLQSGV | 5 | YCQQSYSTPRT | 12 |
| 74 | RASQSVSSYLA | 2 | AASSLQSGV | 5 | YCQQWSSHPQT | 13 |
| 75 | RASQSVSSYLA | 2 | AASSLQSGV | 5 | YCQHHYGTPLT | 14 |
| 76 | RASQSVSSYLA | 2 | AASSLQSGV | 5 | YCQQSYSTSHT | 15 |
| 77 | RASQSVSSYLA | 2 | AASSLQSGV | 5 | YCQQSYSTPNT | 16 |
| 78 | RASQSVSSYLA | 2 | AASSLQSGV | 5 | YCQQWSSSPLT | 17 |
| 79 | RASQSVSSYLA | 2 | AASSLQSGV | 5 | YCQQSYSTPLT | 18 |
| 80 | RASQSVSSYLA | 2 | AASSLQSGV | 5 | YCQQYGSSPLT | 19 |
| 81 | RASQSVSSYLA | 2 | AASSLQSGV | 5 | YCQQYYTTPLT | 20 |
| 82 | RASQSVSSYLA | 2 | AASSLQSGV | 5 | YCKQAYIPPLT | 21 |
| 83 | RASQSVSSYLA | 2 | AASSLQSGV | 5 | YCFQGSHVPRT | 22 |
| 84 | RASQSVSSYLA | 2 | AASSLQSGV | 5 | YCQQYYSTPLT | 23 |
| 85 | RASQSVSSYLA | 2 | DASSLESGV | 6 | HCQHYAGYSAT | 10 |
| 86 | RASQSVSSYLA | 2 | DASSLESGV | 6 | YCQQSYSTPPT | 11 |
| 87 | RASQSVSSYLA | 2 | DASSLESGV | 6 | YCQQSYSTPRT | 12 |
| 88 | RASQSVSSYLA | 2 | DASSLESGV | 6 | YCQQWSSHPQT | 13 |
| 89 | RASQSVSSYLA | 2 | DASSLESGV | 6 | YCQHHYGTPLT | 14 |
| 90 | RASQSVSSYLA | 2 | DASSLESGV | 6 | YCQQSYSTSHT | 15 |
| 91 | RASQSVSSYLA | 2 | DASSLESGV | 6 | YCQQSYSTPNT | 16 |
| 92 | RASQSVSSYLA | 2 | DASSLESGV | 6 | YCQQWSSSPLT | 17 |
| 93 | RASQSVSSYLA | 2 | DASSLESGV | 6 | YCQQSYSTPLT | 18 |
| 94 | RASQSVSSYLA | 2 | DASSLESGV | 6 | YCQQYGSSPLT | 19 |
| 95 | RASQSVSSYLA | 2 | DASSLESGV | 6 | YCQQYYTTPLT | 20 |
| 96 | RASQSVSSYLA | 2 | DASSLESGV | 6 | YCKQAYIPPLT | 21 |
| 97 | RASQSVSSYLA | 2 | DASSLESGV | 6 | YCFQGSHVPRT | 22 |
| 98 | RASQSVSSYLA | 2 | DASSLESGV | 6 | YCQQYYSTPLT | 23 |
| 99 | RASQSVSSYLA | 2 | AASTLQSGV | 7 | HCQHYAGYSAT | 10 |
| 100 | RASQSVSSYLA | 2 | AASTLQSGV | 7 | YCQQSYSTPPT | 11 |
| 101 | RASQSVSSYLA | 2 | AASTLQSGV | 7 | YCQQSYSTPRT | 12 |
| 102 | RASQSVSSYLA | 2 | AASTLQSGV | 7 | YCQQWSSHPQT | 13 |
| 103 | RASQSVSSYLA | 2 | AASTLQSGV | 7 | YCQHHYGTPLT | 14 |
| 104 | RASQSVSSYLA | 2 | AASTLQSGV | 7 | YCQQSYSTSHT | 15 |
| 105 | RASQSVSSYLA | 2 | AASTLQSGV | 7 | YCQQSYSTPNT | 16 |
| 106 | RASQSVSSYLA | 2 | AASTLQSGV | 7 | YCQQWSSSPLT | 17 |
| 107 | RASQSVSSYLA | 2 | AASTLQSGV | 7 | YCQQSYSTPLT | 18 |
| 108 | RASQSVSSYLA | 2 | AASTLQSGV | 7 | YCQQYGSSPLT | 19 |

TABLE 2-continued

Combinations of light chain HVR sequences

| Antibody Number | VR1 Variable Region Sequence | SEQ ID NO | VR2 Variable Region Sequence | SEQ ID NO | VR3 Variable Region Sequence | SEQ ID NO |
|---|---|---|---|---|---|---|
| 109 | RASQSVSSYLA | 2 | AASTLQSGV | 7 | YCQQYYTTPLT | 20 |
| 110 | RASQSVSSYLA | 2 | AASTLQSGV | 7 | YCKQAYIPPLT | 21 |
| 111 | RASQSVSSYLA | 2 | AASTLQSGV | 7 | YCFQGSHVPRT | 22 |
| 112 | RASQSVSSYLA | 2 | AASTLQSGV | 7 | YCQQYYSTPLT | 23 |
| 113 | RASQSVSSYLA | 2 | DASNRATGI | 8 | HCQHYAGYSAT | 10 |
| 114 | RASQSVSSYLA | 2 | DASNRATGI | 8 | YCQQSYSTPPT | 11 |
| 115 | RASQSVSSYLA | 2 | DASNRATGI | 8 | YCQQSYSTPRT | 12 |
| 116 | RASQSVSSYLA | 2 | DASNRATGI | 8 | YCQQWSSHPQT | 13 |
| 117 | RASQSVSSYLA | 2 | DASNRATGI | 8 | YCQHHYGTPLT | 14 |
| 118 | RASQSVSSYLA | 2 | DASNRATGI | 8 | YCQQSYSTSHT | 15 |
| 119 | RASQSVSSYLA | 2 | DASNRATGI | 8 | YCQQSYSTPNT | 16 |
| 120 | RASQSVSSYLA | 2 | DASNRATGI | 8 | YCQQWSSSPLT | 17 |
| 121 | RASQSVSSYLA | 2 | DASNRATGI | 8 | YCQQSYSTPLT | 18 |
| 122 | RASQSVSSYLA | 2 | DASNRATGI | 8 | YCQQYGSSPLT | 19 |
| 123 | RASQSVSSYLA | 2 | DASNRATGI | 8 | YCQQYYTTPLT | 20 |
| 124 | RASQSVSSYLA | 2 | DASNRATGI | 8 | YCKQAYIPPLT | 21 |
| 125 | RASQSVSSYLA | 2 | DASNRATGI | 8 | YCFQGSHVPRT | 22 |
| 126 | RASQSVSSYLA | 2 | DASNRATGI | 8 | YCQQYYSTPLT | 23 |
| 127 | RASQSVSSYLA | 2 | DASNLETGV | 9 | HCQHYAGYSAT | 10 |
| 128 | RASQSVSSYLA | 2 | DASNLETGV | 9 | YCQQSYSTPPT | 11 |
| 129 | RASQSVSSYLA | 2 | DASNLETGV | 9 | YCQQSYSTPRT | 12 |
| 130 | RASQSVSSYLA | 2 | DASNLETGV | 9 | YCQQWSSHPQT | 13 |
| 131 | RASQSVSSYLA | 2 | DASNLETGV | 9 | YCQHHYGTPLT | 14 |
| 132 | RASQSVSSYLA | 2 | DASNLETGV | 9 | YCQQSYSTSHT | 15 |
| 133 | RASQSVSSYLA | 2 | DASNLETGV | 9 | YCQQSYSTPNT | 16 |
| 134 | RASQSVSSYLA | 2 | DASNLETGV | 9 | YCQQWSSSPLT | 17 |
| 135 | RASQSVSSYLA | 2 | DASNLETGV | 9 | YCQQSYSTPLT | 18 |
| 136 | RASQSVSSYLA | 2 | DASNLETGV | 9 | YCQQYGSSPLT | 19 |
| 137 | RASQSVSSYLA | 2 | DASNLETGV | 9 | YCQQYYTTPLT | 20 |
| 138 | RASQSVSSYLA | 2 | DASNLETGV | 9 | YCKQAYIPPLT | 21 |
| 139 | RASQSVSSYLA | 2 | DASNLETGV | 9 | YCFQGSHVPRT | 22 |
| 140 | RASQSVSSYLA | 2 | DASNLETGV | 9 | YCQQYYSTPLT | 23 |
| 141 | RASQGVSSYLA | 3 | AASSLQSGV | 5 | HCQHYAGYSAT | 10 |
| 142 | RASQGVSSYLA | 3 | AASSLQSGV | 5 | YCQQSYSTPPT | 11 |
| 143 | RASQGVSSYLA | 3 | AASSLQSGV | 5 | YCQQSYSTPRT | 12 |
| 144 | RASQGVSSYLA | 3 | AASSLQSGV | 5 | YCQQWSSHPQT | 13 |

TABLE 2-continued

| Combinations of light chain HVR sequences | | | | | | |
|---|---|---|---|---|---|---|
| | VR1 Variable Region | | VR2 Variable Region | | VR3 Variable Region | |
| Antibody Number | Sequence | SEQ ID NO | Sequence | SEQ ID NO | Sequence | SEQ ID NO |
| 145 | RASQGVSSYLA | 3 | AASSLQSGV | 5 | YCQHHYGTPLT | 14 |
| 146 | RASQGVSSYLA | 3 | AASSLQSGV | 5 | YCQQSYSTSHT | 15 |
| 147 | RASQGVSSYLA | 3 | AASSLQSGV | 5 | YCQQSYSTPNT | 16 |
| 148 | RASQGVSSYLA | 3 | AASSLQSGV | 5 | YCQQWSSSPLT | 17 |
| 149 | RASQGVSSYLA | 3 | AASSLQSGV | 5 | YCQQSYSTPLT | 18 |
| 150 | RASQGVSSYLA | 3 | AASSLQSGV | 5 | YCQQYGSSPLT | 19 |
| 151 | RASQGVSSYLA | 3 | AASSLQSGV | 5 | YCQQYYTTPLT | 20 |
| 152 | RASQGVSSYLA | 3 | AASSLQSGV | 5 | YCKQAYIPPLT | 21 |
| 153 | RASQGVSSYLA | 3 | AASSLQSGV | 5 | YCFQGSHVPRT | 22 |
| 154 | RASQGVSSYLA | 3 | AASSLQSGV | 5 | YCQQYYSTPLT | 23 |
| 155 | RASQGVSSYLA | 3 | DASSLESGV | 6 | HCQHYAGYSAT | 10 |
| 156 | RASQGVSSYLA | 3 | DASSLESGV | 6 | YCQQSYSTPPT | 11 |
| 157 | RASQGVSSYLA | 3 | DASSLESGV | 6 | YCQQSYSTPRT | 12 |
| 158 | RASQGVSSYLA | 3 | DASSLESGV | 6 | YCQQWSSHPQT | 13 |
| 159 | RASQGVSSYLA | 3 | DASSLESGV | 6 | YCQHHYGTPLT | 14 |
| 160 | RASQGVSSYLA | 3 | DASSLESGV | 6 | YCQQSYSTSHT | 15 |
| 161 | RASQGVSSYLA | 3 | DASSLESGV | 6 | YCQQSYSTPNT | 16 |
| 162 | RASQGVSSYLA | 3 | DASSLESGV | 6 | YCQQWSSSPLT | 17 |
| 163 | RASQGVSSYLA | 3 | DASSLESGV | 6 | YCQQSYSTPLT | 18 |
| 164 | RASQGVSSYLA | 3 | DASSLESGV | 6 | YCQQYGSSPLT | 19 |
| 165 | RASQGVSSYLA | 3 | DASSLESGV | 6 | YCQQYYTTPLT | 20 |
| 166 | RASQGVSSYLA | 3 | DASSLESGV | 6 | YCKQAYIPPLT | 21 |
| 167 | RASQGVSSYLA | 3 | DASSLESGV | 6 | YCFQGSHVPRT | 22 |
| 168 | RASQGVSSYLA | 3 | DASSLESGV | 6 | YCQQYYSTPLT | 23 |
| 169 | RASQGVSSYLA | 3 | AASTLQSGV | 7 | HCQHYAGYSAT | 10 |
| 170 | RASQGVSSYLA | 3 | AASTLQSGV | 7 | YCQQSYSTPPT | 11 |
| 171 | RASQGVSSYLA | 3 | AASTLQSGV | 7 | YCQQSYSTPRT | 12 |
| 172 | RASQGVSSYLA | 3 | AASTLQSGV | 7 | YCQQWSSHPQT | 13 |
| 173 | RASQGVSSYLA | 3 | AASTLQSGV | 7 | YCQHHYGTPLT | 14 |
| 174 | RASQGVSSYLA | 3 | AASTLQSGV | 7 | YCQQSYSTSHT | 15 |
| 175 | RASQGVSSYLA | 3 | AASTLQSGV | 7 | YCQQSYSTPNT | 16 |
| 176 | RASQGVSSYLA | 3 | AASTLQSGV | 7 | YCQQWSSSPLT | 17 |
| 177 | RASQGVSSYLA | 3 | AASTLQSGV | 7 | YCQQSYSTPLT | 18 |
| 178 | RASQGVSSYLA | 3 | AASTLQSGV | 7 | YCQQYGSSPLT | 19 |
| 179 | RASQGVSSYLA | 3 | AASTLQSGV | 7 | YCQQYYTTPLT | 20 |
| 180 | RASQGVSSYLA | 3 | AASTLQSGV | 7 | YCKQAYIPPLT | 21 |

TABLE 2-continued

Combinations of light chain HVR sequences

| | VR1 Variable Region | | VR2 Variable Region | | VR3 Variable Region | |
|---|---|---|---|---|---|---|
| Antibody Number | Sequence | SEQ ID NO | Sequence | SEQ ID NO | Sequence | SEQ ID NO |
| 181 | RASQGVSSYLA | 3 | AASTLQSGV | 7 | YCFQGSHVPRT | 22 |
| 182 | RASQGVSSYLA | 3 | AASTLQSGV | 7 | YCQQYYSTPLT | 23 |
| 183 | RASQGVSSYLA | 3 | DASNRATGI | 8 | HCQHYAGYSAT | 10 |
| 184 | RASQGVSSYLA | 3 | DASNRATGI | 8 | YCQQSYSTPPT | 11 |
| 185 | RASQGVSSYLA | 3 | DASNRATGI | 8 | YCQQSYSTPRT | 12 |
| 186 | RASQGVSSYLA | 3 | DASNRATGI | 8 | YCQQWSSHPQT | 13 |
| 187 | RASQGVSSYLA | 3 | DASNRATGI | 8 | YCQHHYGTPLT | 14 |
| 188 | RASQGVSSYLA | 3 | DASNRATGI | 8 | YCQQSYSTSHT | 15 |
| 189 | RASQGVSSYLA | 3 | DASNRATGI | 8 | YCQQSYSTPNT | 16 |
| 190 | RASQGVSSYLA | 3 | DASNRATGI | 8 | YCQQWSSSPLT | 17 |
| 191 | RASQGVSSYLA | 3 | DASNRATGI | 8 | YCQQSYSTPLT | 18 |
| 192 | RASQGVSSYLA | 3 | DASNRATGI | 8 | YCQQYGSSPLT | 19 |
| 193 | RASQGVSSYLA | 3 | DASNRATGI | 8 | YCQQYYTTPLT | 20 |
| 194 | RASQGVSSYLA | 3 | DASNRATGI | 8 | YCKQAYIPPLT | 21 |
| 195 | RASQGVSSYLA | 3 | DASNRATGI | 8 | YCFQGSHVPRT | 22 |
| 196 | RASQGVSSYLA | 3 | DASNRATGI | 8 | YCQQYYSTPLT | 23 |
| 197 | RASQGVSSYLA | 3 | DASNLETGV | 9 | HCQHYAGYSAT | 10 |
| 198 | RASQGVSSYLA | 3 | DASNLETGV | 9 | YCQQSYSTPPT | 11 |
| 199 | RASQGVSSYLA | 3 | DASNLETGV | 9 | YCQQSYSTPRT | 12 |
| 200 | RASQGVSSYLA | 3 | DASNLETGV | 9 | YCQQWSSHPQT | 13 |
| 201 | RASQGVSSYLA | 3 | DASNLETGV | 9 | YCQHHYGTPLT | 14 |
| 202 | RASQGVSSYLA | 3 | DASNLETGV | 9 | YCQQSYSTSHT | 15 |
| 203 | RASQGVSSYLA | 3 | DASNLETGV | 9 | YCQQSYSTPNT | 16 |
| 204 | RASQGVSSYLA | 3 | DASNLETGV | 9 | YCQQWSSSPLT | 17 |
| 205 | RASQGVSSYLA | 3 | DASNLETGV | 9 | YCQQSYSTPLT | 18 |
| 206 | RASQGVSSYLA | 3 | DASNLETGV | 9 | YCQQYGSSPLT | 19 |
| 207 | RASQGVSSYLA | 3 | DASNLETGV | 9 | YCQQYYTTPLT | 20 |
| 208 | RASQGVSSYLA | 3 | DASNLETGV | 9 | YCKQAYIPPLT | 21 |
| 209 | RASQGVSSYLA | 3 | DASNLETGV | 9 | YCFQGSHVPRT | 22 |
| 210 | RASQGVSSYLA | 3 | DASNLETGV | 9 | YCQQYYSTPLT | 23 |
| 211 | RASQSISSYLN | 4 | AASSLQSGV | 5 | HCQHYAGYSAT | 10 |
| 212 | RASQSISSYLN | 4 | AASSLQSGV | 5 | YCQQSYSTPPT | 11 |
| 213 | RASQSISSYLN | 4 | AASSLQSGV | 5 | YCQQSYSTPRT | 12 |
| 214 | RASQSISSYLN | 4 | AASSLQSGV | 5 | YCQQWSSHPQT | 13 |
| 215 | RASQSISSYLN | 4 | AASSLQSGV | 5 | YCQHHYGTPLT | 14 |
| 216 | RASQSISSYLN | 4 | AASSLQSGV | 5 | YCQQSYSTSHT | 15 |

TABLE 2-continued

Combinations of light chain HVR sequences

| Antibody Number | VR1 Variable Region Sequence | SEQ ID NO | VR2 Variable Region Sequence | SEQ ID NO | VR3 Variable Region Sequence | SEQ ID NO |
|---|---|---|---|---|---|---|
| 217 | RASQSISSYLN | 4 | AASSLQSGV | 5 | YCQQSYSTPNT | 16 |
| 218 | RASQSISSYLN | 4 | AASSLQSGV | 5 | YCQQWSSSPLT | 17 |
| 219 | RASQSISSYLN | 4 | AASSLQSGV | 5 | YCQQSYSTPLT | 18 |
| 220 | RASQSISSYLN | 4 | AASSLQSGV | 5 | YCQQYGSSPLT | 19 |
| 221 | RASQSISSYLN | 4 | AASSLQSGV | 5 | YCQQYYTTPLT | 20 |
| 222 | RASQSISSYLN | 4 | AASSLQSGV | 5 | YCKQAYIPPLT | 21 |
| 223 | RASQSISSYLN | 4 | AASSLQSGV | 5 | YCFQGSHVPRT | 22 |
| 224 | RASQSISSYLN | 4 | AASSLQSGV | 5 | YCQQYYSTPLT | 23 |
| 225 | RASQSISSYLN | 4 | DASSLESGV | 6 | HCQHYAGYSAT | 10 |
| 226 | RASQSISSYLN | 4 | DASSLESGV | 6 | YCQQSYSTPPT | 11 |
| 227 | RASQSISSYLN | 4 | DASSLESGV | 6 | YCQQSYSTPRT | 12 |
| 228 | RASQSISSYLN | 4 | DASSLESGV | 6 | YCQQWSSHPQT | 13 |
| 229 | RASQSISSYLN | 4 | DASSLESGV | 6 | YCQHHYGTPLT | 14 |
| 230 | RASQSISSYLN | 4 | DASSLESGV | 6 | YCQQSYSTSHT | 15 |
| 231 | RASQSISSYLN | 4 | DASSLESGV | 6 | YCQQSYSTPNT | 16 |
| 232 | RASQSISSYLN | 4 | DASSLESGV | 6 | YCQQWSSSPLT | 17 |
| 233 | RASQSISSYLN | 4 | DASSLESGV | 6 | YCQQSYSTPLT | 18 |
| 234 | RASQSISSYLN | 4 | DASSLESGV | 6 | YCQQYGSSPLT | 19 |
| 235 | RASQSISSYLN | 4 | DASSLESGV | 6 | YCQQYYTTPLT | 20 |
| 236 | RASQSISSYLN | 4 | DASSLESGV | 6 | YCKQAYIPPLT | 21 |
| 237 | RASQSISSYLN | 4 | DASSLESGV | 6 | YCFQGSHVPRT | 22 |
| 238 | RASQSISSYLN | 4 | DASSLESGV | 6 | YCQQYYSTPLT | 23 |
| 239 | RASQSISSYLN | 4 | AASTLQSGV | 7 | HCQHYAGYSAT | 10 |
| 240 | RASQSISSYLN | 4 | AASTLQSGV | 7 | YCQQSYSTPPT | 11 |
| 241 | RASQSISSYLN | 4 | AASTLQSGV | 7 | YCQQSYSTPRT | 12 |
| 242 | RASQSISSYLN | 4 | AASTLQSGV | 7 | YCQQWSSHPQT | 13 |
| 243 | RASQSISSYLN | 4 | AASTLQSGV | 7 | YCQHHYGTPLT | 14 |
| 244 | RASQSISSYLN | 4 | AASTLQSGV | 7 | YCQQSYSTSHT | 15 |
| 245 | RASQSISSYLN | 4 | AASTLQSGV | 7 | YCQQSYSTPNT | 16 |
| 246 | RASQSISSYLN | 4 | AASTLQSGV | 7 | YCQQWSSSPLT | 17 |
| 247 | RASQSISSYLN | 4 | AASTLQSGV | 7 | YCQQSYSTPLT | 18 |
| 248 | RASQSISSYLN | 4 | AASTLQSGV | 7 | YCQQYGSSPLT | 19 |
| 249 | RASQSISSYLN | 4 | AASTLQSGV | 7 | YCQQYYTTPLT | 20 |
| 250 | RASQSISSYLN | 4 | AASTLQSGV | 7 | YCKQAYIPPLT | 21 |
| 251 | RASQSISSYLN | 4 | AASTLQSGV | 7 | YCFQGSHVPRT | 22 |
| 252 | RASQSISSYLN | 4 | AASTLQSGV | 7 | YCQQYYSTPLT | 23 |

TABLE 2-continued

Combinations of light chain HVR sequences

| Antibody Number | VR1 Variable Region Sequence | SEQ ID NO | VR2 Variable Region Sequence | SEQ ID NO | VR3 Variable Region Sequence | SEQ ID NO |
|---|---|---|---|---|---|---|
| 253 | RASQSISSYLN | 4 | DASNRATGI | 8 | HCQHYAGYSAT | 10 |
| 254 | RASQSISSYLN | 4 | DASNRATGI | 8 | YCQQSYSTPPT | 11 |
| 255 | RASQSISSYLN | 4 | DASNRATGI | 8 | YCQQSYSTPRT | 12 |
| 256 | RASQSISSYLN | 4 | DASNRATGI | 8 | YCQQWSSHPQT | 13 |
| 257 | RASQSISSYLN | 4 | DASNRATGI | 8 | YCQHHYGTPLT | 14 |
| 258 | RASQSISSYLN | 4 | DASNRATGI | 8 | YCQQSYSTSHT | 15 |
| 259 | RASQSISSYLN | 4 | DASNRATGI | 8 | YCQQSYSTPNT | 16 |
| 260 | RASQSISSYLN | 4 | DASNRATGI | 8 | YCQQWSSSPLT | 17 |
| 261 | RASQSISSYLN | 4 | DASNRATGI | 8 | YCQQSYSTPLT | 18 |
| 262 | RASQSISSYLN | 4 | DASNRATGI | 8 | YCQQYGSSPLT | 19 |
| 263 | RASQSISSYLN | 4 | DASNRATGI | 8 | YCQQYYTTPLT | 20 |
| 264 | RASQSISSYLN | 4 | DASNRATGI | 8 | YCKQAYIPPLT | 21 |
| 265 | RASQSISSYLN | 4 | DASNRATGI | 8 | YCFQGSHVPRT | 22 |
| 266 | RASQSISSYLN | 4 | DASNRATGI | 8 | YCQQYYSTPLT | 23 |
| 267 | RASQSISSYLN | 4 | DASNLETGV | 9 | HCQHYAGYSAT | 10 |
| 268 | RASQSISSYLN | 4 | DASNLETGV | 9 | YCQQSYSTPPT | 11 |
| 269 | RASQSISSYLN | 4 | DASNLETGV | 9 | YCQQSYSTPRT | 12 |
| 270 | RASQSISSYLN | 4 | DASNLETGV | 9 | YCQQWSSHPQT | 13 |
| 271 | RASQSISSYLN | 4 | DASNLETGV | 9 | YCQHHYGTPLT | 14 |
| 272 | RASQSISSYLN | 4 | DASNLETGV | 9 | YCQQSYSTSHT | 15 |
| 273 | RASQSISSYLN | 4 | DASNLETGV | 9 | YCQQSYSTPNT | 16 |
| 274 | RASQSISSYLN | 4 | DASNLETGV | 9 | YCQQWSSSPLT | 17 |
| 275 | RASQSISSYLN | 4 | DASNLETGV | 9 | YCQQSYSTPLT | 18 |
| 276 | RASQSISSYLN | 4 | DASNLETGV | 9 | YCQQYGSSPLT | 19 |
| 277 | RASQSISSYLN | 4 | DASNLETGV | 9 | YCQQYYTTPLT | 20 |
| 278 | RASQSISSYLN | 4 | DASNLETGV | 9 | YCKQAYIPPLT | 21 |
| 279 | RASQSISSYLN | 4 | DASNLETGV | 9 | YCFQGSHVPRT | 22 |
| 280 | RASQSISSYLN | 4 | DASNLETGV | 9 | YCQQYYSTPLT | 23 |

In some embodiments, provided herein is an antibody light chain with a light chain variable region comprising a HVR-L1, a HVR-L2 and a HVR-L3 of the present disclosure. In some embodiments, at least two of the HVR-L1, HVR-L2, and HVR-L3 comprise an amino acid sequence selected from a HVR-L1 sequence of the present disclosure (e.g., SEQ ID NOS:1-4), a HVR-L2 sequence of the present disclosure (e.g., SEQ ID NOS:5-9), and a HVR-L3 sequence of the present disclosure (e.g., SEQ ID NOS: 10-23).

The light chain HVR sequences described herein may be included in any combination in an antibody light chain or light chain variable region of the present disclosure. In some embodiments, a light chain variable region comprises a HVR-L2 comprising an amino acid sequence selected from the group consisting of SEQ ID NOS:5-9 and a HVR-L3 of the antibody comprising an amino acid sequence selected from the group consisting of SEQ ID NOS:10-23. In some embodiments, a light chain variable region comprises a HVR-L1 comprising an amino acid sequence selected from the group consisting of SEQ ID NOS:1-4 and a HVR-L2 of the antibody comprises an amino acid sequence selected from the group consisting of SEQ ID NOS:5-9. In some embodiments, a light chain variable region comprises a HVR-L1 comprising an amino acid sequence selected from the group consisting of SEQ ID NOS:1-4 and a HVR-L3 of the antibody comprising an amino acid sequence selected from the group consisting of SEQ ID NOS:10-23. In some embodiments, a light chain variable region comprises a HVR-L1 comprising an amino acid sequence selected from the group consisting of SEQ ID NOS:1-4, a HVR-L2 comprising an amino acid sequence selected from the group consisting of SEQ ID NOS:5-9, and a HVR-L3 comprising an amino acid sequence selected from the group consisting of SEQ ID NOS:10-23. In certain embodiments, a light chain variable region comprises three of a HVR-L1, a HVR-L2, and a HVR-L3 selected from the group consisting of: a HVR-L1 comprising the amino acid sequence of SEQ ID NO:1, a HVR-L2 comprising the amino acid sequence of SEQ ID NO:9, and a HVR-L3 comprising an amino acid sequence selected from the group consisting of SEQ ID NOS:10-23; a HVR-L1 comprising the amino acid sequence of SEQ ID NO:2, a HVR-L2 comprising an amino acid sequence selected from the group consisting of SEQ ID NOS:5-9, and a HVR-L3 comprising the amino acid sequence of SEQ ID NO:18; a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NOS: 23; a HVR-L1 comprising the amino acid sequence of SEQ ID NO:1, a HVR-L2 comprising an amino acid sequence selected from the group consisting of SEQ ID NOS:5-9, and a HVR-L3 sequence comprising the amino acid sequence of SEQ ID NOS:20; a HVR-L1 selected from the group consisting of SEQ ID NOS:1-4, a HVR-L2 comprising the amino acid sequence of SEQ ID NO:9, and a HVR-L3 comprising the amino acid sequence of SEQ ID NOS:18; a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:23; a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:20; a HVR-L1 comprising the amino acid sequence of SEQ ID NO:3, a HVR-L2 comprising the amino acid sequence of SEQ ID NO:9, and a HVR-L3 comprising an amino acid sequence selected from the group consisting of SEQ ID NOS:10-23; a HVR-L1 comprising the amino acid sequence of SEQ ID NO:4, a HVR-L2 comprising the amino acid sequence of SEQ ID NO:6, and a HVR-L3 comprising an amino acid sequence selected from the group consisting of SEQ ID NOS:10-23; a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:23; a HVR-L1 comprising the amino acid sequence of SEQ ID NO:4, a HVR-L2 comprising an amino acid sequence selected from the group consisting of SEQ ID NOS:5-9, and a HVR-L3 comprising the amino acid sequence of SEQ ID NO:14; a HVR-L1 comprising the amino acid sequence of SEQ ID NO:1, a HVR-L2 comprising an amino acid sequence selected from the group consisting of SEQ ID NOS:5-9, and a HVR-L3 comprising the amino acid sequence of SEQ ID NO:18; a HVR-L1 comprising the amino acid sequence of SEQ ID NO:3, a HVR-L2 comprising an amino acid sequence selected from the group consisting of SEQ ID NOS:5-9, and a HVR-L3 comprising the amino acid sequence of SEQ ID NO:20; a HVR-L1 comprising an amino acid sequence selected from the group consisting of SEQ ID NOS:1-4, a HVR-L2 comprising the amino acid sequence of SEQ ID NO:9, and a HVR-L3 comprising the amino acid sequence of SEQ ID NO:14; a HVR-L1 comprising an amino acid sequence selected from the group consisting of SEQ ID NOS:1-4, a HVR-L2 comprising the amino acid sequence of SEQ ID NO:6, and a HVR-L3 comprising the amino acid sequence of SEQ ID NO:23; and a HVR-L1 comprising an amino acid sequence selected from the group consisting of SEQ ID NOS:1-4, a HVR-L2 comprising the amino acid sequence of SEQ ID NO:7, and a HVR-L3 comprising the amino acid sequence of SEQ ID NO:23. In certain embodiments, a light chain variable region comprises three of a HVR-L1, a HVR-L2, and a HVR-L3 selected from the group consisting of: a HVR-L1 comprising the amino acid sequence of SEQ ID NO:2, a HVR-L2 comprising the amino acid sequence of SEQ ID NO:9, and a HVR-L3 comprising the amino acid sequence of SEQ ID NO:18; a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:23; a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:20; a HVR-L1 comprising the amino acid sequence of SEQ ID NO:4, a HVR-L2 comprising the amino acid sequence of SEQ ID NO:9, and a HVR-L3 comprising the amino acid sequence of SEQ ID NO:14; a HVR-L1 comprising the amino acid sequence of SEQ ID NO:3, a HVR-L2 comprising the amino acid sequence of SEQ ID NO:9, and a HVR-L3 comprising the amino acid sequence of SEQ ID NO:20; a HVR-L1 comprising the amino acid sequence of SEQ ID NO:1, a HVR-L2 comprising the amino acid sequence of SEQ ID NO:9, and a HVR-L3 comprising the amino acid sequence of SEQ ID NO:18; a HVR-L1 comprising the amino acid sequence of SEQ ID NO:4, a HVR-L2 comprising the amino acid sequence of SEQ ID NO:7, and a HVR-L3 comprising the amino acid sequence of SEQ ID NO:23; a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:23; and a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO:17; a HVR-L1 comprising the amino acid sequence of SEQ ID NO:4, a HVR-L2 comprising the amino acid sequence of SEQ ID NO:6, and a HVR-L3 comprising the amino acid sequence of SEQ ID NO: 17; a HVR-L1 comprising the amino acid sequence of SEQ ID NO: 4, a HVR-L2 comprising an amino acid sequence of SEQ ID NO:5, and a HVR-L3 comprising an amino acid sequence of SEQ ID NO: 20; and a HVR-L1 comprising an amino acid sequence of SEQ ID NO: 4, a HVR-L2 comprising the amino acid sequence of SEQ ID NO: 8, and a HVR-L3 comprising an amino acid sequence of SEQ ID NO:11. In some embodiments, a light chain variable region comprises three of a HVR-L1, a HVR-L2, and a HVR-L3 of an antibody listed in Table 2. In some embodiments, a light chain variable region comprises three of a HVR-L1, a HVR-L2, and a HVR-L3 listed in Table 1. In some embodiments, a light chain variable region comprises a sequence selected from SEQ ID NOS:28-50.

In some embodiments, a light chain variable region further comprises variable region light chain framework sequences juxtaposed between the HVRs according to the formula: (FW-L1)-(HVR-L1)-(FW-L2)-(HVR-L2)-(FW-L3)-(HVR-L3)-(FW-L4). In some embodiments, one, two, three, or four of the framework sequences is/are the following:

```
                                      (SEQ ID NO: 24)
FW-L1 is
DIQLTQSPSSLSASVGDRVTITC

                                      (SEQ ID NO: 25)
FW-L2 is
WYQQKPGKAPKLLIY

                                      (SEQ ID NO: 26)
FW-L3 is
PSRFSGSGSGTDFTLTISSLQPEDFATY

                                     (SEQ ID  NO: 27)
FW-L4 is
FGQGTKVEIKR.
```

In some embodiments, further provided herein is an antibody comprising a heavy chain and a light chain, where the light chain includes a light chain variable region of the present disclosure. In some embodiments, further provided herein is an antibody fragment or scFv comprising a heavy chain variable region and a light chain variable region of the present disclosure.

In some embodiments, an antibody or antibody fragment of the present disclosure binds at least 1 target (e.g., a target protein or an epitope) or at least two targets with particular binding affinities. For example, in some embodiments, an antibody or antibody fragment of the present disclosure binds at least 1 target or at least two targets with an equilibrium dissociation constant (Kd) of about $10^{-7}$ M or less, $10^{-8}$ M or less, $10^{-9}$ M or less, $10^{-10}$ M or less, or $10^{-11}$ M or less. In some embodiments, an antibody or antibody fragment of the present disclosure binds at least 1 target or at least two targets with an equilibrium dissociation constant (Kd) of between about $10^{-7}$ and about $10^{-11}$ M. Exemplary assays for determining binding affinity are described and exemplified infra.

Antibodies of the present disclosure may be produced using recombinant methods and compositions, e.g., as described in U.S. Pat. No. 4,816,567. In some embodiments, isolated nucleic acids encoding any antibody described herein are provided. Such nucleic acids may encode an amino acid sequence comprising the VL and/or an amino acid sequence comprising the VH of the antibodies (e.g., the light and/or heavy chains of the antibodies). In some embodiments, one or more vectors (e.g., expression vectors or display vectors) comprising such nucleic acids are provided herein. In some embodiments, a host cell comprising such nucleic acids is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g. a Chinese Hamster Ovary (CHO) cell or lymphoid cell (e.g., Y0, NS0, Sp20 cell). In some embodiments, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of antibodies of the present disclosure, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and may be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFW CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

Bispecific Antibodies with Identical/Common/Single Light Chain

Further provided herein is a bispecific antibody having an identical light chain variable region of the present disclosure (e.g., having two heavy chain variable regions with different binding specificities and two identical light chain variable regions). In some embodiments, the bispecific antibody comprises two antibody heavy chain variable regions and two identical light chain variable regions, where the bispecific antibody includes: a first binding domain that binds to a first target or antigen and comprises a first antibody heavy chain variable region and a first light chain variable region; and a second binding domain that binds to a second target or antigen and comprises a second antibody heavy chain variable region and a second antibody light chain variable region; where the second antibody light chain variable region has a sequence identical to the first antibody light chain variable region sequence. In some embodiments, the first and second binding domain bind to different target biomolecules. In some embodiment, the first and second binding domain bind to different epitopes on a same biomolecule. In some embodiments, the first antibody heavy chain variable region is part of a first antibody heavy chain comprising the first heavy chain variable region and a first heavy chain constant region (e.g., comprising CH1, hinge, CH2 and CH3). In some embodiments, the second antibody heavy chain variable region is part of a second antibody heavy chain comprising the second heavy chain variable region and a second heavy chain constant region (e.g., comprising CH1, hinge, CH2 and CH3). In some embodiments, the first antibody light chain variable region is part of a first antibody light chain comprising the first light chain variable region and a first light chain constant region. In some embodiments, the second antibody light chain variable region is part of a second antibody light chain comprising the second light chain variable region and a second light chain constant region. In some embodiments, the first and the second antibody light chains have sequences identical to a light chain of the present disclosure.

Further provided herein is a method of generating a bispecific antibody having an identical light chain variable region of the present disclosure (e.g., having two heavy chain variable regions with different binding specificities and two identical light chain variable regions). In some embodiments, the method includes selecting a first antigen binding domain that binds to a first antigen and comprises a first antibody heavy chain variable region and a first light chain variable region of the present disclosure; (b) selecting a second antigen binding domain that binds to a second antigen and comprises a second antibody heavy chain variable region of the present disclosure, where the second antibody light chain variable region has a sequence identical to the first antibody light chain variable region sequence; and (c) producing the bispecific antibody comprising a heavy chain variable region comprising the amino acid sequence of the first antibody heavy chain variable region, a heavy chain variable region comprising the amino acid sequence of the second antibody heavy chain variable region, a light chain variable region comprising the amino acid sequence of the first antibody light chain variable region sequence, and a light chain variable region comprising the amino acid sequence of the second antibody light chain variable region sequence. In some embodiments, the first light chain variable region is encoded by a polynucleotide from a library of the present disclosure.

In some embodiments, bispecific antibodies described herein may have additional specificities. For example, one of the antigen or target binding site of the bispecific antibody may binds to more than one target specifically.

Methods for making/generating bispecific antibodies are known in the art. Production of full length bispecific antibodies can be based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

One approach known in the art for making bispecific antibodies is the "knobs-into-holes" or "protuberance-into-cavity" approach (see, e.g., U.S. Pat. No. 5,731,168). In this approach, two immunoglobulin polypeptides (e.g., heavy chain polypeptides) each comprise an interface. An interface of one immunoglobulin polypeptide interacts with a corresponding interface on the other immunoglobulin polypeptide, thereby allowing the two immunoglobulin polypeptides to associate. These interfaces may be engineered such that a "knob" or "protuberance" (these terms may be used interchangeably herein) located in the interface of one immunoglobulin polypeptide corresponds with a "hole" or "cavity" (these terms may be used interchangeably herein) located in the interface of the other immunoglobulin polypeptide. In some embodiments, the hole is of identical or similar size to the knob and suitably positioned such that when the two interfaces interact, the knob of one interface is positionable in the corresponding hole of the other interface. Without wishing to be bound to theory, this is thought to stabilize the heteromultimer and favor formation of the heteromultimer over other species, for example homomultimers. In some embodiments, this approach may be used to promote the heteromultimerization of two different immunoglobulin polypeptides, creating a bispecific antibody comprising two immunoglobulin polypeptides with binding specificities for different epitopes.

In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. For example, knobs or holes may be introduced synthetically by altering the nucleic acid sequence encoding the interface to replace at least one "original" amino acid residue with at least one "import" amino acid residue. Methods for altering nucleic acid sequences may include standard molecular biology techniques well known in the art. In some embodiments, original residues have a small side chain volume (e.g., alanine, asparagine, aspartic acid, glycine, serine, threonine, or valine), and import residues for forming a knob are naturally occurring amino acids and may include arginine, phenylalanine, tyrosine, and tryptophan. In some embodiments, original residues have a large side chain volume (e.g., arginine, phenylalanine, tyrosine, and tryptophan), and import residues for forming a hole are naturally occurring amino acids and may include alanine, serine, threonine, and valine.

In some embodiments, original residues for forming a knob or hole are identified based on the three-dimensional structure of the heteromultimer or homomultimer (e.g. homodimer). Techniques known in the art for obtaining a three-dimensional structure may include X-ray crystallography and NMR. In some embodiments, the interface is the CH3 domain of an immunoglobulin (e.g., IgG1, IgG2, IgG3, IgG4) constant domain. In these embodiments, the CH3/CH3 interface of human $IgG_1$ involves sixteen residues on each domain located on four anti-parallel β-strands. Without wishing to be bound to theory, mutated residues are preferably located on the two central anti-parallel β-strands to minimize the risk that knobs can be accommodated by the surrounding solvent, rather than the compensatory holes in the partner CH3 domain. In some embodiments, the mutations forming corresponding knobs and holes in two immunoglobulin polypeptides correspond to one or more pairs provided in the following table.

TABLE 3

Exemplary sets of corresponding knob-and hole-forming mutations

| CH3 of first immunoglobulin | CH3 of second immunoglobulin |
|---|---|
| T366Y | Y407T |
| T366W | Y407A |
| F405A | T394W |
| Y407T | T366Y |
| T366Y:F405A | T394W:Y407T |
| T366W:F405W | T394S:Y407A |
| F405W:Y407A | T366W:T394S |
| F405W | T394S |

Mutations are denoted by the original residue, followed by the position using the Kabat numbering system, and then the import residue (all residues are given in single-letter aminoacid code). Multiple mutations are separated by a colon.

In some embodiments, an immunoglobulin polypeptide comprises a CH3 domain comprising one or more amino acid substitutions listed in Table 3 above. In some embodiments, a bispecific antibody comprises a first immunoglobulin polypeptide comprising a CH3 domain comprising one or more amino acid substitutions listed in the left column of Table 3, and a second immunoglobulin polypeptide comprising a CH3 domain comprising one or more corresponding amino acid substitutions listed in the right column of Table 3.

Following mutation of the DNA as discussed above, polynucleotides encoding modified immunoglobulin polypeptides with one or more corresponding knob- or hole-forming mutations may be expressed and purified using standard recombinant techniques and cell systems known in the art. See, e.g., U.S. Pat. Nos. 5,731,168; 5,807,706; 5,821,333; 7,642,228; 7,695,936; 8,216,805; U.S. Pub. No. 2013/0089553; and Spiess et al., Nature Biotechnology 31: 753-758, 2013. Modified immunoglobulin polypeptides may be produced using prokaryotic host cells, such as *E. coli*, or eukaryotic host cells, such as CHO cells. Corresponding knob- and hole-bearing immunoglobulin polypeptides may be expressed in host cells in co-culture and purified together as a heteromultimer, or they may be expressed in single cultures, separately purified, and assembled in vitro. In some embodiments, two strains of bacterial host cells (one expressing an immunoglobulin polypeptide with a knob, and the other expressing an immunoglobulin polypeptide with a hole) are co-cultured using standard bacterial culturing techniques known in the art. In some embodiments, the two strains may be mixed in a specific ratio, e.g., so as to achieve equal expression levels in culture. In some embodiments, the two strains may be mixed in a 50:50, 60:40, or 70:30 ratio. After polypeptide expression, the cells may be lysed together, and protein may be extracted. Standard techniques known in the art that allow for measuring the abundance of homo-multimeric vs. hetero-multimeric species may include size exclusion chromatography. In some embodiments, each modified immunoglobulin polypeptide is expressed separately using standard recombinant techniques, and they may be assembled together in vitro. Assembly may be achieved, for example, by purifying each modified immunoglobulin polypeptide, mixing and incubating them together in equal mass, reducing disulfides (e.g., by treating with dithiothreitol), concentrating, and reoxidizing the polypeptides. Formed bispecific antibodies may be purified using standard techniques including cation-exchange chromatography and measured using standard techniques including size exclusion chromatography. For a more detailed description of these methods, see Speiss et al., *Nat Biotechnol* 31:753-8, 2013. In some embodiments, modified immunoglobulin polypeptides may be expressed separately in CHO cells and assembled in vitro using the methods described above.

V. Kits

In another aspect, provided herein is a kit comprising a library of polynucleotides of the present disclosure. In some embodiments, the kit further comprises a package insert comprising instructions for expressing, modifying, screening, or otherwise using the library, e.g., to identify an antibody HVR or variable region of interest. In some embodiments, the kit further comprises one or more buffers, e.g., for storing, transferring, transfecting, or otherwise using one or more of the polynucleotides (e.g., synthetic polynucleotides). In some embodiments, the kit further comprises one or more containers for storing one or more of the polynucleotides. In some embodiments, the kit further comprises one or more vectors, e.g., for transfection of a host cell with one or more of the polynucleotides.

EXAMPLES

The invention will be more fully understood by reference to the following examples. The examples should not, however, be construed as limiting the scope of the present disclosure. It is understood that the example and embodiments described herein are for illustrative purposes only and that various modifications or changes in light thereof will be suggested to persons skilled in the art and are to be included within the spirit and purview of this application and scope of the appended claims.

Example 1: Identification of the Minimal Set of Dynamic Motifs on Hypervariable Regions To understand variability of antibody variable domains at a structural level, an algorithm was developed to map the geometric alignment for antibody variable domains, and further, to calculate the structural and sequence entropy based upon the geometric alignment. Taking such an approach combines the classical theory of antibody diversity being determined by the well-established process of V(D)J recombination coupled with conformational diversity from dynamic units (template-directed conformational selection by Linus Pauling; See e.g., James, L. and Tawfik, D. "Conformational diversity and protein evolution—a 60-year-old hypothesis revisited", *Trends Biochem Sci.* 2003 July; 28(7):361-8) to allow sampling of an almost infinite epitope space by selection and adaptation of antibody binding sites. As an example, this algorithm was used to analyze the structural and sequence variability of 81 high-resolution crystal structures of human antibody variable light chain domains. Entropy was calculated and plotted for every position of the variable light chain domain (FIG. 1A; structural entropy in bold line, sequence entropy in dotted line). The results obtained by calculating the structural and sequence entropy based upon geometric alignment were used to locate the hyper-variable (HVR) regions, and to identify the critical positions on these variable regions. For comparison, the HVRs (as defined by the methodology described above) and CDRs (as defined by Kabat) were identified for an exemplary antibody light chain variable domain sequence (FIG. 1B).

Interestingly, variability as assessed by structural alignments was generally lower than the variability observed with sequence alignments. While variability was generally lower as assessed by structural alignments, there were a number of sites/regions with dramatic structural variation, suggesting these variable sites may play critical roles in antibody function. Furthermore, some of those hyper variable regions show high flexibility with multiple conformations. The identification of regions of highly variable residues gave a more comprehensive picture of the conservation and variability of antibody variable domains that could be exploited in new antibody designs. The identification of the dynamic motif made it possible to cover a wide range of structural diversity with a reduced number of amino acid sequences. The surprising advantage of this approach to antibody design was that a more limited number of dynamic motifs could be employed in the variable regions to cover a wide range of antibody structural diversity and provide broad flexibility in these antibodies which may allow binding to multiple antigens of interest. As such, a common light chain library (called DL280) was constructed using single human germline or germline-derived sequences for the invariant residues, while a limited number of dynamic motifs were used for the hyper variable regions to capture the wide range of structural variability identified in the variable regions HVR-L1, HVR-L2, and HVR-L3.

Example 2: Construction of Common Light Chain Libraries

Construction of the Light Chain Library DL280

To begin construction of the DL280 light chain library, 20 mini-genes were synthesized that encoded 20 combinations of HVR-L1 and HVR-L2 sequences (Table 1). The synthesized mini-genes were then digested with PvuI and BamHI, and ligated into the target vector Fad22 that was digested with the same two restriction enzymes. The ligation mixtures were transformed into DH10B cells, the 20 constructs were purified, and the sequences were verified for the next stage of construction.

A total of 14 oligo pairs that encoded 14 HVR-L3 sequences (Table 1) were designed and synthesized. Oligo annealing was performed in a PCR machine with the following settings: 95° C. for 3 minutes, and then 35 cycles (15 seconds for each cycle) beginning at 95° C., decreasing temperature by 1° C. every cycle. After annealing, each pair was digested individually with PstI and Acc65I, and ligated individually into the above-mentioned 20 constructs digested with the same two restriction enzymes. The ligation mixtures were transformed into DH10B cells individually, the resulting 280 constructs were purified, quantified, and the sequences were verified. The sequences of the HVR-L1, HVR-L2, and HVR-L3 regions corresponding to these 280 constructs are listed in Table 2. Moreover, these 280 constructs each share the same framework regions, namely FW-L1 (SEQ ID NO:24), FW-L2 (SEQ ID NO:25), FW-L3 (SEQ ID NO:26), and FW-L4 (SEQ ID NO:27). Equal amounts of each of the 280 constructs were mixed for library construction.

The above-mentioned mixture of 280 plasmids was digested with PvuI and Acc65I, and ligated into the phagemid vector Fad40 that was also digested with the same two restriction enzymes. The ligation mixtures were transformed into DH10B cells, the resulting library (DL280) was purified, quantified, and stored for the assembly of the complete phagemid library.

Construction of the VH Library

Multiple degenerate oligos encoding VH_vr1s and VH_vr2s were designed, synthesized, and converted into double stranded DNA via the following protocol: 0.75 μL of 0.2 μM template oligos were mixed with 10 μL 5× PrimeSTAR buffer, 4 μL dNTP mixture, 1 μL of 100 μM forward primer, 1 μL of 100 μM reverse primer, 0.5 μL of PrimeSTAR HS DNA Polymerase (2.5 U/μL), and 33 μL of water. The PCR solutions were preheated at 96° C. for 5 minutes, then 14 cycles (96° C. for 15 seconds, 60° C. for 15 seconds, 72° C. for six seconds) were performed, followed by extension at 72° C. for three minutes. The VH_vr1s were amplified using the primer pair F_1999 (CGTTTGTCCTGTGCAGCTTCCGG) (SEQ ID NO:61) and R_1999 (CGAGGCCCTTACCCGGGGCCTGACG) (SEQ ID NO:62), while VH_vr2s were amplified using the primer pair F_2003 (CCGGGTAAGGGCCTCGAGTGG) (SEQ ID NO:63) and R_2003 (GAGCACGTCCGTTCGAATTGTCGCGACTTATAG) (SEQ ID NO:64) (Table 4).

The double stranded VH_vr1s and VH_vr2s were joined together through overlapping sequences at their 5' or 3' ends. The protocol used was as follows: 20 ng of VH_vr1 and 20 ng of VH_vr2 templates were mixed with 10 μL 5× PrimeSTAR buffer, 4 μL dNTP mixture, 1 μL of 100 μM F_1999 primer, 1 μL of 100 μM R_2003 primer, 0.5 μL of PrimeSTAR HS DNA Polymerase (2.5 U/μL), and water (up to 50 μL). The mixtures were preheated at 96° C. for 5 minutes, then 14 cycles (96° C. for 15 seconds, 60° C. for 15 seconds, 72° C. for 10 seconds) were performed, followed by extension at 72° C. for three minutes. These PCR fragments were then purified through gel electrophoresis (GENEray Gel Extraction kit), digested with BspEI and BstBI (Thermo Scientific), and subsequently cloned into FTV014 digested with the same two enzymes. The ligation mixture was transformed into DH10B cells by electroporation, and the number of colonies exceeding 10 fold of calculated diversity was collected for plasmid preparation. The purified plasmids constituted library VH-VR12.

Several hundred degenerate oligos encoding VH_vr3 were designed, synthesized, and converted into double stranded DNA through the following protocol: 0.75 μL of 0.2 μM template oligos were mixed with 10 μL 5× PrimeSTAR buffer, 4 μL dNTP mixture, 1 μL of 100 μM forward primer, 1 μL of 100 μM reverse primer, 0.5 μL of PrimeSTAR HS DNA Polymerase (2.5 U/μL), and 33 μL of water. The PCR solutions were preheated at 96° C. for 5 minutes, then 14 cycles (96° C. for 15 seconds, 60° C. for 15 seconds, 72° C. for six seconds) were performed, followed by extension at 72° C. for three minutes. The forward primer was S1089 (ACAACTGAACAGCTTAAGAGCTGAGGACACTGCCGTCTATTATTG) (SEQ ID NO:65) and the reverse primer was S1090 (GAGGAGACGGTGACTAGTGTTCCTTGACCCCA) (SEQ ID NO:66) (Table 4). The double stranded DNAs encoding the VH_vr3 were then purified through gel electrophoresis (GENEray Gel Extraction kit), digested with AflII and SpeI (Thermo Scientific), and subsequently cloned into FTV012 digested with the same two restriction enzymes. The ligation mixture was transformed into DH10B cells by electroporation, and the number of colonies exceeding 10 fold of calculated diversity was collected for plasmid preparation. The purified plasmids constituted library VH-VR3.

To assemble the full length VH library, the purified VH-VR3 library plasmid mixture was digested with AflII and SpeI (NEB), and the VR3-encoding fragments were purified through gel electrophoresis (GENEray Gel Extraction kit), and subsequently cloned into VH-VR12 library plasmid mixture that had been digested with the same two restriction enzymes. The ligation products were desalted (QIAquick® PCR Purification Kit (QIAGEN)) before rolling circle amplification (RCA). RCA was carried out as follows: 40 ng ligation products were mixed with 10 μL 10× NEBuffer 4, 50 μL of 100 μM pd(N)8, and water (up to 88.5 μL), heated to 95° C. for three minutes, and annealed for 65 cycles (30 second each cycle) with each cycle decreasing by 1° C. The annealed reactions were incubated overnight at 30° C. after the addition of 10 μL of 10 mM dNTP mix, 1 μL of 100×BSA, and 0.5 μL of Phi29 DNA polymerase. The RCA products were first digested with NotI, DNA fragments were purified (QIAquick® PCR Purification Kit), and further digested with XhoI. The digested products were then ligated with T4 DNA ligase (Thermo Scientific). After purification through ethanol precipitation, the ligation products were transformed into DH10B cells by electroporation, and the number of colonies exceeding 10 fold of calculated diversity was collected for plasmid preparation. The purified plasmids constituted library VH-VR123.

TABLE 4 primers used for PCR amplification

| Primer | Sequence |
|---|---|
| F_1999 | CGTTTGTCCTGTGCAGCTTCCGG (SEQ ID NO: 61) |
| R_1999 | CGAGGCCCTTACCCGGGGCCTGACG (SEQ ID NO: 62) |
| F_2003 | CCGGGTAAGGGCCTCGAGTGG (SEQ ID NO: 63) |
| R_2003 | GAGCACGTCCGTTCGAATTGTCGCGACTTATAG (SEQ ID NO: 64) |
| S1089 | ACAACTGAACAGCTTAAGAGCTGAGGACACTGCCGTCTATTATTG (SEQ ID NO: 65) |
| S1090 | GAGGAGACGGTGACTAGTGTTCCTTGACCCCA (SEQ ID NO: 66) |

Construction of the Common Light Chain Library

The common light library was composed of the heavy chain library derived from the VH-VR123 library and the light chain library derived from the DL280 library. Both the VH-VR123 library plasmids and the DL280 library plasmids were digested with BspEI and SpeI (Thermo Scientific). The DNA fragments encoding the heavy chain derived from the VH-VR123 library were cloned into the vector backbones derived from the DL280 library. The ligation products were desalted (QIAquick® PCR Purification Kit (QIAGEN)) before rolling circle amplification (RCA). RCA was carried out as follows: 40 ng ligation products were mixed with 10 μL 10× NEBuffer 4, 50 μL of 100 μM pd(N)8, and water (up to 88.5 μL), heated to 95° C. for three minutes, and annealed for 65 cycles (30 second each cycle) with each cycle decreasing by 1° C. The annealed reactions were incubated overnight at 30° C. after the addition of 10 μL of 10 mM dNTP mix, 1 μL of 100×BSA, and 0.5 μL of Phi29 DNA polymerase. The RCA products were first digested with NotI, DNA fragments were purified (QIAquick® PCR Purification Kit), and further digested with Acc65I. The digested products were then ligated with T4 DNA ligase (Thermo Scientific). After purification through ethanol precipitation, the ligation products were transformed into ER2738 cells by electroporation. A total number of $3.5*10^9$ colonies were collected from plates (2×YT, 1% glucose, 100 μg/mL ampicillin).

Example 3: Screening the Common Light Chain Library to Isolate Antibodies of Interest Preparation of Common Light Chain Library Phagemid Particles To prepare common light chain library phagemid particles for antigen panning, 1.6 liters of ER2738 cells harboring the common light chain library (described in Example 2 above) were inoculated in media containing 2×YT, 2% glucose, 100 μg/mL ampicillin and 12.5 μg/mL tetracycline at a starting $OD_{600}$ of 0.1. The culture was grown at 37° C., shaking at 250 rpm, until it reached $OD_{600}$ of 0.6-0.8. The cells were then infected with M13KO7 helper phages at a multiplicity of infection (MOI) of 10 for 30 minutes at 37° C. The infected ER2738 cells were grown overnight at 22° C. in 3.2 liters of media containing 2×YT, 100 μg/mL ampicillin and 50 μg/mL kanamycin. Culture supernatants were then harvested by centrifugation at 10,000 rpm for 15 minutes, and filtered through a 0.45 μm low-binding membrane filter (Corning). The phagemid particles were then precipitated from the filtered supernatant using PEG/NaCl, and resuspended in PBS. An additional round of PEG/NaCl precipitation, followed by resuspension in PBS, was conducted. Phage titer was determined by $OD_{268}$ measurement (assuming 1 unit at $OD_{268}$ is approximately $1*10^{13}$ phage particles/mL) and confirmed by plaque assay. Library phagemid particles were stocked in 20% glycerol at −80° C.

Phage Library Panning

Antigen proteins at a concentration of 1-30 μg/ml were coated on Maxisorp strips (Thermo Scientific, Cat. No. 446469) overnight at 4° C. Multiple wells of antigens were prepared for each library. The coated wells were first blocked with 5% milk in PBS for 1-2 hours at room temperature and washed with PBS. Then 1,100 μL/well of phagemid particle solution (typically $1-5*10^{12}$ phages in 2% milk-PBS) was added into 4 parallel wells and incubated for 1-2 hours. Wells were then washed several times with PBS with increasing concentrations of Tween 20 (from 0.1% to 0.3%), and finally with PBS alone. The bound phagemid particles were eluted from the wells with 100 μL of 0.2 M glycine-HCl for 10 minutes at room temperature. The eluted phages were immediately neutralized with 18 μL of 1 M Tris-HCl (pH 9.1)

Alternatively, phagemid library panning was performed using Dynabeads (M280, Streptavidin, Invitrogen, Cat. No. 60210) through KingFisher (Thermo Scientific) according to the manufacturer's instructions. 300 μL of Dynabeads were washed with PBS and incubated with biotinylated anti-human Fc for 20 minutes at room temperature. The beads were then blocked with 5% BSA in PBS for one hour at room temperature. Fc-fusion antigens (70-100 pmols) were captured by one hour incubation at room temperature. The beads were then washed once with PBS, and incubated with 1 mL of phage library solution (typically $5*10^{12}$ to $1*10^{13}$ phage particles in 5% BSA-PBS) for 1-2 hours. The beads were then washed several times with PBS/Tween (0.1% to 0.3%) and PBS, and the bound phages were eluted from the beads with 100 μL of 0.2 M glycine-HCl for 10 minutes at room temperature. The eluted phages were immediately neutralized with 18 μL of 1 M Tris-HCl (pH 9.1). A total of three or four rounds of panning were conducted against each of the antigens, and a 10-100 fold excess of purified human Fc was included to reduce background binding.

For some of the antigens tested, 2 mL of antigens (10-30 μg/mL) were used to coat immune-tubes overnight at 4° C. The volume of blocking, washing, and elution solutions were increased accordingly.

Amplification of Enriched Phage

The eluted, enriched phage pool was further amplified as follows: ER2738 cells were infected with the eluted phagemid particles at 37° C. for 30 minutes. The infected cells were then plated out on 2×YT agar plates with 2% glucose, 100 μg/mL ampicillin and 12.5 μg/mL tetracycline. The colonies were harvested from plates, grown in 100 ml of 2% glucose, 100 μg/mL ampicillin and 12.5 μg/mL tetracycline, and infected with M13KO7 helper phage. The amplified phages were purified and quantified by the processes described above. Usually, the eluted phages after the final round of panning were used to infect ER2738 cells, and the resulting ER2738 colonies were picked for supernatant ELISA screening assays.

Supernatant Sandwich Elisa Assay

A sensitive sandwich Elisa assay was developed to measure the Fabs present in bacterial supernatant. Microplates were coated with polyclonal anti-human IgG (Fab specific) (Sigma I5260) to capture Fabs present in the bacterial supernatant, and then HRP labeled goat anti-human Fe was used to detect the amount of Fabs captured. The $A_{450}$ of each well was measured to determine the Fab binding activity. The primary hits were defined as those whose ELISA signals were at least twice that of background, and were further characterized in the following example (Example 4)

Example 4: Characterization of Antibodies In Vitro

Figure 3:
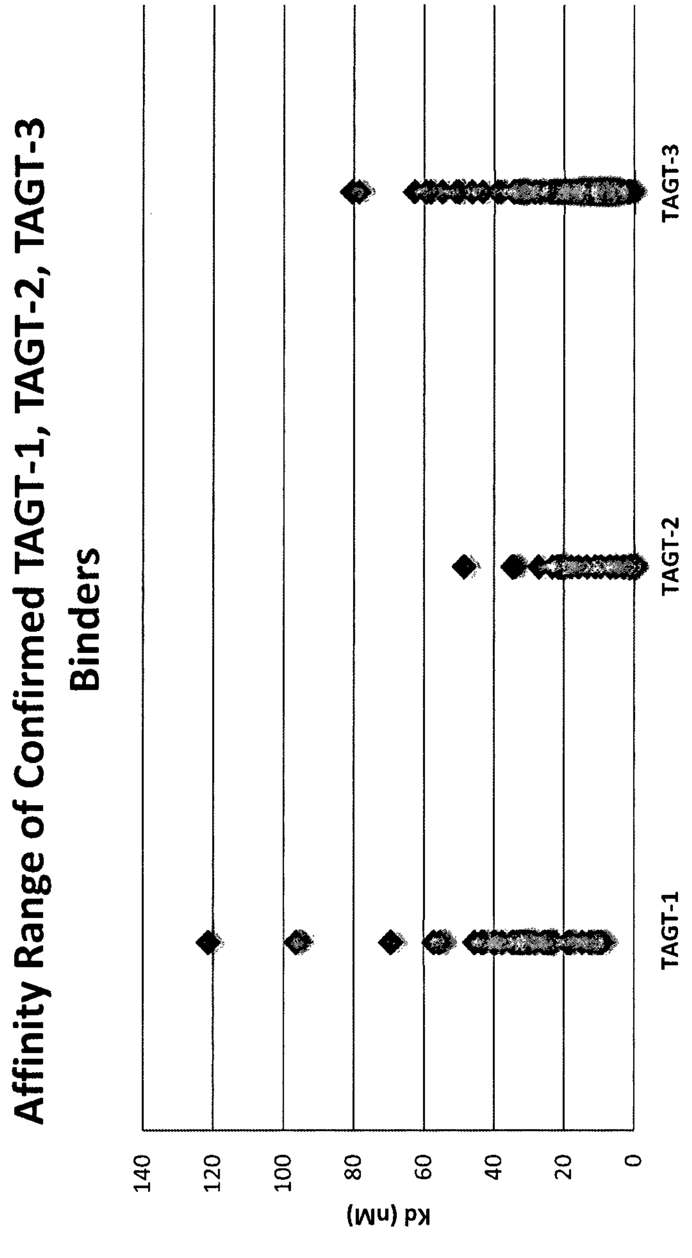
FIG. 3 shows the affinity measurements for fabs with confirmed binding to the antigens TAGT-1, TAGT-2, and TAGT-3.

The Fabs corresponding to the primary hits identified in Example 3 above, which were tagged at their C-terminus of the CH1 domain with a His6 tag, were over-expressed in *E. coli*, and were purified through Ni-NTA resin (Thermo Fisher Scientific) according to the manufacturer's instructions. Their affinities were measured by the ForteBio Octet RED96 System. Briefly, the AHC sensors (anti-human IgG-Fc capture dip and read biosensors) were used to capture the antigen, and dipped into well containing the purified Fabs that were diluted to 5-10 μg/mL with kinetic buffer (for additional descriptions see e.g., ForteBio, Anti-human IgG Capture (AHC) Biosensors, Product Insert 41-0072-PD (2008)). The acquired ForteBio data were processed with Data Acquisition software 7.1, and kinetic data were fitted to a 1:1 Langmuir binding model. The Fab affinities measured at 25° C. for targets TAGT-1, TAGT-2, and TAGT-3 are shown in Table 5 and FIG. 3. These three target antigens (TAGT-1, TAGT-2, and TAGT-3) were unrelated proteins sharing less than 17% sequence identity.

TABLE 5

Affinity measurements for Fabs with confirmed binding to TAGT-1, TAGT-2, and TAGT-3 at 25° C.

| Hit ID | Target ID | Kd (M) |
|---|---|---|
| 3763 | TAGT-1 | 9.30E−09 |
| 7190 | TAGT-1 | 1.03E−08 |
| 7166 | TAGT-1 | 1.24E−08 |
| 3760 | TAGT-1 | 1.26E−08 |
| 7163 | TAGT-1 | 1.26E−08 |
| 7183 | TAGT-1 | 1.48E−08 |
| 3757 | TAGT-1 | 1.84E−08 |
| 7077 | TAGT-1 | 1.88E−08 |
| 7129 | TAGT-1 | 1.90E−08 |
| 7097 | TAGT-1 | 2.43E−08 |
| 7080 | TAGT-1 | 2.44E−08 |
| 7199 | TAGT-1 | 2.46E−08 |
| 7078 | TAGT-1 | 2.52E−08 |
| 4216 | TAGT-1 | 2.59E−08 |
| 4218 | TAGT-1 | 2.85E−08 |
| 7079 | TAGT-1 | 2.99E−08 |
| 7131 | TAGT-1 | 3.04E−08 |
| 3762 | TAGT-1 | 3.04E−08 |
| 7135 | TAGT-1 | 3.17E−08 |
| 7109 | TAGT-1 | 3.20E−08 |
| 7201 | TAGT-1 | 3.26E−08 |
| 7105 | TAGT-1 | 3.33E−08 |
| 7120 | TAGT-1 | 3.45E−08 |
| 7100 | TAGT-1 | 3.50E−08 |
| 7159 | TAGT-1 | 3.79E−08 |
| 7128 | TAGT-1 | 3.97E−08 |
| 7133 | TAGT-1 | 4.03E−08 |
| 7081 | TAGT-1 | 4.31E−08 |
| 7088 | TAGT-1 | 4.36E−08 |
| 7092 | TAGT-1 | 4.57E−08 |
| 4222 | TAGT-1 | 5.55E−08 |
| 7090 | TAGT-1 | 5.55E−08 |
| 4220 | TAGT-1 | 5.72E−08 |
| 7087 | TAGT-1 | 6.96E−08 |
| 3761 | TAGT-1 | 9.65E−08 |
| 4217 | TAGT-1 | 9.67E−08 |
| 7107 | TAGT-1 | 1.22E−07 |
| 7055 | TAGT-2 | 7.57E−10 |
| 5129 | TAGT-2 | 1.12E−09 |
| 7044 | TAGT-2 | 1.12E−09 |
| 3780 | TAGT-2 | 1.47E−09 |
| 7035 | TAGT-2 | 3.04E−09 |
| 5132 | TAGT-2 | 3.06E−09 |
| 7073 | TAGT-2 | 3.19E−09 |
| 7039 | TAGT-2 | 5.21E−09 |
| 5144 | TAGT-2 | 6.79E−09 |
| 5145 | TAGT-2 | 7.00E−09 |
| 5126 | TAGT-2 | 9.54E−09 |
| 7068 | TAGT-2 | 1.11E−08 |
| 7043 | TAGT-2 | 1.34E−08 |
| 7036 | TAGT-2 | 1.59E−08 |
| 7066 | TAGT-2 | 1.80E−08 |
| 7032 | TAGT-2 | 2.08E−08 |
| 7037 | TAGT-2 | 2.10E−08 |
| 7047 | TAGT-2 | 2.15E−08 |
| 5131 | TAGT-2 | 2.17E−08 |
| 7038 | TAGT-2 | 2.33E−08 |
| 7040 | TAGT-2 | 2.72E−08 |
| 7067 | TAGT-2 | 3.41E−08 |
| 7030 | TAGT-2 | 3.47E−08 |
| 7025 | TAGT-2 | 4.87E−08 |
| 7222 | TAGT-3 | 1.26E−09 |
| 5989 | TAGT-3 | 1.74E−09 |
| 7238 | TAGT-3 | 2.14E−09 |
| 7231 | TAGT-3 | 3.38E−09 |
| 7243 | TAGT-3 | 4.95E−09 |
| 7249 | TAGT-3 | 5.36E−09 |
| 7221 | TAGT-3 | 5.58E−09 |
| 5930 | TAGT-3 | 5.66E−09 |
| 5123 | TAGT-3 | 5.67E−09 |
| 7246 | TAGT-3 | 6.22E−09 |
| 7241 | TAGT-3 | 6.43E−09 |
| 5113 | TAGT-3 | 6.80E−09 |
| 7256 | TAGT-3 | 7.08E−09 |
| 5128 | TAGT-3 | 7.12E−09 |
| 5119 | TAGT-3 | 7.54E−09 |

TABLE 5-continued

Affinity measurements for Fabs with confirmed binding to TAGT-1, TAGT-2, and TAGT-3 at 25° C.

| Hit ID | Target ID | Kd (M) |
|---|---|---|
| 7226 | TAGT-3 | 7.57E−09 |
| 7228 | TAGT-3 | 7.62E−09 |
| 5921 | TAGT-3 | 8.01E−09 |
| 7232 | TAGT-3 | 8.06E−09 |
| 5997 | TAGT-3 | 8.51E−09 |
| 5138 | TAGT-3 | 8.55E−09 |
| 5935 | TAGT-3 | 8.78E−09 |
| 7213 | TAGT-3 | 8.87E−09 |
| 7229 | TAGT-3 | 8.91E−09 |
| 7247 | TAGT-3 | 8.93E−09 |
| 7220 | TAGT-3 | 9.12E−09 |
| 5121 | TAGT-3 | 9.29E−09 |
| 7209 | TAGT-3 | 9.36E−09 |
| 7225 | TAGT-3 | 9.53E−09 |
| 7230 | TAGT-3 | 9.53E−09 |
| 7252 | TAGT-3 | 9.56E−09 |
| 7258 | TAGT-3 | 9.72E−09 |
| 7210 | TAGT-3 | 9.85E−09 |
| 7244 | TAGT-3 | 1.05E−08 |
| 7254 | TAGT-3 | 1.07E−08 |
| 5967 | TAGT-3 | 1.10E−08 |
| 7257 | TAGT-3 | 1.11E−08 |
| 5932 | TAGT-3 | 1.12E−08 |
| 5993 | TAGT-3 | 1.13E−08 |
| 5980 | TAGT-3 | 1.14E−08 |
| 5990 | TAGT-3 | 1.15E−08 |
| 5115 | TAGT-3 | 1.16E−08 |
| 7240 | TAGT-3 | 1.17E−08 |
| 7255 | TAGT-3 | 1.20E−08 |
| 5913 | TAGT-3 | 1.23E−08 |
| 7211 | TAGT-3 | 1.26E−08 |
| 5968 | TAGT-3 | 1.27E−08 |
| 7248 | TAGT-3 | 1.28E−08 |
| 5970 | TAGT-3 | 1.35E−08 |
| 7245 | TAGT-3 | 1.38E−08 |
| 5964 | TAGT-3 | 1.40E−08 |
| 5995 | TAGT-3 | 1.42E−08 |
| 7219 | TAGT-3 | 1.44E−08 |
| 5116 | TAGT-3 | 1.46E−08 |
| 7218 | TAGT-3 | 1.49E−08 |
| 5906 | TAGT-3 | 1.50E−08 |
| 5994 | TAGT-3 | 1.58E−08 |
| 5923 | TAGT-3 | 1.60E−08 |
| 7215 | TAGT-3 | 1.61E−08 |
| 5934 | TAGT-3 | 1.66E−08 |
| 5912 | TAGT-3 | 1.68E−08 |
| 5992 | TAGT-3 | 1.70E−08 |
| 7212 | TAGT-3 | 1.70E−08 |
| 7242 | TAGT-3 | 1.71E−08 |
| 5915 | TAGT-3 | 1.82E−08 |
| 5920 | TAGT-3 | 1.88E−08 |
| 7216 | TAGT-3 | 1.88E−08 |
| 5922 | TAGT-3 | 1.95E−08 |
| 5928 | TAGT-3 | 1.97E−08 |
| 5963 | TAGT-3 | 2.07E−08 |
| 5983 | TAGT-3 | 2.09E−08 |
| 7237 | TAGT-3 | 2.13E−08 |
| 7235 | TAGT-3 | 2.18E−08 |
| 5996 | TAGT-3 | 2.21E−08 |
| 5979 | TAGT-3 | 2.31E−08 |
| 5919 | TAGT-3 | 2.38E−08 |
| 7239 | TAGT-3 | 2.40E−08 |
| 5961 | TAGT-3 | 2.41E−08 |
| 5125 | TAGT-3 | 2.42E−08 |
| 7251 | TAGT-3 | 2.69E−08 |
| 5977 | TAGT-3 | 2.70E−08 |
| 6010 | TAGT-3 | 2.83E−08 |
| 5976 | TAGT-3 | 2.88E−08 |
| 5933 | TAGT-3 | 3.13E−08 |
| 5929 | TAGT-3 | 3.20E−08 |
| 5926 | TAGT-3 | 3.23E−08 |
| 5978 | TAGT-3 | 3.25E−08 |
| 5910 | TAGT-3 | 3.30E−08 |
| 5914 | TAGT-3 | 3.30E−08 |
| 5911 | TAGT-3 | 3.35E−08 |

TABLE 5-continued

Affinity measurements for Fabs with confirmed binding to TAGT-1, TAGT-2, and TAGT-3 at 25° C.

| Hit ID | Target ID | Kd (M) |
|---|---|---|
| 5114 | TAGT-3 | 3.42E−08 |
| 5918 | TAGT-3 | 3.46E−08 |
| 5905 | TAGT-3 | 3.83E−08 |
| 5985 | TAGT-3 | 3.92E−08 |
| 5927 | TAGT-3 | 4.35E−08 |
| 5986 | TAGT-3 | 4.65E−08 |
| 5974 | TAGT-3 | 5.02E−08 |
| 6008 | TAGT-3 | 5.10E−08 |
| 6004 | TAGT-3 | 5.50E−08 |
| 5916 | TAGT-3 | 5.83E−08 |
| 5924 | TAGT-3 | 5.95E−08 |
| 5999 | TAGT-3 | 6.29E−08 |
| 6000 | TAGT-3 | 7.86E−08 |
| 5962 | TAGT-3 | 8.06E−08 |

As indicated by Table 5 above, multiple antibodies targeting three different antigens with high affinity could be successfully identified and selected from the prepared library.

Example 5: Application of the DL280 Library

To demonstrate the application of the DL280 light chain library assembled in Example 2 under different scenarios, three antibody libraries were constructed using the DL280 light chain library:

DPL5: the whole set of DL280 light chains paired with a large VH library
 VH: diversity is $>10^9$ VHs
 VL: the whole set of DL280

SEL021: the whole set of DL280 light chains paired with a small VH library
 VH: 20 VHs
 VL: the whole set of DL280

DPL16-DPL34: a subset of the DL280 light chains paired with a large VH library
 VH: diversity is $>10^{10}$ VHs
 VL: a single species of DL280

To examine the robustness and flexibility of the DL280 light chain library, the DPL5, SEL021, and DPL16DPL34 libraries were screened against three targets: TAGT-1, TAGT-2, and TAGT-3 (as described in Example 3). Positive hits were identified from each of the three libraries tested, and a total of 165 positive hits containing 24 unique VLs were measured and confirmed with affinity data (Table 6).

TABLE 6

Affinity data for confirmed hits

| Hit ID | Library | Antigen | Kd (M) |
|---|---|---|---|
| DL280-135 (SEQ ID NO: 28) | | | |
| 3757 | DPL5 | TAGT-1 | 1.84E−08 |
| 4220 | DPL5 | TAGT-1 | 5.72E−08 |
| 5905 | DPL16 | TAGT-3 | 3.83E−08 |
| 5906 | DPL16 | TAGT-3 | 1.50E−08 |
| 5910 | DPL16 | TAGT-3 | 3.30E−08 |
| 5911 | DPL16 | TAGT-3 | 3.35E−08 |
| 5912 | DPL16 | TAGT-3 | 1.68E−08 |
| 5913 | DPL16 | TAGT-3 | 1.23E−08 |
| 5914 | DPL16 | TAGT-3 | 3.30E−08 |
| 5915 | DPL16 | TAGT-3 | 1.82E−08 |
| 5916 | DPL16 | TAGT-3 | 5.83E−08 |
| 5918 | DPL16 | TAGT-3 | 3.46E−08 |

TABLE 6-continued

| Affinity data for confirmed hits | | | |
|---|---|---|---|
| Hit ID | Library | Antigen | Kd (M) |
| 5919 | DPL16 | TAGT-3 | 2.38E−08 |
| 5920 | DPL16 | TAGT-3 | 1.88E−08 |
| 5921 | DPL16 | TAGT-3 | 8.01E−09 |
| 5922 | DPL16 | TAGT-3 | 1.95E−08 |
| 5923 | DPL16 | TAGT-3 | 1.60E−08 |
| 5924 | DPL16 | TAGT-3 | 5.95E−08 |
| 5926 | DPL16 | TAGT-3 | 3.23E−08 |
| 5927 | DPL16 | TAGT-3 | 4.35E−08 |
| 5928 | DPL16 | TAGT-3 | 1.97E−08 |
| 5929 | DPL16 | TAGT-3 | 3.20E−08 |
| 5961 | DPL16 | TAGT-3 | 2.41E−08 |
| 5962 | DPL16 | TAGT-3 | 8.06E−08 |
| 5963 | DPL16 | TAGT-3 | 2.07E−08 |
| 5964 | DPL16 | TAGT-3 | 1.40E−08 |
| 5967 | DPL16 | TAGT-3 | 1.10E−08 |
| 5968 | DPL16 | TAGT-3 | 1.27E−08 |
| 5970 | DPL16 | TAGT-3 | 1.35E−08 |
| 5974 | DPL16 | TAGT-3 | 5.02E−08 |
| 5976 | DPL16 | TAGT-3 | 2.88E−08 |
| 5977 | DPL16 | TAGT-3 | 2.70E−08 |
| 5978 | DPL16 | TAGT-3 | 3.25E−08 |
| 5979 | DPL16 | TAGT-3 | 2.31E−08 |
| 5980 | DPL16 | TAGT-3 | 1.14E−08 |
| 5983 | DPL16 | TAGT-3 | 2.09E−08 |
| 5985 | DPL16 | TAGT-3 | 3.92E−08 |
| 5986 | DPL16 | TAGT-3 | 4.65E−08 |
| 5989 | DPL16 | TAGT-3 | 1.74E−09 |
| 5990 | DPL16 | TAGT-3 | 1.15E−08 |
| 5992 | DPL16 | TAGT-3 | 1.70E−08 |
| 5993 | DPL16 | TAGT-3 | 1.13E−08 |
| 5994 | DPL16 | TAGT-3 | 1.58E−08 |
| 5995 | DPL16 | TAGT-3 | 1.42E−08 |
| 5996 | DPL16 | TAGT-3 | 2.21E−08 |
| 5997 | DPL16 | TAGT-3 | 8.51E−09 |
| 5999 | DPL16 | TAGT-3 | 6.29E−08 |
| 6000 | DPL16 | TAGT-3 | 7.86E−08 |
| 6004 | DPL16 | TAGT-3 | 5.50E−08 |
| DL280-70 (SEQ ID NO: 32) | | | |
| 4218 | DPL5 | TAGT-1 | 2.85E−08 |
| 4222 | DPL5 | TAGT-1 | 5.55E−08 |
| 5114 | SEL021 | TAGT-3 | 3.42E−08 |
| 7035 | DPL19 | TAGT-2 | 3.04E−09 |
| 7036 | DPL19 | TAGT-2 | 1.59E−08 |
| 7037 | DPL19 | TAGT-2 | 2.10E−08 |
| 7038 | DPL19 | TAGT-2 | 2.33E−08 |
| 7039 | DPL19 | TAGT-2 | 5.21E−09 |
| 7040 | DPL19 | TAGT-2 | 2.72E−08 |
| 7090 | DPL19 | TAGT-1 | 5.55E−08 |
| 7092 | DPL19 | TAGT-1 | 4.57E−08 |
| 7097 | DPL19 | TAGT-1 | 2.43E−08 |
| 7100 | DPL19 | TAGT-1 | 3.50E−08 |
| 7105 | DPL19 | TAGT-1 | 3.33E−08 |
| 7107 | DPL19 | TAGT-1 | 1.22E−07 |
| 7109 | DPL19 | TAGT-1 | 3.20E−08 |
| 7120 | DPL19 | TAGT-1 | 3.45E−08 |
| 7221 | DPL19 | TAGT-3 | 5.58E−09 |
| 7222 | DPL19 | TAGT-3 | 1.26E−09 |
| 7225 | DPL19 | TAGT-3 | 9.53E−09 |
| 7226 | DPL19 | TAGT-3 | 7.57E−09 |
| 7228 | DPL19 | TAGT-3 | 7.62E−09 |
| 7229 | DPL19 | TAGT-3 | 8.91E−09 |
| 7230 | DPL19 | TAGT-3 | 9.53E−09 |
| 7231 | DPL19 | TAGT-3 | 3.38E−09 |
| 7232 | DPL19 | TAGT-3 | 8.06E−09 |
| 7235 | DPL19 | TAGT-3 | 2.18E−08 |
| 7237 | DPL19 | TAGT-3 | 2.13E−08 |
| 7238 | DPL19 | TAGT-3 | 2.14E−09 |
| 7239 | DPL19 | TAGT-3 | 2.40E−08 |
| 7240 | DPL19 | TAGT-3 | 1.17E−08 |
| 7241 | DPL19 | TAGT-3 | 6.43E−09 |
| 7242 | DPL19 | TAGT-3 | 1.71E−08 |
| 7243 | DPL19 | TAGT-3 | 4.95E−09 |
| 7244 | DPL19 | TAGT-3 | 1.05E−08 |
| 7245 | DPL19 | TAGT-3 | 1.38E−08 |
| 7246 | DPL19 | TAGT-3 | 6.22E−09 |

TABLE 6-continued

| Affinity data for confirmed hits | | | |
|---|---|---|---|
| Hit ID | Library | Antigen | Kd (M) |
| 7247 | DPL19 | TAGT-3 | 8.93E−09 |
| 7248 | DPL19 | TAGT-3 | 1.28E−08 |
| 7249 | DPL19 | TAGT-3 | 5.36E−09 |
| 7251 | DPL19 | TAGT-3 | 2.69E−08 |
| 7252 | DPL19 | TAGT-3 | 9.56E−09 |
| 7254 | DPL19 | TAGT-3 | 1.07E−08 |
| 7255 | DPL19 | TAGT-3 | 1.20E−08 |
| 7256 | DPL19 | TAGT-3 | 7.08E−09 |
| 7257 | DPL19 | TAGT-3 | 1.11E−08 |
| 7258 | DPL19 | TAGT-3 | 9.72E−09 |
| DL280-67 (SEQ ID NO: 34) | | | |
| 5145 | SEL021 | TAGT-2 | 7.00E−09 |
| 7025 | DPL18 | TAGT-2 | 4.87E−08 |
| 7030 | DPL18 | TAGT-2 | 3.47E−08 |
| 7032 | DPL18 | TAGT-2 | 2.08E−08 |
| 7077 | DPL18 | TAGT-1 | 1.88E−08 |
| 7078 | DPL18 | TAGT-1 | 2.52E−08 |
| 7079 | DPL18 | TAGT-1 | 2.99E−08 |
| 7080 | DPL18 | TAGT-1 | 2.44E−08 |
| 7081 | DPL18 | TAGT-1 | 4.31E−08 |
| 7087 | DPL18 | TAGT-1 | 6.96E−08 |
| 7088 | DPL18 | TAGT-1 | 4.36E−08 |
| 7209 | DPL18 | TAGT-3 | 9.36E−09 |
| 7210 | DPL18 | TAGT-3 | 9.85E−09 |
| 7211 | DPL18 | TAGT-3 | 1.26E−08 |
| 7212 | DPL18 | TAGT-3 | 1.70E−08 |
| 7213 | DPL18 | TAGT-3 | 8.87E−09 |
| 7215 | DPL18 | TAGT-3 | 1.61E−08 |
| 7216 | DPL18 | TAGT-3 | 1.88E−08 |
| 7218 | DPL18 | TAGT-3 | 1.49E−08 |
| 7219 | DPL18 | TAGT-3 | 1.44E−08 |
| 7220 | DPL18 | TAGT-3 | 9.12E−09 |
| DL280-271 (SEQ ID NO: 36) | | | |
| 5930 | DPL17 | TAGT-3 | 5.66E−09 |
| 5932 | DPL17 | TAGT-3 | 1.12E−08 |
| 5933 | DPL17 | TAGT-3 | 3.13E−08 |
| 5934 | DPL17 | TAGT-3 | 1.66E−08 |
| 5935 | DPL17 | TAGT-3 | 8.78E−09 |
| 6008 | DPL17 | TAGT-3 | 5.10E−08 |
| 6010 | DPL17 | TAGT-3 | 2.83E−08 |
| DL280-207 (SEQ ID NO: 35) | | | |
| 3762 | DPL5 | TAGT-1 | 3.04E−08 |
| 7047 | DPL23 | TAGT-2 | 2.15E−08 |
| 7131 | DPL23 | TAGT-1 | 3.04E−08 |
| 7133 | DPL23 | TAGT-1 | 4.03E−08 |
| 7135 | DPL23 | TAGT-1 | 3.17E−08 |
| 7190 | DPL31 | TAGT-1 | 1.03E−08 |
| DL280-65 (SEQ ID NO: 29) | | | |
| 5119 | SEL021 | TAGT-3 | 7.54E−09 |
| 5132 | SEL021 | TAGT-2 | 3.06E−09 |
| 7043 | DPL21 | TAGT-2 | 1.34E−08 |
| 7044 | DPL21 | TAGT-2 | 1.12E−09 |
| 7128 | DPL21 | TAGT-1 | 3.97E−08 |
| 7129 | DPL21 | TAGT-1 | 1.90E−08 |
| DL280-252 (SEQ ID NO: 38) | | | |
| 5129 | SEL021 | TAGT-2 | 1.12E−09 |
| 7055 | DPL26 | TAGT-2 | 7.57E−10 |
| 7159 | DPL26 | TAGT-1 | 3.79E−08 |
| 7163 | DPL26 | TAGT-1 | 1.26E−08 |
| 7166 | DPL26 | TAGT-1 | 1.24E−08 |
| DL280-238 (SEQ ID NO: 39) | | | |
| 3780 | DPL5 | TAGT-2 | 1.47E−09 |
| 7066 | DPL31 | TAGT-2 | 1.80E−08 |
| 7067 | DPL31 | TAGT-2 | 3.41E−08 |
| 7068 | DPL31 | TAGT-2 | 1.11E−08 |
| DL280-232 (SEQ ID NO: 49) | | | |
| 7073 | DPL34 | TAGT-2 | 3.19E−09 |
| 7199 | DPL34 | TAGT-1 | 2.46E−08 |
| 7201 | DPL34 | TAGT-1 | 3.26E−08 |

TABLE 6-continued

Affinity data for confirmed hits

| Hit ID | Library | Antigen | Kd (M) |
|---|---|---|---|
| DL280-221 | | | |
| 4216 | DPL5 | TAGT-1 | 2.59E−08 |
| 5144 | SEL021 | TAGT-2 | 6.79E−09 |
| DL280-254 | | | |
| 5116 | SEL021 | TAGT-3 | 1.46E−08 |
| 7183 | DPL31 | TAGT-1 | 1.48E−08 |
| DL280-109 | | | |
| 5115 | SEL021 | TAGT-3 | 1.16E−08 |
| DL280-114 | | | |
| 5125 | SEL021 | TAGT-3 | 2.42E−08 |
| DL280-121 | | | |
| 5128 | SEL021 | TAGT-3 | 7.12E−09 |
| DL280-132 | | | |
| 3760 | DPL5 | TAGT-1 | 1.26E−08 |
| DL280-165 | | | |
| 3763 | DPL5 | TAGT-1 | 9.30E−09 |
| DL280-205 | | | |
| 5113 | SEL021 | TAGT-3 | 6.80E−09 |
| DL280-257 | | | |
| 5138 | SEL021 | TAGT-3 | 8.55E−09 |
| DL280-261 | | | |
| 5121 | SEL021 | TAGT-3 | 9.29E−09 |
| DL280-28 | | | |
| 4217 | DPL5 | TAGT-1 | 9.67E−08 |
| DL280-53 | | | |
| 3761 | DPL5 | TAGT-1 | 9.65E−08 |
| DL280-79 | | | |
| 5123 | SEL021 | TAGT-3 | 5.67E−09 |
| DL280-80 | | | |
| 5131 | SEL021 | TAGT-2 | 2.17E−08 |
| DL280-9 | | | |
| 5126 | SEL021 | TAGT-2 | 9.54E−09 |

Of the 24 unique VLs, nine of them bound to multiple targets when paired with different VHs. For example, Hit ID 3757 contained DL280-135 (SEQ ID NO:28) and a VH (SEQ ID NO:51) and bound TAGT-1, while Hit ID 5905 also contained DL280-135 but with a different VH (SEQ ID NO:52), and bound to a different target, TAGT-3. Similarly, when DL280-67 (SEQ ID NO:34) paired with one VH (SEQ ID NO:56) as Hit ID 5145, it bound TAGT-2, and when paired with a different VH (SEQ ID NO:57) as Hit ID 7077, it bound TAGT-1.

VLs from DL280 were also discovered that could bind all three target antigens when paired with different VH sequences. For example, when DL280-70 (SEQ ID NO:32) was paired with one VH (SEQ ID NO:53) as Hit ID 7035, it bound TAGT-2, when paired with second VH (SEQ ID NO:54) as Hit ID 4218, it bound TAGT-1, and when paired with a third VH (SEQ ID NO:55) as Hit ID 5114, it bound TAGT-3. An additional two DL280s bound to the same target using multiple different VHs. For example, DL280-271 (SEQ ID NO:36) bound TAGT-3 when paired with two different VHs (SEQ ID NOs: 58 and 59) as Hit IDs 5930 and 6008, respectively. Table 7 below shows sequence usage and number of targets bound for the 24 unique VLs identified during the library analysis.

TABLE 7 target binding capability of VLs

| DL280 ID | Sequence Usage Percent | Number of Target hit out of 3 |
|---|---|---|
| DL280-135 | 30% | 2 |
| DL280-70 | 28% | 3 |
| DL280-67 | 13% | 3 |
| DL280-271 | 4% | 1 |
| DL280-207 | 4% | 2 |
| DL280-65 | 4% | 3 |
| DL280-252 | 3% | 2 |
| DL280-238 | 2% | 1 |
| DL280-232 | 2% | 2 |
| DL280-221 | 1% | 2 |
| DL280-254 | 1% | 2 |
| DL280-109 | 1% | 1 |
| DL280-114 | 1% | 1 |
| DL280-121 | 1% | 1 |
| DL280-132 | 1% | 1 |
| DL280-165 | 1% | 1 |
| DL280-205 | 1% | 1 |
| DL280-257 | 1% | 1 |
| DL280-261 | 1% | 1 |
| DL280-28 | 1% | 1 |
| DL280-53 | 1% | 1 |
| DL280-79 | 1% | 1 |
| DL280-80 | 1% | 1 |
| DL280-9 | 1% | 1 |

Figure 2A:
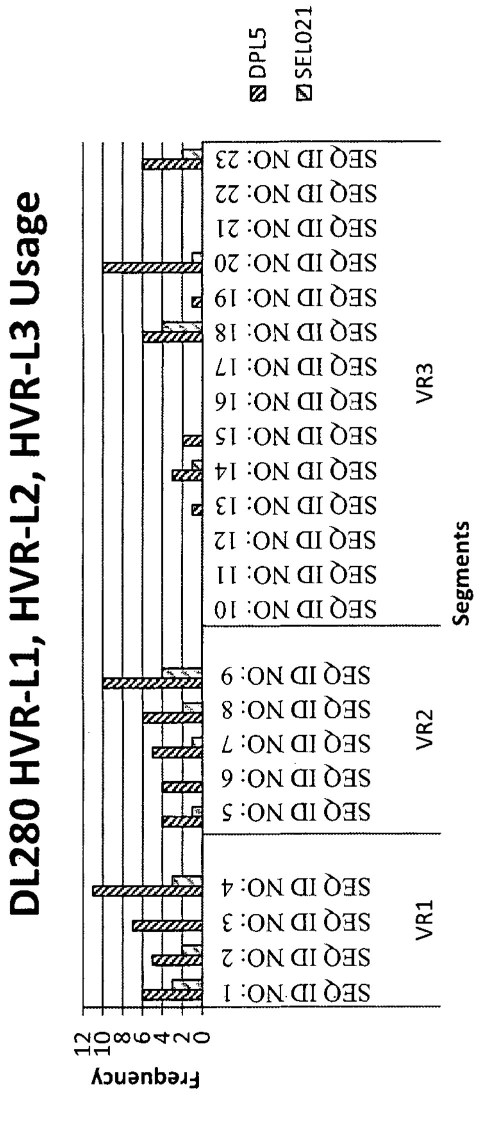
FIG. 2A shows HVR-L1, HVR-L2, and HVR-L3 segment usage for antibodies with confirmed antigen binding from the DPL5 and SEL021 antibody libraries. Amino acid sequences corresponding to the indicated SEQ ID NOs can be found in Table 1.

DL280 segment usage was analyzed for the antibody hits from the DPL5 and SEL021 libraries (FIG. 2A).

Figure 2B:
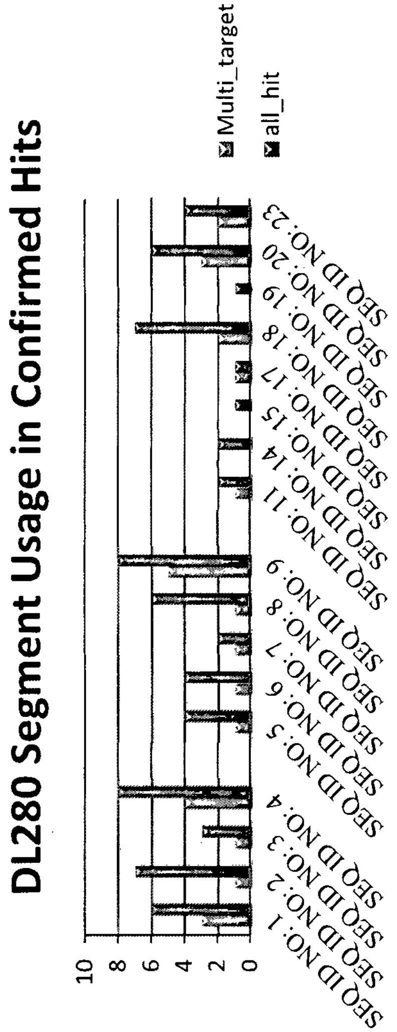
FIG. 2B shows HVR-L1, HVR-L2, and HVR-L3 segment usage for antibodies with confirmed antigen binding to single and multiple antigen targets from the DPL5, SEL021, and DPL16~34 antibody libraries. Amino acid sequences corresponding to the indicated SEQ ID NOs can be found in Table 1.

19 of the top VLs (as shown in Table 7) were built as single VL libraries (DPL16~34) by pairing the VLs with a VH library harboring greater than $10^{10}$ VH sequences, and these antibodies were re-screened by again analyzing binding to TAGT-3, TAGT-2, and TAGT-1. After confirming the hits from all three libraries (DPL5, SEL021, and DPL16-34), the DL280 segment usage (FIG. 2B) was re-assessed (Table 8). Without wishing to be bound by theory, it is thought that a high number of antigens bound by an antibody comprising a given hypervariable region may be indicative of a high degree of flexibility of that particular hypervariable region, while a high segment usage of a given hypervariable region may be indicative of robust folding of the hypervariable region (and surrounding polypeptide sequence).

TABLE 8

DL280 segment usage in confirmed hits from DPL5, SEL021, and DPL16~34

| | SEQ ID NO | Segment Usage | Frequency in hits that bind to >1 targets | Frequency in hits that bind to >0 target |
|---|---|---|---|---|
| HVR-L1 | 1 | 47% | 3 | 6 |
| | 2 | 33% | 1 | 7 |
| | 3 | 5% | 1 | 3 |
| | 4 | 15% | 4 | 8 |
| HVR-L2 | 5 | 3% | 1 | 4 |
| | 6 | 5% | 1 | 4 |
| | 7 | 4% | 1 | 2 |
| | 8 | 4% | 1 | 6 |
| | 9 | 84% | 5 | 8 |
| HVR-L3 | 11 | 2% | 1 | 2 |
| | 14 | 5% | 0 | 2 |
| | 15 | 1% | 0 | 1 |
| | 17 | 2% | 1 | 1 |
| | 18 | 36% | 2 | 7 |

TABLE 8-continued

DL280 segment usage in confirmed hits from DPL5, SEL021, and DPL16~34

| SEQ ID NO | Segment Usage | Frequency in hits that bind to >1 targets | Frequency in hits that bind to >0 target |
|---|---|---|---|
| 19 | 1% | 0 | 1 |
| 20 | 19% | 3 | 6 |
| 23 | 35% | 2 | 4 |

Segment combination distribution was also calculated for all combinations of HVR-L1, HVR-L2, and HVR-L3 (Tables 9 and 10).

TABLE 9

HVR-L1, HVR-L2, and HVR-L3 2-segment combination usage

| SEQ ID NO. | SEQ ID NO. | Percent |
|---|---|---|
| 1 | 5 | 0.61% |
| 1 | 6 | 0.61% |
| 1 | 8 | 0.61% |
| 1 | 9 | 44.85% |
| 1 | 18 | 4.24% |
| 1 | 20 | 13.33% |
| 1 | 23 | 29.09% |
| 2 | 5 | 1.21% |
| 2 | 7 | 0.61% |
| 2 | 8 | 1.21% |
| 2 | 9 | 30.30% |
| 2 | 11 | 0.61% |
| 2 | 15 | 0.61% |
| 2 | 18 | 30.91% |
| 2 | 19 | 0.61% |
| 2 | 20 | 0.61% |
| 3 | 6 | 0.61% |
| 3 | 9 | 4.24% |
| 3 | 18 | 0.61% |
| 3 | 20 | 4.24% |
| 4 | 5 | 1.21% |
| 4 | 6 | 4.24% |
| 4 | 7 | 3.03% |
| 4 | 8 | 2.42% |
| 4 | 9 | 4.24% |
| 4 | 11 | 1.21% |
| 4 | 14 | 4.85% |
| 4 | 17 | 1.82% |
| 4 | 18 | 0.61% |
| 4 | 20 | 1.21% |
| 4 | 23 | 5.45% |
| 5 | 18 | 1.21% |
| 5 | 19 | 0.61% |
| 5 | 20 | 1.21% |
| 6 | 17 | 1.82% |
| 6 | 20 | 0.61% |
| 6 | 23 | 3.03% |
| 7 | 20 | 0.61% |

TABLE 9-continued

HVR-L1, HVR-L2, and HVR-L3 2-segment combination usage

| SEQ ID NO. | SEQ ID NO. | Percent |
|---|---|---|
| 7 | 23 | 3.03% |
| 8 | 11 | 1.82% |
| 8 | 14 | 0.61% |
| 8 | 18 | 1.21% |
| 8 | 20 | 0.61% |
| 9 | 14 | 4.24% |
| 9 | 15 | 0.61% |
| 9 | 18 | 33.94% |
| 9 | 20 | 16.36% |
| 9 | 23 | 28.48% |

TABLE 10

HVR-L1, HVR-L2, and HVR-L3 3-segment combination usage

| SEQ ID NO. | SEQ ID NO. | SEQ ID NO. | Percent |
|---|---|---|---|
| 1 | 5 | 18 | 0.61% |
| 1 | 6 | 23 | 0.61% |
| 1 | 8 | 20 | 0.61% |
| 1 | 9 | 18 | 3.64% |
| 1 | 9 | 20 | 12.73% |
| 1 | 9 | 23 | 28.48% |
| 2 | 5 | 18 | 0.61% |
| 2 | 5 | 19 | 0.61% |
| 2 | 7 | 20 | 0.61% |
| 2 | 8 | 11 | 0.61% |
| 2 | 8 | 18 | 0.61% |
| 2 | 9 | 15 | 0.61% |
| 2 | 9 | 18 | 29.70% |
| 3 | 6 | 20 | 0.61% |
| 3 | 9 | 18 | 0.61% |
| 3 | 9 | 20 | 3.64% |
| 4 | 5 | 20 | 1.21% |
| 4 | 6 | 17 | 1.82% |
| 4 | 6 | 23 | 2.42% |
| 4 | 7 | 23 | 3.03% |
| 4 | 8 | 11 | 1.21% |
| 4 | 8 | 14 | 0.61% |
| 4 | 8 | 18 | 0.61% |
| 4 | 9 | 14 | 4.24% |

The novel methodology employed to identify the dynamic motif of the redefined hypervariable regions of antibodies based upon structural and sequence variability has led to the design of a limited number of VL components that can bind to the same or multiple different targets depending upon the VH segment with which the VL component is paired. The data and antibodies described herein reveals that the DL280 light chain library, either used as a whole set or a subset, is robust enough to serve as the VL component for antibody discovery.

What is claimed is:

1. A non-human animal comprising polynucleotides that encode antibody light chain variable regions ($V_L$s), wherein each of the $V_L$s comprises an HVR-L1, an HVR-L2 and an HVR-L3, and wherein at least one $V_L$ comprises an HVR-L1, an HVR-L2 and an HVR-L3 selected from the group consisting of:

(1) an HVR-L1 that comprises SEQ ID NO:1, an HVR-L2 that comprises SEQ ID NO: 5, and an HVR-L3 that comprises SEQ ID NO: 10;

(2) an HVR-L1 that comprises SEQ ID NO:1, an HVR-L2 that comprises SEQ ID NO: 5, and an HVR-L3 that comprises SEQ ID NO:11;

(3) an HVR-L1 that comprises SEQ ID NO:1, an HVR-L2 that comprises SEQ ID NO: 5, and an HVR-L3 that comprises SEQ ID NO: 12;

(4) an HVR-L1 that comprises SEQ ID NO:1, an HVR-L2 that comprises SEQ ID NO: 5, and an HVR-L3 that comprises SEQ ID NO:13;

(5) an HVR-L1 that comprises SEQ ID NO:1, an HVR-L2 that comprises SEQ ID NO: 5, and an HVR-L3 that comprises SEQ ID NO: 14;

(6) an HVR-L1 that comprises SEQ ID NO:1, an HVR-L2 that comprises SEQ ID NO: 5, and an HVR-L3 that comprises SEQ ID NO: 15;

(7) an HVR-L1 that comprises SEQ ID NO:1, an HVR-L2 that comprises SEQ ID NO: 5, and an HVR-L3 that comprises SEQ ID NO: 16;

(8) an HVR-L1 that comprises SEQ ID NO:1, an HVR-L2 that comprises SEQ ID NO: 5, and an HVR-L3 that comprises SEQ ID NO:17;

(9) an HVR-L1 that comprises SEQ ID NO:1, an HVR-L2 that comprises SEQ ID NO: 5, and an HVR-L3 that comprises SEQ ID NO:18;

(10) an HVR-L1 that comprises SEQ ID NO:1, an HVR-L2 that comprises SEQ ID NO: 5, and an HVR-L3 that comprises SEQ ID NO:19;

(11) an HVR-L1 that comprises SEQ ID NO:1, an HVR-L2 that comprises SEQ ID NO: 5, and an HVR-L3 that comprises SEQ ID NO:20;
(12) an HVR-L1 that comprises SEQ ID NO:1, an HVR-L2 that comprises SEQ ID NO: 5, and an HVR-L3 that comprises SEQ ID NO:21;
(13) an HVR-L1 that comprises SEQ ID NO:1, an HVR-L2 that comprises SEQ ID NO: 5, and an HVR-L3 that comprises SEQ ID NO:22:
(14) an HVR-L1 that comprises SEQ ID NO:1, an HVR-L2 that comprises SEQ ID NO: 5, and an HVR-L3 that comprises SEQ ID NO:23;
(15) an HVR-L1 that comprises SEQ ID NO:1, an HVR-L2 that comprises SEQ ID NO: 6, and an HVR-L3 that comprises SEQ ID NO: 10;
(16) an HVR-L1 that comprises SEQ ID NO:1, an HVR-L2 that comprises SEQ ID NO: 6, and an HVR-L3 that comprises SEQ ID NO:11;
(17) an HVR-L1 that comprises SEQ ID NO:1, an HVR-L2 that comprises SEQ ID NO: 6, and an HVR-L3 that comprises SEQ ID NO: 12;
(18) an HVR-L1 that comprises SEQ ID NO:1, an HVR-L2 that comprises SEQ ID NO: 6, and an HVR-L3 that comprises SEQ ID NO: 13;
(19) an HVR-L1 that comprises SEQ ID NO:1, an HVR-L2 that comprises SEQ ID NO: 6, and an HVR-L3 that comprises SEQ ID NO: 14;
(20) an HVR-L1 that comprises SEQ ID NO:1, an HVR-L2 that comprises SEQ ID NO: 6, and an HVR-L3 that comprises SEQ ID NO:15;
(21) an HVR-L1 that comprises SEQ ID NO:1, an HVR-L2 that comprises SEQ ID NO: 6, and an HVR-L3 that comprises SEQ ID NO:16;
(22) an HVR-L1 that comprises SEQ ID NO:1, an HVR-L2 that comprises SEQ ID NO: 6, and an HVR-L3 that comprises SEQ ID NO: 17;
(23) an HVR-L1 that comprises SEQ ID NO:1, an HVR-L2 that comprises SEQ ID NO: 6, and an HVR-L3 that comprises SEQ ID NO:18;
(24) an HVR-L1 that comprises SEQ ID NO:1, an HVR-L2 that comprises SEQ ID NO: 6, and an HVR-L3 that comprises SEQ ID NO:19;
(25) an HVR-L1 that comprises SEQ ID NO:1, an HVR-L2 that comprises SEQ ID NO: 6, and an HVR-L3 that comprises SEQ ID NO:20;
(26) an HVR-L1 that comprises SEQ ID NO:1, an HVR-L2 that comprises SEQ ID NO: 6, and an HVR-L3 that comprises SEQ ID NO:21;
(27) an HVR-L1 that comprises SEQ ID NO:1, an HVR-L2 that comprises SEQ ID NO: 6, and an HVR-L3 that comprises SEQ ID NO:22;
(28) an HVR-L1 that comprises SEQ ID NO:1, an HVR-L2 that comprises SEQ ID NO: 6, and an HVR-L3 that comprises SEQ ID NO:23;
(29) an HVR-L1 that comprises SEQ ID NO:1, an HVR-L2 that comprises SEQ ID NO: 7, and an HVR-L3 that comprises SEQ ID NO:10;
(30) an HVR-L1 that comprises SEQ ID NO:1, an HVR-L2 that comprises SEQ ID NO: 7, and an HVR-L3 that comprises SEQ ID NO:11;
(31) an HVR-L1 that comprises SEQ ID NO:1, an HVR-L2 that comprises SEQ ID NO: 7, and an HVR-L3 that comprises SEQ ID NO:12;
(32) an HVR-L1 that comprises SEQ ID NO: 1, an HVR-L2 that comprises SEQ ID NO: 7, and an HVR-L3 that comprises SEQ ID NO: 13;
(33) an HVR-L1 that comprises SEQ ID NO: 1, an HVR-L2 that comprises SEQ ID NO: 7, and an HVR-L3 that comprises SEQ ID NO:14;
(34) an HVR-L1 that comprises SEQ ID NO:1, an HVR-L2 that comprises SEQ ID NO: 7, and an HVR-L3 that comprises SEQ ID NO: 15;
(35) an HVR-L1 that comprises SEQ ID NO:1, an HVR-L2 that comprises SEQ ID NO: 7, and an HVR-L3 that comprises SEQ ID NO:16;
(36) an HVR-L1 that comprises SEQ ID NO:1, an HVR-L2 that comprises SEQ ID NO: 7, and an HVR-L3 that comprises SEQ ID NO:17;
(37) an HVR-L1 that comprises SEQ ID NO:1, an HVR-L2 that comprises SEQ ID NO: 7, and an HVR-L3 that comprises SEQ ID NO:18;
(38) an HVR-L1 that comprises SEQ ID NO:1, an HVR-L2 that comprises SEQ ID NO: 7, and an HVR-L3 that comprises SEQ ID NO:19;
(39) an HVR-L1 that comprises SEQ ID NO: 1, an HVR-L2 that comprises SEQ ID NO: 7, and an HVR-L3 that comprises SEQ ID NO:20;
(40) an HVR-L1 that comprises SEQ ID NO:1, an HVR-L2 that comprises SEQ ID NO: 7, and an HVR-L3 that comprises SEQ ID NO:21;
(41) an HVR-L1 that comprises SEQ ID NO:1, an HVR-L2 that comprises SEQ ID NO: 7, and an HVR-L3 that comprises SEQ ID NO:22;
(42) an HVR-L1 that comprises SEQ ID NO: 1, an HVR-L2 that comprises SEQ ID NO: 7, and an HVR-L3 that comprises SEQ ID NO:23;
(43) an HVR-L1 that comprises SEQ ID NO:1, an HVR-L2 that comprises SEQ ID NO: 8, and an HVR-L3 that comprises SEQ ID NO: 10;
(44) an HVR-L1 that comprises SEQ ID NO:1, an HVR-L2 that comprises SEQ ID NO: 8, and an HVR-L3 that comprises SEQ ID NO:11;
(45) an HVR-L1 that comprises SEQ ID NO:1, an HVR-L2 that comprises SEQ ID NO: 8, and an HVR-L3 that comprises SEQ ID NO: 12;
(46) an HVR-L1 that comprises SEQ ID NO:1, an HVR-L2 that comprises SEQ ID NO: 8, and an HVR-L3 that comprises SEQ ID NO: 13;
(47) an HVR-L1 that comprises SEQ ID NO:1, an HVR-L2 that comprises SEQ ID NO: 8, and an HVR-L3 that comprises SEQ ID NO: 14;
(48) an HVR-L1 that comprises SEQ ID NO:1, an HVR-L2 that comprises SEQ ID NO: 8, and an HVR-L3 that comprises SEQ ID NO:15;
(49) an HVR-L1 that comprises SEQ ID NO:1, an HVR-L2 that comprises SEQ ID NO: 8, and an HVR-L3 that comprises SEQ ID NO: 16;
(50) an HVR-L1 that comprises SEQ ID NO:1, an HVR-L2 that comprises SEQ ID NO: 8, and an HVR-L3 that comprises SEQ ID NO:17;
(51) an HVR-L1 that comprises SEQ ID NO: 1, an HVR-L2 that comprises SEQ ID NO: 8, and an HVR-L3 that comprises SEQ ID NO: 18;
(52) an HVR-L1 that comprises SEQ ID NO:1, an HVR-L2 that comprises SEQ ID NO: 8, and an HVR-L3 that comprises SEQ ID NO:19;
(53) an HVR-L1 that comprises SEQ ID NO:1, an HVR-L2 that comprises SEQ ID NO: 8, and an HVR-L3 that comprises SEQ ID NO:20;
(54) an HVR-L1 that comprises SEQ ID NO: 1, an HVR-L2 that comprises SEQ ID NO: 8, and an HVR-L3 that comprises SEQ ID NO:21;

(55) an HVR-L1 that comprises SEQ ID NO:1, an HVR-L2 that comprises SEQ ID NO: 8, and an HVR-L3 that comprises SEQ ID NO:22;
(56) an HVR-L1 that comprises SEQ ID NO:1, an HVR-L2 that comprises SEQ ID NO: 8, and an HVR-L3 that comprises SEQ ID NO:23;
(57) an HVR-L1 that comprises SEQ ID NO:1, an HVR-L2 that comprises SEQ ID NO: 9, and an HVR-L3 that comprises SEQ ID NO: 10;
(58) an HVR-L1 that comprises SEQ ID NO:1, an HVR-L2 that comprises SEQ ID NO: 9, and an HVR-L3 that comprises SEQ ID NO:11;
(59) an HVR-L1 that comprises SEQ ID NO:1, an HVR-L2 that comprises SEQ ID NO: 9, and an HVR-L3 that comprises SEQ ID NO:12;
(60) an HVR-L1 that comprises SEQ ID NO:1, an HVR-L2 that comprises SEQ ID NO: 9, and an HVR-L3 that comprises SEQ ID NO:13;
(61) an HVR-L1 that comprises SEQ ID NO:1, an HVR-L2 that comprises SEQ ID NO: 9, and an HVR-L3 that comprises SEQ ID NO: 14;
(62) an HVR-L1 that comprises SEQ ID NO:1, an HVR-L2 that comprises SEQ ID NO: 9, and an HVR-L3 that comprises SEQ ID NO:15;
(63) an HVR-L1 that comprises SEQ ID NO:1, an HVR-L2 that comprises SEQ ID NO: 9, and an HVR-L3 that comprises SEQ ID NO: 16;
(64) an HVR-L1 that comprises SEQ ID NO:1, an HVR-L2 that comprises SEQ ID NO: 9, and an HVR-L3 that comprises SEQ ID NO: 17;
(65) an HVR-L1 that comprises SEQ ID NO:1, an HVR-L2 that comprises SEQ ID NO: 9, and an HVR-L3 that comprises SEQ ID NO: 18;
(66) an HVR-L1 that comprises SEQ ID NO:1, an HVR-L2 that comprises SEQ ID NO: 9, and an HVR-L3 that comprises SEQ ID NO: 19;
(67) an HVR-L1 that comprises SEQ ID NO:1, an HVR-L2 that comprises SEQ ID NO: 9, and an HVR-L3 that comprises SEQ ID NO:20;
(68) an HVR-L1 that comprises SEQ ID NO:1, an HVR-L2 that comprises SEQ ID NO: 9, and an HVR-L3 that comprises SEQ ID NO:21;
(69) an HVR-L1 that comprises SEQ ID NO:1, an HVR-L2 that comprises SEQ ID NO: 9, and an HVR-L3 that comprises SEQ ID NO:22;
(70) an HVR-L1 that comprises SEQ ID NO:1, an HVR-L2 that comprises SEQ ID NO: 9, and an HVR-L3 that comprises SEQ ID NO:22;
(71) an HVR-L1 that comprises SEQ ID NO:2, an HVR-L2 that comprises SEQ ID NO: 5, and an HVR-L3 that comprises SEQ ID NO:10;
(72) an HVR-L1 that comprises SEQ ID NO:2, an HVR-L2 that comprises SEQ ID NO: 5, and an HVR-L3 that comprises SEQ ID NO:11;
(73) an HVR-L1 that comprises SEQ ID NO:2, an HVR-L2 that comprises SEQ ID NO: 5, and an HVR-L3 that comprises SEQ ID NO: 12;
(74) an HVR-L1 that comprises SEQ ID NO:2, an HVR-L2 that comprises SEQ ID NO: 5, and an HVR-L3 that comprises SEQ ID NO:13;
(75) an HVR-L1 that comprises SEQ ID NO:2, an HVR-L2 that comprises SEQ ID NO: 5, and an HVR-L3 that comprises SEQ ID NO: 14;
(76) an HVR-L1 that comprises SEQ ID NO:2, an HVR-L2 that comprises SEQ ID NO: 5, and an HVR-L3 that comprises SEQ ID NO: 15;
(77) an HVR-L1 that comprises SEQ ID NO:2, an HVR-L2 that comprises SEQ ID NO: 5, and an HVR-L3 that comprises SEQ ID NO:16;
(78) an HVR-L1 that comprises SEQ ID NO:2, an HVR-L2 that comprises SEQ ID NO: 5, and an HVR-L3 that comprises SEQ ID NO:17;
(79) an HVR-L1 that comprises SEQ ID NO:2, an HVR-L2 that comprises SEQ ID NO: 5, and an HVR-L3 that comprises SEQ ID NO:18;
(80) an HVR-L1 that comprises SEQ ID NO:2, an HVR-L2 that comprises SEQ ID NO: 5, and an HVR-L3 that comprises SEQ ID NO: 19;
(81) an HVR-L1 that comprises SEQ ID NO:2, an HVR-L2 that comprises SEQ ID NO: 5, and an HVR-L3 that comprises SEQ ID NO:20;
(82) an HVR-L1 that comprises SEQ ID NO:2, an HVR-L2 that comprises SEQ ID NO: 5, and an HVR-L3 that comprises SEQ ID NO:21;
(83) an HVR-L1 that comprises SEQ ID NO:2, an HVR-L2 that comprises SEQ ID NO: 5, and an HVR-L3 that comprises SEQ ID NO:22;
(84) an HVR-L1 that comprises SEQ ID NO:2, an HVR-L2 that comprises SEQ ID NO: 5, and an HVR-L3 that comprises SEQ ID NO:23;
(85) an HVR-L1 that comprises SEQ ID NO:2, an HVR-L2 that comprises SEQ ID NO: 6, and an HVR-L3 that comprises SEQ ID NO: 10;
(86) an HVR-L1 that comprises SEQ ID NO:2, an HVR-L2 that comprises SEQ ID NO: 6, and an HVR-L3 that comprises SEQ ID NO:11;
(87) an HVR-L1 that comprises SEQ ID NO:2, an HVR-L2 that comprises SEQ ID NO: 6, and an HVR-L3 that comprises SEQ ID NO:12;
(88) an HVR-L1 that comprises SEQ ID NO:2, an HVR-L2 that comprises SEQ ID NO: 6, and an HVR-L3 that comprises SEQ ID NO:13;
(89) an HVR-L1 that comprises SEQ ID NO:2, an HVR-L2 that comprises SEQ ID NO: 6, and an HVR-L3 that comprises SEQ ID NO: 14;
(90) an HVR-L1 that comprises SEQ ID NO:2, an HVR-L2 that comprises SEQ ID NO: 6, and an HVR-L3 that comprises SEQ ID NO:15;
(91) an HVR-L1 that comprises SEQ ID NO:2, an HVR-L2 that comprises SEQ ID NO: 6, and an HVR-L3 that comprises SEQ ID NO: 16;
(92) an HVR-L1 that comprises SEQ ID NO:2, an HVR-L2 that comprises SEQ ID NO: 6, and an HVR-L3 that comprises SEQ ID NO:17;
(93) an HVR-L1 that comprises SEQ ID NO:2, an HVR-L2 that comprises SEQ ID NO: 6, and an HVR-L3 that comprises SEQ ID NO:18;
(94) an HVR-L1 that comprises SEQ ID NO:2, an HVR-L2 that comprises SEQ ID NO: 6, and an HVR-L3 that comprises SEQ ID NO:19;
(95) an HVR-L1 that comprises SEQ ID NO:2, an HVR-L2 that comprises SEQ ID NO: 6, and an HVR-L3 that comprises SEQ ID NO:20;
(96) an HVR-L1 that comprises SEQ ID NO:2, an HVR-L2 that comprises SEQ ID NO: 6, and an HVR-L3 that comprises SEQ ID NO:21;
(97) an HVR-L1 that comprises SEQ ID NO:2, an HVR-L2 that comprises SEQ ID NO: 6, and an HVR-L3 that comprises SEQ ID NO:22;
(98) an HVR-L1 that comprises SEQ ID NO:2, an HVR-L2 that comprises SEQ ID NO: 6, and an HVR-L3 that comprises SEQ ID NO:23;

(99) an HVR-L1 that comprises SEQ ID NO:2, an HVR-L2 that comprises SEQ ID NO: 7, and an HVR-L3 that comprises SEQ ID NO: 10;
(100) an HVR-L1 that comprises SEQ ID NO:2, an HVR-L2 that comprises SEQ ID NO: 7, and an HVR-L3 that comprises SEQ ID NO:11;
(101) an HVR-L1 that comprises SEQ ID NO:2, an HVR-L2 that comprises SEQ ID NO: 7, and an HVR-L3 that comprises SEQ ID NO:12;
(102) an HVR-L1 that comprises SEQ ID NO:2, an HVR-L2 that comprises SEQ ID NO: 7, and an HVR-L3 that comprises SEQ ID NO: 13;
(103) an HVR-L1 that comprises SEQ ID NO:2, an HVR-L2 that comprises SEQ ID NO: 7, and an HVR-L3 that comprises SEQ ID NO: 14;
(104) an HVR-L1 that comprises SEQ ID NO:2, an HVR-L2 that comprises SEQ ID NO: 7, and an HVR-L3 that comprises SEQ ID NO:15;
(105) an HVR-L1 that comprises SEQ ID NO:2, an HVR-L2 that comprises SEQ ID NO: 7, and an HVR-L3 that comprises SEQ ID NO: 16;
(106) an HVR-L1 that comprises SEQ ID NO:2, an HVR-L2 that comprises SEQ ID NO: 7, and an HVR-L3 that comprises SEQ ID NO:17;
(107) an HVR-L1 that comprises SEQ ID NO:2, an HVR-L2 that comprises SEQ ID NO: 7, and an HVR-L3 that comprises SEQ ID NO: 18;
(108) an HVR-L1 that comprises SEQ ID NO:2, an HVR-L2 that comprises SEQ ID NO: 7, and an HVR-L3 that comprises SEQ ID NO:19;
(109) an HVR-L1 that comprises SEQ ID NO:2, an HVR-L2 that comprises SEQ ID NO: 7, and an HVR-L3 that comprises SEQ ID NO:20;
(110) an HVR-L1 that comprises SEQ ID NO:2, an HVR-L2 that comprises SEQ ID NO: 7, and an HVR-L3 that comprises SEQ ID NO:21;
(111) an HVR-L1 that comprises SEQ ID NO:2, an HVR-L2 that comprises SEQ ID NO: 7, and an HVR-L3 that comprises SEQ ID NO:22;
(112) an HVR-L1 that comprises SEQ ID NO:2, an HVR-L2 that comprises SEQ ID NO: 7, and an HVR-L3 that comprises SEQ ID NO:23;
(113) an HVR-L1 that comprises SEQ ID NO:2, an HVR-L2 that comprises SEQ ID NO: 8, and an HVR-L3 that comprises SEQ ID NO:10;
(114) an HVR-L1 that comprises SEQ ID NO:2, an HVR-L2 that comprises SEQ ID NO: 8, and an HVR-L3 that comprises SEQ ID NO:11;
(115) an HVR-L1 that comprises SEQ ID NO:2, an HVR-L2 that comprises SEQ ID NO: 8, and an HVR-L3 that comprises SEQ ID NO: 12;
(116) an HVR-L1 that comprises SEQ ID NO:2, an HVR-L2 that comprises SEQ ID NO: 8, and an HVR-L3 that comprises SEQ ID NO: 13;
(117) an HVR-L1 that comprises SEQ ID NO:2, an HVR-L2 that comprises SEQ ID NO: 8, and an HVR-L3 that comprises SEQ ID NO: 14;
(118) an HVR-L1 that comprises SEQ ID NO:2, an HVR-L2 that comprises SEQ ID NO: 8, and an HVR-L3 that comprises SEQ ID NO:15;
(119) an HVR-L1 that comprises SEQ ID NO:2, an HVR-L2 that comprises SEQ ID NO: 8, and an HVR-L3 that comprises SEQ ID NO:16;
(120) an HVR-L1 that comprises SEQ ID NO:2, an HVR-L2 that comprises SEQ ID NO: 8, and an HVR-L3 that comprises SEQ ID NO: 17;
(121) an HVR-L1 that comprises SEQ ID NO:2, an HVR-L2 that comprises SEQ ID NO: 8, and an HVR-L3 that comprises SEQ ID NO:18;
(122) an HVR-L1 that comprises SEQ ID NO:2, an HVR-L2 that comprises SEQ ID NO: 8, and an HVR-L3 that comprises SEQ ID NO:19;
(123) an HVR-L1 that comprises SEQ ID NO:2, an HVR-L2 that comprises SEQ ID NO: 8, and an HVR-L3 that comprises SEQ ID NO:20;
(124) an HVR-L1 that comprises SEQ ID NO:2, an HVR-L2 that comprises SEQ ID NO: 8, and an HVR-L3 that comprises SEQ ID NO:21;
(125) an HVR-L1 that comprises SEQ ID NO:2, an HVR-L2 that comprises SEQ ID NO: 8, and an HVR-L3 that comprises SEQ ID NO:22;
(126) an HVR-L1 that comprises SEQ ID NO:2, an HVR-L2 that comprises SEQ ID NO: 8, and an HVR-L3 that comprises SEQ ID NO:23;
(127) an HVR-L1 that comprises SEQ ID NO:2, an HVR-L2 that comprises SEQ ID NO: 9, and an HVR-L3 that comprises SEQ ID NO:10;
(128) an HVR-L1 that comprises SEQ ID NO:2, an HVR-L2 that comprises SEQ ID NO: 9, and an HVR-L3 that comprises SEQ ID NO: 11;
(129) an HVR-L1 that comprises SEQ ID NO:2, an HVR-L2 that comprises SEQ ID NO: 9, and an HVR-L3 that comprises SEQ ID NO:12;
(130) an HVR-L1 that comprises SEQ ID NO:2, an HVR-L2 that comprises SEQ ID NO: 9, and an HVR-L3 that comprises SEQ ID NO: 13;
(131) an HVR-L1 that comprises SEQ ID NO:2, an HVR-L2 that comprises SEQ ID NO: 9, and an HVR-L3 that comprises SEQ ID NO:14;
(132) an HVR-L1 that comprises SEQ ID NO:2, an HVR-L2 that comprises SEQ ID NO: 9, and an HVR-L3 that comprises SEQ ID NO: 15;
(133) an HVR-L1 that comprises SEQ ID NO:2, an HVR-L2 that comprises SEQ ID NO: 9, and an HVR-L3 that comprises SEQ ID NO: 16;
(134) an HVR-L1 that comprises SEQ ID NO:2, an HVR-L2 that comprises SEQ ID NO: 9, and an HVR-L3 that comprises SEQ ID NO:17;
(135) an HVR-L1 that comprises SEQ ID NO:2, an HVR-L2 that comprises SEQ ID NO: 9, and an HVR-L3 that comprises SEQ ID NO: 18;
(136) an HVR-L1 that comprises SEQ ID NO:2, an HVR-L2 that comprises SEQ ID NO: 9, and an HVR-L3 that comprises SEQ ID NO: 19;
(137) an HVR-L1 that comprises SEQ ID NO:2, an HVR-L2 that comprises SEQ ID NO: 9, and an HVR-L3 that comprises SEQ ID NO:20;
(138) an HVR-L1 that comprises SEQ ID NO:2, an HVR-L2 that comprises SEQ ID NO: 9, and an HVR-L3 that comprises SEQ ID NO:21;
(139) an HVR-L1 that comprises SEQ ID NO:2, an HVR-L2 that comprises SEQ ID NO: 9, and an HVR-L3 that comprises SEQ ID NO:22;
(140) an HVR-L1 that comprises SEQ ID NO:2, an HVR-L2 that comprises SEQ ID NO: 9, and an HVR-L3 that comprises SEQ ID NO:23;
(141) an HVR-L1 that comprises SEQ ID NO:3, an HVR-L2 that comprises SEQ ID NO: 5, and an HVR-L3 that comprises SEQ ID NO: 10;
(142) an HVR-L1 that comprises SEQ ID NO:3, an HVR-L2 that comprises SEQ ID NO: 5, and an HVR-L3 that comprises SEQ ID NO:11;

(143) an HVR-L1 that comprises SEQ ID NO:3, an HVR-L2 that comprises SEQ ID NO: 5, and an HVR-L3 that comprises SEQ ID NO: 12;
(144) an HVR-L1 that comprises SEQ ID NO:3, an HVR-L2 that comprises SEQ ID NO: 5, and an HVR-L3 that comprises SEQ ID NO:13;
(145) an HVR-L1 that comprises SEQ ID NO:3, an HVR-L2 that comprises SEQ ID NO: 5, and an HVR-L3 that comprises SEQ ID NO:14;
(146) an HVR-L1 that comprises SEQ ID NO:3, an HVR-L2 that comprises SEQ ID NO: 5, and an HVR-L3 that comprises SEQ ID NO:15;
(147) an HVR-L1 that comprises SEQ ID NO:3, an HVR-L2 that comprises SEQ ID NO: 5, and an HVR-L3 that comprises SEQ ID NO:16;
(148) an HVR-L1 that comprises SEQ ID NO:3, an HVR-L2 that comprises SEQ ID NO: 5, and an HVR-L3 that comprises SEQ ID NO: 17;
(149) an HVR-L1 that comprises SEQ ID NO:3, an HVR-L2 that comprises SEQ ID NO: 5, and an HVR-L3 that comprises SEQ ID NO:18;
(150) an HVR-L1 that comprises SEQ ID NO:3, an HVR-L2 that comprises SEQ ID NO: 5, and an HVR-L3 that comprises SEQ ID NO: 19;
(151) an HVR-L1 that comprises SEQ ID NO:3, an HVR-L2 that comprises SEQ ID NO: 5, and an HVR-L3 that comprises SEQ ID NO:20;
(152) an HVR-L1 that comprises SEQ ID NO:3, an HVR-L2 that comprises SEQ ID NO: 5, and an HVR-L3 that comprises SEQ ID NO:21;
(153) an HVR-L1 that comprises SEQ ID NO:3, an HVR-L2 that comprises SEQ ID NO: 5, and an HVR-L3 that comprises SEQ ID NO:22;
(154) an HVR-L1 that comprises SEQ ID NO:3, an HVR-L2 that comprises SEQ ID NO: 5, and an HVR-L3 that comprises SEQ ID NO:23;
(155) an HVR-L1 that comprises SEQ ID NO:3, an HVR-L2 that comprises SEQ ID NO: 6, and an HVR-L3 that comprises SEQ ID NO: 10;
(156) an HVR-L1 that comprises SEQ ID NO:3, an HVR-L2 that comprises SEQ ID NO: 6, and an HVR-L3 that comprises SEQ ID NO:11;
(157) an HVR-L1 that comprises SEQ ID NO:3, an HVR-L2 that comprises SEQ ID NO: 6, and an HVR-L3 that comprises SEQ ID NO: 12;
(158) an HVR-L1 that comprises SEQ ID NO:3, an HVR-L2 that comprises SEQ ID NO: 6, and an HVR-L3 that comprises SEQ ID NO: 13;
(159) an HVR-L1 that comprises SEQ ID NO:3, an HVR-L2 that comprises SEQ ID NO: 6, and an HVR-L3 that comprises SEQ ID NO:14;
(160) an HVR-L1 that comprises SEQ ID NO:3, an HVR-L2 that comprises SEQ ID NO: 6, and an HVR-L3 that comprises SEQ ID NO: 15;
(161) an HVR-L1 that comprises SEQ ID NO:3, an HVR-L2 that comprises SEQ ID NO: 6, and an HVR-L3 that comprises SEQ ID NO:16;
(162) an HVR-L1 that comprises SEQ ID NO:3, an HVR-L2 that comprises SEQ ID NO: 6, and an HVR-L3 that comprises SEQ ID NO:17;
(163) an HVR-L1 that comprises SEQ ID NO:3, an HVR-L2 that comprises SEQ ID NO: 6, and an HVR-L3 that comprises SEQ ID NO: 18;
(164) an HVR-L1 that comprises SEQ ID NO:3, an HVR-L2 that comprises SEQ ID NO: 6, and an HVR-L3 that comprises SEQ ID NO:19;
(165) an HVR-L1 that comprises SEQ ID NO:3, an HVR-L2 that comprises SEQ ID NO: 6, and an HVR-L3 that comprises SEQ ID NO:20;
(166) an HVR-L1 that comprises SEQ ID NO:3, an HVR-L2 that comprises SEQ ID NO: 6, and an HVR-L3 that comprises SEQ ID NO:21;
(167) an HVR-L1 that comprises SEQ ID NO:3, an HVR-L2 that comprises SEQ ID NO: 6, and an HVR-L3 that comprises SEQ ID NO:22;
(168) an HVR-L1 that comprises SEQ ID NO:3, an HVR-L2 that comprises SEQ ID NO: 6, and an HVR-L3 that comprises SEQ ID NO:23;
(169) an HVR-L1 that comprises SEQ ID NO:3, an HVR-L2 that comprises SEQ ID NO: 7, and an HVR-L3 that comprises SEQ ID NO:10;
(170) an HVR-L1 that comprises SEQ ID NO:3, an HVR-L2 that comprises SEQ ID NO: 7, and an HVR-L3 that comprises SEQ ID NO:11;
(171) an HVR-L1 that comprises SEQ ID NO:3, an HVR-L2 that comprises SEQ ID NO: 7, and an HVR-L3 that comprises SEQ ID NO: 12;
(172) an HVR-L1 that comprises SEQ ID NO:3, an HVR-L2 that comprises SEQ ID NO: 7, and an HVR-L3 that comprises SEQ ID NO: 13;
(173) an HVR-L1 that comprises SEQ ID NO:3, an HVR-L2 that comprises SEQ ID NO: 7, and an HVR-L3 that comprises SEQ ID NO:14;
(174) an HVR-L1 that comprises SEQ ID NO:3, an HVR-L2 that comprises SEQ ID NO: 7, and an HVR-L3 that comprises SEQ ID NO:15;
(175) an HVR-L1 that comprises SEQ ID NO:3, an HVR-L2 that comprises SEQ ID NO: 7, and an HVR-L3 that comprises SEQ ID NO: 16;
(176) an HVR-L1 that comprises SEQ ID NO:3, an HVR-L2 that comprises SEQ ID NO: 7, and an HVR-L3 that comprises SEQ ID NO:17;
(177) an HVR-L1 that comprises SEQ ID NO:3, an HVR-L2 that comprises SEQ ID NO: 7, and an HVR-L3 that comprises SEQ ID NO:18;
(178) an HVR-L1 that comprises SEQ ID NO:3, an HVR-L2 that comprises SEQ ID NO: 7, and an HVR-L3 that comprises SEQ ID NO:19;
(179) an HVR-L1 that comprises SEQ ID NO:3, an HVR-L2 that comprises SEQ ID NO: 7, and an HVR-L3 that comprises SEQ ID NO:20;
(180) an HVR-L1 that comprises SEQ ID NO:3, an HVR-L2 that comprises SEQ ID NO: 7, and an HVR-L3 that comprises SEQ ID NO:21;
(181) an HVR-L1 that comprises SEQ ID NO:3, an HVR-L2 that comprises SEQ ID NO: 7, and an HVR-L3 that comprises SEQ ID NO:22;
(182) an HVR-L1 that comprises SEQ ID NO:3, an HVR-L2 that comprises SEQ ID NO: 7, and an HVR-L3 that comprises SEQ ID NO:23;
(183) an HVR-L1 that comprises SEQ ID NO:3, an HVR-L2 that comprises SEQ ID NO: 8, and an HVR-L3 that comprises SEQ ID NO:10;
(184) an HVR-L1 that comprises SEQ ID NO:3, an HVR-L2 that comprises SEQ ID NO: 8, and an HVR-L3 that comprises SEQ ID NO:11;
(185) an HVR-L1 that comprises SEQ ID NO:3, an HVR-L2 that comprises SEQ ID NO: 8, and an HVR-L3 that comprises SEQ ID NO:12;
(186) an HVR-L1 that comprises SEQ ID NO:3, an HVR-L2 that comprises SEQ ID NO: 8, and an HVR-L3 that comprises SEQ ID NO: 13;

(187) an HVR-L1 that comprises SEQ ID NO:3, an HVR-L2 that comprises SEQ ID NO: 8, and an HVR-L3 that comprises SEQ ID NO: 14;
(188) an HVR-L1 that comprises SEQ ID NO:3, an HVR-L2 that comprises SEQ ID NO: 8, and an HVR-L3 that comprises SEQ ID NO:15;
(189) an HVR-L1 that comprises SEQ ID NO:3, an HVR-L2 that comprises SEQ ID NO: 8, and an HVR-L3 that comprises SEQ ID NO:16;
(190) an HVR-L1 that comprises SEQ ID NO:3, an HVR-L2 that comprises SEQ ID NO: 8, and an HVR-L3 that comprises SEQ ID NO:17;
(191) an HVR-L1 that comprises SEQ ID NO:3, an HVR-L2 that comprises SEQ ID NO: 8, and an HVR-L3 that comprises SEQ ID NO: 18;
(192) an HVR-L1 that comprises SEQ ID NO:3, an HVR-L2 that comprises SEQ ID NO: 8, and an HVR-L3 that comprises SEQ ID NO:19;
(193) an HVR-L1 that comprises SEQ ID NO:3, an HVR-L2 that comprises SEQ ID NO: 8, and an HVR-L3 that comprises SEQ ID NO:20;
(194) an HVR-L1 that comprises SEQ ID NO:3, an HVR-L2 that comprises SEQ ID NO: 8, and an HVR-L3 that comprises SEQ ID NO:21;
(195) an HVR-L1 that comprises SEQ ID NO:3, an HVR-L2 that comprises SEQ ID NO: 8, and an HVR-L3 that comprises SEQ ID NO:22;
(196) an HVR-L1 that comprises SEQ ID NO:3, an HVR-L2 that comprises SEQ ID NO: 8, and an HVR-L3 that comprises SEQ ID NO:23;
(197) an HVR-L1 that comprises SEQ ID NO:3, an HVR-L2 that comprises SEQ ID NO: 9, and an HVR-L3 that comprises SEQ ID NO: 10;
(198) an HVR-L1 that comprises SEQ ID NO:3, an HVR-L2 that comprises SEQ ID NO: 9, and an HVR-L3 that comprises SEQ ID NO:11;
(199) an HVR-L1 that comprises SEQ ID NO:3, an HVR-L2 that comprises SEQ ID NO: 9, and an HVR-L3 that comprises SEQ ID NO:12;
(200) an HVR-L1 that comprises SEQ ID NO:3, an HVR-L2 that comprises SEQ ID NO: 9, and an HVR-L3 that comprises SEQ ID NO: 13;
(201) an HVR-L1 that comprises SEQ ID NO:3, an HVR-L2 that comprises SEQ ID NO: 9, and an HVR-L3 that comprises SEQ ID NO: 14;
(202) an HVR-L1 that comprises SEQ ID NO:3, an HVR-L2 that comprises SEQ ID NO: 9, and an HVR-L3 that comprises SEQ ID NO:15
(203) an HVR-L1 that comprises SEQ ID NO:3, an HVR-L2 that comprises SEQ ID NO: 9, and an HVR-L3 that comprises SEQ ID NO:16;
(204) an HVR-L1 that comprises SEQ ID NO:3, an HVR-L2 that comprises SEQ ID NO: 9, and an HVR-L3 that comprises SEQ ID NO:17;
(205) an HVR-L1 that comprises SEQ ID NO:3, an HVR-L2 that comprises SEQ ID NO: 9, and an HVR-L3 that comprises SEQ ID NO:18;
(206) an HVR-L1 that comprises SEQ ID NO:3, an HVR-L2 that comprises SEQ ID NO: 9, and an HVR-L3 that comprises SEQ ID NO:19;
(207) an HVR-L1 that comprises SEQ ID NO:3, an HVR-L2 that comprises SEQ ID NO: 9, and an HVR-L3 that comprises SEQ ID NO:20;
(208) an HVR-L1 that comprises SEQ ID NO:3, an HVR-L2 that comprises SEQ ID NO: 9, and an HVR-L3 that comprises SEQ ID NO:21;
(209) an HVR-L1 that comprises SEQ ID NO:3, an HVR-L2 that comprises SEQ ID NO: 9, and an HVR-L3 that comprises SEQ ID NO:22;
(210) an HVR-L1 that comprises SEQ ID NO:3, an HVR-L2 that comprises SEQ ID NO: 9, and an HVR-L3 that comprises SEQ ID NO:23;
(211) an HVR-L1 that comprises SEQ ID NO:4, an HVR-L2 that comprises SEQ ID NO: 5, and an HVR-L3 that comprises SEQ ID NO:10;
(212) an HVR-L1 that comprises SEQ ID NO:4, an HVR-L2 that comprises SEQ ID NO: 5, and an HVR-L3 that comprises SEQ ID NO:11;
(213) an HVR-L1 that comprises SEQ ID NO:4, an HVR-L2 that comprises SEQ ID NO: 5, and an HVR-L3 that comprises SEQ ID NO: 12;
(214) an HVR-L1 that comprises SEQ ID NO:4, an HVR-L2 that comprises SEQ ID NO: 5, and an HVR-L3 that comprises SEQ ID NO:13;
(215) an HVR-L1 that comprises SEQ ID NO:4, an HVR-L2 that comprises SEQ ID NO: 5, and an HVR-L3 that comprises SEQ ID NO:14;
(216) an HVR-L1 that comprises SEQ ID NO:4, an HVR-L2 that comprises SEQ ID NO: 5, and an HVR-L3 that comprises SEQ ID NO:15;
(217) an HVR-L1 that comprises SEQ ID NO:4, an HVR-L2 that comprises SEQ ID NO: 5, and an HVR-L3 that comprises SEQ ID NO: 16;
(218) an HVR-L1 that comprises SEQ ID NO:4, an HVR-L2 that comprises SEQ ID NO: 5, and an HVR-L3 that comprises SEQ ID NO:17;
(219) an HVR-L1 that comprises SEQ ID NO:4, an HVR-L2 that comprises SEQ ID NO: 5, and an HVR-L3 that comprises SEQ ID NO: 18;
(220) an HVR-L1 that comprises SEQ ID NO:4, an HVR-L2 that comprises SEQ ID NO: 5, and an HVR-L3 that comprises SEQ ID NO:19;
(221) an HVR-L1 that comprises SEQ ID NO:4, an HVR-L2 that comprises SEQ ID NO: 5, and an HVR-L3 that comprises SEQ ID NO:20;
(222) an HVR-L1 that comprises SEQ ID NO:4, an HVR-L2 that comprises SEQ ID NO: 5, and an HVR-L3 that comprises SEQ ID NO:21;
(223) an HVR-L1 that comprises SEQ ID NO:4, an HVR-L2 that comprises SEQ ID NO: 5, and an HVR-L3 that comprises SEQ ID NO:22;
(224) an HVR-L1 that comprises SEQ ID NO:4, an HVR-L2 that comprises SEQ ID NO: 5, and an HVR-L3 that comprises SEQ ID NO:23;
(225) an HVR-L1 that comprises SEQ ID NO:4, an HVR-L2 that comprises SEQ ID NO: 6, and an HVR-L3 that comprises SEQ ID NO: 10;
(226) an HVR-L1 that comprises SEQ ID NO:4, an HVR-L2 that comprises SEQ ID NO: 6, and an HVR-L3 that comprises SEQ ID NO:11;
(227) an HVR-L1 that comprises SEQ ID NO:4, an HVR-L2 that comprises SEQ ID NO: 6, and an HVR-L3 that comprises SEQ ID NO:12;
(228) an HVR-L1 that comprises SEQ ID NO:4, an HVR-L2 that comprises SEQ ID NO: 6, and an HVR-L3 that comprises SEQ ID NO: 13;
(229) an HVR-L1 that comprises SEQ ID NO:4, an HVR-L2 that comprises SEQ ID NO: 6, and an HVR-L3 that comprises SEQ ID NO:14;
(230) an HVR-L1 that comprises SEQ ID NO:4, an HVR-L2 that comprises SEQ ID NO: 6, and an HVR-L3 that comprises SEQ ID NO:15;

(231) an HVR-L1 that comprises SEQ ID NO:4, an HVR-L2 that comprises SEQ ID NO: 6, and an HVR-L3 that comprises SEQ ID NO:16;

(232) an HVR-L1 that comprises SEQ ID NO:4, an HVR-L2 that comprises SEQ ID NO: 6, and an HVR-L3 that comprises SEQ ID NO:17;

(233) an HVR-L1 that comprises SEQ ID NO:4, an HVR-L2 that comprises SEQ ID NO: 6, and an HVR-L3 that comprises SEQ ID NO:18;

(234) an HVR-L1 that comprises SEQ ID NO:4, an HVR-L2 that comprises SEQ ID NO: 6, and an HVR-L3 that comprises SEQ ID NO: 19;

(235) an HVR-L1 that comprises SEQ ID NO:4, an HVR-L2 that comprises SEQ ID NO: 6, and an HVR-L3 that comprises SEQ ID NO:20;

(236) an HVR-L1 that comprises SEQ ID NO:4, an HVR-L2 that comprises SEQ ID NO: 6, and an HVR-L3 that comprises SEQ ID NO:21;

(237) an HVR-L1 that comprises SEQ ID NO:4, an HVR-L2 that comprises SEQ ID NO: 6, and an HVR-L3 that comprises SEQ ID NO:22;

(238) an HVR-L1 that comprises SEQ ID NO:4, an HVR-L2 that comprises SEQ ID NO: 6, and an HVR-L3 that comprises SEQ ID NO:23;

(239) an HVR-L1 that comprises SEQ ID NO:4, an HVR-L2 that comprises SEQ ID NO: 7, and an HVR-L3 that comprises SEQ ID NO:10;

(240) an HVR-L1 that comprises SEQ ID NO:4, an HVR-L2 that comprises SEQ ID NO: 7, and an HVR-L3 that comprises SEQ ID NO: 11;

(241) an HVR-L1 that comprises SEQ ID NO:4, an HVR-L2 that comprises SEQ ID NO: 7, and an HVR-L3 that comprises SEQ ID NO:12;

(242) an HVR-L1 that comprises SEQ ID NO:4, an HVR-L2 that comprises SEQ ID NO: 7, and an HVR-L3 that comprises SEQ ID NO:13;

(243) an HVR-L1 that comprises SEQ ID NO:4, an HVR-L2 that comprises SEQ ID NO: 7, and an HVR-L3 that comprises SEQ ID NO: 14;

(244) an HVR-L1 that comprises SEQ ID NO:4, an HVR-L2 that comprises SEQ ID NO: 7, and an HVR-L3 that comprises SEQ ID NO:15;

(245) an HVR-L1 that comprises SEQ ID NO:4, an HVR-L2 that comprises SEQ ID NO: 7, and an HVR-L3 that comprises SEQ ID NO: 16;

(246) an HVR-L1 that comprises SEQ ID NO:4, an HVR-L2 that comprises SEQ ID NO: 7, and an HVR-L3 that comprises SEQ ID NO:17;

(247) an HVR-L1 that comprises SEQ ID NO:4, an HVR-L2 that comprises SEQ ID NO: 7, and an HVR-L3 that comprises SEQ ID NO: 18;

(248) an HVR-L1 that comprises SEQ ID NO:4, an HVR-L2 that comprises SEQ ID NO: 7, and an HVR-L3 that comprises SEQ ID NO:19;

(249) an HVR-L1 that comprises SEQ ID NO:4, an HVR-L2 that comprises SEQ ID NO: 7, and an HVR-L3 that comprises SEQ ID NO:20;

(250) an HVR-L1 that comprises SEQ ID NO:4, an HVR-L2 that comprises SEQ ID NO: 7, and an HVR-L3 that comprises SEQ ID NO:21;

(251) an HVR-L1 that comprises SEQ ID NO:4, an HVR-L2 that comprises SEQ ID NO: 7, and an HVR-L3 that comprises SEQ ID NO:22;

(252) an HVR-L1 that comprises SEQ ID NO:4, an HVR-L2 that comprises SEQ ID NO: 7, and an HVR-L3 that comprises SEQ ID NO:23;

(253) an HVR-L1 that comprises SEQ ID NO:4, an HVR-L2 that comprises SEQ ID NO: 8, and an HVR-L3 that comprises SEQ ID NO: 10;

(254) an HVR-L1 that comprises SEQ ID NO:4, an HVR-L2 that comprises SEQ ID NO: 8, and an HVR-L3 that comprises SEQ ID NO:11;

(255) an HVR-L1 that comprises SEQ ID NO:4, an HVR-L2 that comprises SEQ ID NO: 8, and an HVR-L3 that comprises SEQ ID NO: 12;

(256) an HVR-L1 that comprises SEQ ID NO:4, an HVR-L2 that comprises SEQ ID NO: 8, and an HVR-L3 that comprises SEQ ID NO: 13;

(257) an HVR-L1 that comprises SEQ ID NO:4, an HVR-L2 that comprises SEQ ID NO: 8, and an HVR-L3 that comprises SEQ ID NO:14;

(258) an HVR-L1 that comprises SEQ ID NO:4, an HVR-L2 that comprises SEQ ID NO: 8, and an HVR-L3 that comprises SEQ ID NO:15;

(259) an HVR-L1 that comprises SEQ ID NO:4, an HVR-L2 that comprises SEQ ID NO: 8, and an HVR-L3 that comprises SEQ ID NO: 16;

(260) an HVR-L1 that comprises SEQ ID NO:4, an HVR-L2 that comprises SEQ ID NO: 8, and an HVR-L3 that comprises SEQ ID NO:17;

(261) an HVR-L1 that comprises SEQ ID NO:4, an HVR-L2 that comprises SEQ ID NO: 8, and an HVR-L3 that comprises SEQ ID NO: 18;

(262) an HVR-L1 that comprises SEQ ID NO:4, an HVR-L2 that comprises SEQ ID NO: 8, and an HVR-L3 that comprises SEQ ID NO:19;

(263) an HVR-L1 that comprises SEQ ID NO:4, an HVR-L2 that comprises SEQ ID NO: 8, and an HVR-L3 that comprises SEQ ID NO:20;

(264) an HVR-L1 that comprises SEQ ID NO:4, an HVR-L2 that comprises SEQ ID NO: 8, and an HVR-L3 that comprises SEQ ID NO:21;

(265) an HVR-L1 that comprises SEQ ID NO:4, an HVR-L2 that comprises SEQ ID NO: 8, and an HVR-L3 that comprises SEQ ID NO:22;

(266) an HVR-L1 that comprises SEQ ID NO:4, an HVR-L2 that comprises SEQ ID NO: 8, and an HVR-L3 that comprises SEQ ID NO:23;

(267) an HVR-L1 that comprises SEQ ID NO:4, an HVR-L2 that comprises SEQ ID NO: 9, and an HVR-L3 that comprises SEQ ID NO:10;

(268) an HVR-L1 that comprises SEQ ID NO:4, an HVR-L2 that comprises SEQ ID NO: 9, and an HVR-L3 that comprises SEQ ID NO:11;

(269) an HVR-L1 that comprises SEQ ID NO:4, an HVR-L2 that comprises SEQ ID NO: 9, and an HVR-L3 that comprises SEQ ID NO: 12;

(270) an HVR-L1 that comprises SEQ ID NO:4, an HVR-L2 that comprises SEQ ID NO: 9, and an HVR-L3 that comprises SEQ ID NO: 13;

(271) an HVR-L1 that comprises SEQ ID NO:4, an HVR-L2 that comprises SEQ ID NO: 9, and an HVR-L3 that comprises SEQ ID NO:14;

(272) an HVR-L1 that comprises SEQ ID NO:4, an HVR-L2 that comprises SEQ ID NO: 9, and an HVR-L3 that comprises SEQ ID NO:15;

(273) an HVR-L1 that comprises SEQ ID NO:4, an HVR-L2 that comprises SEQ ID NO: 9, and an HVR-L3 that comprises SEQ ID NO: 16;

(274) an HVR-L1 that comprises SEQ ID NO:4, an HVR-L2 that comprises SEQ ID NO: 9, and an HVR-L3 that comprises SEQ ID NO:17;

(275) an HVR-L1 that comprises SEQ ID NO:4, an HVR-L2 that comprises SEQ ID NO: 9, and an HVR-L3 that comprises SEQ ID NO: 18;

(276) an HVR-L1 that comprises SEQ ID NO:4, an HVR-L2 that comprises SEQ ID NO: 9, and an HVR-L3 that comprises SEQ ID NO:19;

(277) an HVR-L1 that comprises SEQ ID NO:4, an HVR-L2 that comprises SEQ ID NO: 9, and an HVR-L3 that comprises SEQ ID NO:20;

(278) an HVR-L1 that comprises SEQ ID NO:4, an HVR-L2 that comprises SEQ ID NO: 9, and an HVR-L3 that comprises SEQ ID NO:21;

(279) an HVR-L1 that comprises SEQ ID NO:4, an HVR-L2 that comprises SEQ ID NO: 9, and an HVR-L3 that comprises SEQ ID NO:22; and (280) an HVR-L1 that comprises SEQ ID NO:4, an HVR-L2 that comprises SEQ ID NO: 9, and an HVR-L3 that comprises SEQ ID NO:23.

2. The non-human animal of claim 1, wherein at least two, at least three, at least four, at least five, or at least ten of the VLS each comprises a unique combination of HVR-L1, HVR-L2, and HVR-L3 sequences set forth in claim 1(1)-(280).

3. The non-human animal of claim 1, wherein each of the VLS comprises a unique combination of HVR-L1, HVR-L2, and HVR-L3 sequences set forth in claim 1(1)-(280).

4. The non-human animal of claim 1, wherein the $V_L$s comprise about 280 or fewer unique combinations of HVR-L1, HVR-L2, and HVR-L3 sequences.

5. The non-human animal of claim 1, wherein the at the least one $V_L$ comprises a FW-L1 comprising the amino acid sequence of SEQ ID NO:24, a FW-L2 comprising the amino acid sequence of SEQ ID NO:25, a FW-L3 comprising the amino acid sequence of SEQ ID NO:26, and a FW-L4 comprising the amino acid sequence of SEQ ID NO:27.

6. The non-human animal of claim 1, wherein the at the least one $V_L$ comprises a sequence selected from the group consisting of SEQ ID NOS: 28-50.

7. The non-human animal of claim 1, wherein the polynucleotides encode full-length antibody light chains.

8. The non-human animal of claim 1, further comprising polynucleotides that encode antibody heavy chain variable regions ($V_H$s).

9. The non-human animal of claim 8, wherein the polynucleotides that encode the $V_L$s and the polynucleotides that encode the $V_H$s together encode a plurality of unique antibodies, wherein the $V_L$ of each antibody of the plurality comprises an identical sequence.

10. The non-human animal of claim 1, wherein the polynucleotides are synthetic polynucleotides.

11. The non-human animal of claim 1, wherein at least one of the HVR-L1, HVR-L2, and HVR-L3 of the at least one $V_L$ adopts multiple conformations, as assayed by structural determination and/or computational modeling.

12. The non-human animal of claim 5, wherein each of the $V_L$s comprise a FW-L1 comprising the amino acid sequence of SEQ ID NO:24, a FW-L2 comprising the amino acid sequence of SEQ ID NO:25, a FW-L3 comprising the amino acid sequence of SEQ ID NO:26, and a FW-L4 comprising the amino acid sequence of SEQ ID NO:27.

13. The non-human animal of claim 1, wherein the non-human animal is a mammal.

* * * * *

SEQUENCE LISTING

```
Sequence total quantity: 66
SEQ ID NO: 1            moltype = AA  length = 11
FEATURE                 Location/Qualifiers
REGION                  1..11
                        note = Designed HVR-L1 sequence 1
source                  1..11
                        mol_type = protein
                        organism = synthetic construct
SEQUENCE: 1
RASQGISSYL A                                                      11
```

```
SEQ ID NO: 2            moltype = AA  length = 11
FEATURE                 Location/Qualifiers
REGION                  1..11
                        note = Designed HVR-L1 sequence 2
source                  1..11
                        mol_type = protein
                        organism = synthetic construct
SEQUENCE: 2
RASQSVSSYL A                                                 11

SEQ ID NO: 3            moltype = AA  length = 11
FEATURE                 Location/Qualifiers
REGION                  1..11
                        note = Designed HVR-L1 sequence 3
source                  1..11
                        mol_type = protein
                        organism = synthetic construct
SEQUENCE: 3
RASQGVSSYL A                                                 11

SEQ ID NO: 4            moltype = AA  length = 11
FEATURE                 Location/Qualifiers
REGION                  1..11
                        note = Designed HVR-L1 sequence 4
source                  1..11
                        mol_type = protein
                        organism = synthetic construct
SEQUENCE: 4
RASQSISSYL N                                                 11

SEQ ID NO: 5            moltype = AA  length = 9
FEATURE                 Location/Qualifiers
REGION                  1..9
                        note = Designed HVR-L2 sequence 1
source                  1..9
                        mol_type = protein
                        organism = synthetic construct
SEQUENCE: 5
AASSLQSGV                                                    9

SEQ ID NO: 6            moltype = AA  length = 9
FEATURE                 Location/Qualifiers
REGION                  1..9
                        note = Designed HVR-L2 sequence 2
source                  1..9
                        mol_type = protein
                        organism = synthetic construct
SEQUENCE: 6
DASSLESGV                                                    9

SEQ ID NO: 7            moltype = AA  length = 9
FEATURE                 Location/Qualifiers
REGION                  1..9
                        note = Designed HVR-L2 sequence 3
source                  1..9
                        mol_type = protein
                        organism = synthetic construct
SEQUENCE: 7
AASTLQSGV                                                    9

SEQ ID NO: 8            moltype = AA  length = 9
FEATURE                 Location/Qualifiers
REGION                  1..9
                        note = Designed HVR-L2 sequence 4
source                  1..9
                        mol_type = protein
                        organism = synthetic construct
SEQUENCE: 8
DASNRATGI                                                    9

SEQ ID NO: 9            moltype = AA  length = 9
FEATURE                 Location/Qualifiers
REGION                  1..9
                        note = Designed HVR-L2 sequence 5
source                  1..9
                        mol_type = protein
                        organism = synthetic construct
SEQUENCE: 9
```

```
DASNLETGV                                                   9

SEQ ID NO: 10           moltype = AA  length = 11
FEATURE                 Location/Qualifiers
REGION                  1..11
                        note = Designed HVR-L3 sequence 1
source                  1..11
                        mol_type = protein
                        organism = synthetic construct
SEQUENCE: 10
HCQHYAGYSA T                                                11

SEQ ID NO: 11           moltype = AA  length = 11
FEATURE                 Location/Qualifiers
REGION                  1..11
                        note = Designed HVR-L3 sequence 2
source                  1..11
                        mol_type = protein
                        organism = synthetic construct
SEQUENCE: 11
YCQQSYSTPP T                                                11

SEQ ID NO: 12           moltype = AA  length = 11
FEATURE                 Location/Qualifiers
REGION                  1..11
                        note = Designed HVR-L3 sequence 3
source                  1..11
                        mol_type = protein
                        organism = synthetic construct
SEQUENCE: 12
YCQQSYSTPR T                                                11

SEQ ID NO: 13           moltype = AA  length = 11
FEATURE                 Location/Qualifiers
REGION                  1..11
                        note = Designed HVR-L3 sequence 4
source                  1..11
                        mol_type = protein
                        organism = synthetic construct
SEQUENCE: 13
YCQQWSSHPQ T                                                11

SEQ ID NO: 14           moltype = AA  length = 11
FEATURE                 Location/Qualifiers
REGION                  1..11
                        note = Designed HVR-L3 sequence 5
source                  1..11
                        mol_type = protein
                        organism = synthetic construct
SEQUENCE: 14
YCQHHYGTPL T                                                11

SEQ ID NO: 15           moltype = AA  length = 11
FEATURE                 Location/Qualifiers
REGION                  1..11
                        note = Designed HVR-L3 sequence 6
source                  1..11
                        mol_type = protein
                        organism = synthetic construct
SEQUENCE: 15
YCQQSYSTSH T                                                11

SEQ ID NO: 16           moltype = AA  length = 11
FEATURE                 Location/Qualifiers
REGION                  1..11
                        note = Designed HVR-L3 sequence 7
source                  1..11
                        mol_type = protein
                        organism = synthetic construct
SEQUENCE: 16
YCQQSYSTPN T                                                11

SEQ ID NO: 17           moltype = AA  length = 11
FEATURE                 Location/Qualifiers
REGION                  1..11
                        note = Designed HVR-L3 sequence 8
source                  1..11
                        mol_type = protein
                        organism = synthetic construct
```

```
SEQUENCE: 17
YCQQWSSSPL T                                                    11

SEQ ID NO: 18           moltype = AA  length = 11
FEATURE                 Location/Qualifiers
REGION                  1..11
                        note = Designed HVR-L3 sequence 9
source                  1..11
                        mol_type = protein
                        organism = synthetic construct
SEQUENCE: 18
YCQQSYSTPL T                                                    11

SEQ ID NO: 19           moltype = AA  length = 11
FEATURE                 Location/Qualifiers
REGION                  1..11
                        note = Designed HVR-L3 sequence 10
source                  1..11
                        mol_type = protein
                        organism = synthetic construct
SEQUENCE: 19
YCQQYGSSPL T                                                    11

SEQ ID NO: 20           moltype = AA  length = 11
FEATURE                 Location/Qualifiers
REGION                  1..11
                        note = Designed HVR-L3 sequence 11
source                  1..11
                        mol_type = protein
                        organism = synthetic construct
SEQUENCE: 20
YCQQYYTTPL T                                                    11

SEQ ID NO: 21           moltype = AA  length = 11
FEATURE                 Location/Qualifiers
REGION                  1..11
                        note = Designed HVR-L3 sequence 12
source                  1..11
                        mol_type = protein
                        organism = synthetic construct
SEQUENCE: 21
YCKQAYIPPL T                                                    11

SEQ ID NO: 22           moltype = AA  length = 11
FEATURE                 Location/Qualifiers
REGION                  1..11
                        note = Designed HVR-L3 sequence 13
source                  1..11
                        mol_type = protein
                        organism = synthetic construct
SEQUENCE: 22
YCFQGSHVPR T                                                    11

SEQ ID NO: 23           moltype = AA  length = 11
FEATURE                 Location/Qualifiers
REGION                  1..11
                        note = Designed HVR-L3 sequence 14
source                  1..11
                        mol_type = protein
                        organism = synthetic construct
SEQUENCE: 23
YCQQYYSTPL T                                                    11

SEQ ID NO: 24           moltype = AA  length = 23
FEATURE                 Location/Qualifiers
REGION                  1..23
                        note = Framework FW-L1 sequence
source                  1..23
                        mol_type = protein
                        organism = synthetic construct
SEQUENCE: 24
DIQLTQSPSS LSASVGDRVT ITC                                       23

SEQ ID NO: 25           moltype = AA  length = 15
FEATURE                 Location/Qualifiers
REGION                  1..15
                        note = Framework FW-L2 sequence
source                  1..15
                        mol_type = protein
```

```
                        organism = synthetic construct
SEQUENCE: 25
WYQQKPGKAP KLLIY                                                     15

SEQ ID NO: 26           moltype = AA  length = 28
FEATURE                 Location/Qualifiers
REGION                  1..28
                        note = Framework FW-L3 sequence
source                  1..28
                        mol_type = protein
                        organism = synthetic construct
SEQUENCE: 26
PSRFSGSGSG TDFTLTISSL QPEDFATY                                       28

SEQ ID NO: 27           moltype = AA  length = 11
FEATURE                 Location/Qualifiers
REGION                  1..11
                        note = Framework FW-L4 sequence
source                  1..11
                        mol_type = protein
                        organism = synthetic construct
SEQUENCE: 27
FGQGTKVEIK R                                                         11

SEQ ID NO: 28           moltype = AA  length = 108
FEATURE                 Location/Qualifiers
REGION                  1..108
                        note = Light chain variable region sequence 1
source                  1..108
                        mol_type = protein
                        organism = synthetic construct
SEQUENCE: 28
DIQLTQSPSS LSASVGDRVT ITCRASQSVS SYLAWYQQKP GKAPKLLIYD ASNLETGVPS  60
RFSGSGSGTD FTLTISSLQP EDFATYYCQQ SYSTPLTFGQ GTKVEIKR               108

SEQ ID NO: 29           moltype = AA  length = 108
FEATURE                 Location/Qualifiers
REGION                  1..108
                        note = Light chain variable region sequence 2
source                  1..108
                        mol_type = protein
                        organism = synthetic construct
SEQUENCE: 29
DIQLTQSPSS LSASVGDRVT ITCRASQGIS SYLAWYQQKP GKAPKLLIYD ASNLETGVPS  60
RFSGSGSGTD FTLTISSLQP EDFATYYCQQ SYSTPLTFGQ GTKVEIKR               108

SEQ ID NO: 30           moltype = AA  length = 108
FEATURE                 Location/Qualifiers
REGION                  1..108
                        note = Light chain variable region sequence 3
source                  1..108
                        mol_type = protein
                        organism = synthetic construct
SEQUENCE: 30
DIQLTQSPSS LSASVGDRVT ITCRASQSIS SYLNWYQQKP GKAPKLLIYD ASNLETGVPS  60
RFSGSGSGTD FTLTISSLQP EDFATYYCQQ SYSTPLTFGQ GTKVEIKR               108

SEQ ID NO: 31           moltype = AA  length = 108
FEATURE                 Location/Qualifiers
REGION                  1..108
                        note = Light chain variable region sequence 4
source                  1..108
                        mol_type = protein
                        organism = synthetic construct
SEQUENCE: 31
DIQLTQSPSS LSASVGDRVT ITCRASQGVS SYLAWYQQKP GKAPKLLIYD ASNLETGVPS  60
RFSGSGSGTD FTLTISSLQP EDFATYYCQQ SYSTPLTFGQ GTKVEIKR               108

SEQ ID NO: 32           moltype = AA  length = 108
FEATURE                 Location/Qualifiers
REGION                  1..108
                        note = Light chain variable region sequence 5
source                  1..108
                        mol_type = protein
                        organism = synthetic construct
SEQUENCE: 32
DIQLTQSPSS LSASVGDRVT ITCRASQGIS SYLAWYQQKP GKAPKLLIYD ASNLETGVPS  60
RFSGSGSGTD FTLTISSLQP EDFATYYCQQ YYSTPLTFGQ GTKVEIKR               108
```

```
SEQ ID NO: 33          moltype = AA  length = 108
FEATURE                Location/Qualifiers
REGION                 1..108
                       note = Light chain variable region sequence 6
source                 1..108
                       mol_type = protein
                       organism = synthetic construct
SEQUENCE: 33
DIQLTQSPSS LSASVGDRVT ITCRASQGIS SYLAWYQQKP GKAPKLLIYD ASSLESGVPS  60
RFSGSGSGTD FTLTISSLQP EDFATYYCQQ YYSTPLTFGQ GTKVEIKR              108

SEQ ID NO: 34          moltype = AA  length = 108
FEATURE                Location/Qualifiers
REGION                 1..108
                       note = Light chain variable region sequence 7
source                 1..108
                       mol_type = protein
                       organism = synthetic construct
SEQUENCE: 34
DIQLTQSPSS LSASVGDRVT ITCRASQGIS SYLAWYQQKP GKAPKLLIYD ASNLETGVPS  60
RFSGSGSGTD FTLTISSLQP EDFATYYCQQ YYTTPLTFGQ GTKVEIKR              108

SEQ ID NO: 35          moltype = AA  length = 108
FEATURE                Location/Qualifiers
REGION                 1..108
                       note = Light chain variable region sequence 8
source                 1..108
                       mol_type = protein
                       organism = synthetic construct
SEQUENCE: 35
DIQLTQSPSS LSASVGDRVT ITCRASQGVS SYLAWYQQKP GKAPKLLIYD ASNLETGVPS  60
RFSGSGSGTD FTLTISSLQP EDFATYYCQQ YYTTPLTFGQ GTKVEIKR              108

SEQ ID NO: 36          moltype = AA  length = 108
FEATURE                Location/Qualifiers
REGION                 1..108
                       note = Light chain variable region sequence 9
source                 1..108
                       mol_type = protein
                       organism = synthetic construct
SEQUENCE: 36
DIQLTQSPSS LSASVGDRVT ITCRASQSIS SYLNWYQQKP GKAPKLLIYD ASNLETGVPS  60
RFSGSGSGTD FTLTISSLQP EDFATYYCQH HYGTPLTFGQ GTKVEIKR              108

SEQ ID NO: 37          moltype = AA  length = 108
FEATURE                Location/Qualifiers
REGION                 1..108
                       note = Light chain variable region sequence 10
source                 1..108
                       mol_type = protein
                       organism = synthetic construct
SEQUENCE: 37
DIQLTQSPSS LSASVGDRVT ITCRASQSIS SYLNWYQQKP GKAPKLLIYD ASNRATGIPS  60
RFSGSGSGTD FTLTISSLQP EDFATYYCQH HYGTPLTFGQ GTKVEIKR              108

SEQ ID NO: 38          moltype = AA  length = 108
FEATURE                Location/Qualifiers
REGION                 1..108
                       note = Light chain variable region sequence 11
source                 1..108
                       mol_type = protein
                       organism = synthetic construct
SEQUENCE: 38
DIQLTQSPSS LSASVGDRVT ITCRASQSIS SYLNWYQQKP GKAPKLLIYA ASTLQSGVPS  60
RFSGSGSGTD FTLTISSLQP EDFATYYCQQ YYSTPLTFGQ GTKVEIKR              108

SEQ ID NO: 39          moltype = AA  length = 108
FEATURE                Location/Qualifiers
REGION                 1..108
                       note = Light chain variable region sequence 12
source                 1..108
                       mol_type = protein
                       organism = synthetic construct
SEQUENCE: 39
DIQLTQSPSS LSASVGDRVT ITCRASQSIS SYLNWYQQKP GKAPKLLIYD ASSLESGVPS  60
RFSGSGSGTD FTLTISSLQP EDFATYYCQQ YYSTPLTFGQ GTKVEIKR              108

SEQ ID NO: 40          moltype = AA  length = 108
FEATURE                Location/Qualifiers
```

```
REGION                 1..108
                       note = Light chain variable region sequence 13
source                 1..108
                       mol_type = protein
                       organism = synthetic construct
SEQUENCE: 40
DIQLTQSPSS LSASVGDRVT ITCRASQSVS SYLAWYQQKP GKAPKLLIYD ASNRATGIPS  60
RFSGSGSGTD FTLTISSLQP EDFATYYCQQ YYTTPLTFGQ GTKVEIKR              108

SEQ ID NO: 41          moltype = AA  length = 108
FEATURE                Location/Qualifiers
REGION                 1..108
                       note = Light chain variable region sequence 14
source                 1..108
                       mol_type = protein
                       organism = synthetic construct
SEQUENCE: 41
DIQLTQSPSS LSASVGDRVT ITCRASQGVS SYLAWYQQKP GKAPKLLIYD ASNRATGIPS  60
RFSGSGSGTD FTLTISSLQP EDFATYYCQQ YYTTPLTFGQ GTKVEIKR              108

SEQ ID NO: 42          moltype = AA  length = 108
FEATURE                Location/Qualifiers
REGION                 1..108
                       note = Light chain variable region sequence 15
source                 1..108
                       mol_type = protein
                       organism = synthetic construct
SEQUENCE: 42
DIQLTQSPSS LSASVGDRVT ITCRASQSVS SYLAWYQQKP GKAPKLLIYA ASTLQSGVPS  60
RFSGSGSGTD FTLTISSLQP EDFATYYCQQ YYTTPLTFGQ GTKVEIKR              108

SEQ ID NO: 43          moltype = AA  length = 108
FEATURE                Location/Qualifiers
REGION                 1..108
                       note = Light chain variable region sequence 16
source                 1..108
                       mol_type = protein
                       organism = synthetic construct
SEQUENCE: 43
DIQLTQSPSS LSASVGDRVT ITCRASQSIS SYLNWYQQKP GKAPKLLIYA ASSLQSGVPS  60
RFSGSGSGTD FTLTISSLQP EDFATYYCQQ YYTTPLTFGQ GTKVEIKR              108

SEQ ID NO: 44          moltype = AA  length = 108
FEATURE                Location/Qualifiers
REGION                 1..108
                       note = Light chain variable region sequence 17
source                 1..108
                       mol_type = protein
                       organism = synthetic construct
SEQUENCE: 44
DIQLTQSPSS LSASVGDRVT ITCRASQSVS SYLAWYQQKP GKAPKLLIYA ASSLQSGVPS  60
RFSGSGSGTD FTLTISSLQP EDFATYYCQQ SYSTPLTFGQ GTKVEIKR              108

SEQ ID NO: 45          moltype = AA  length = 108
FEATURE                Location/Qualifiers
REGION                 1..108
                       note = Light chain variable region sequence 18
source                 1..108
                       mol_type = protein
                       organism = synthetic construct
SEQUENCE: 45
DIQLTQSPSS LSASVGDRVT ITCRASQGIS SYLAWYQQKP GKAPKLLIYA ASSLQSGVPS  60
RFSGSGSGTD FTLTISSLQP EDFATYYCQQ SYSTPLTFGQ GTKVEIKR              108

SEQ ID NO: 46          moltype = AA  length = 108
FEATURE                Location/Qualifiers
REGION                 1..108
                       note = Light chain variable region sequence 19
source                 1..108
                       mol_type = protein
                       organism = synthetic construct
SEQUENCE: 46
DIQLTQSPSS LSASVGDRVT ITCRASQSIS SYLNWYQQKP GKAPKLLIYD ASNRATGIPS  60
RFSGSGSGTD FTLTISSLQP EDFATYYCQQ SYSTPLTFGQ GTKVEIKR              108

SEQ ID NO: 47          moltype = AA  length = 108
FEATURE                Location/Qualifiers
REGION                 1..108
                       note = Light chain variable region sequence 20
```

```
source                  1..108
                        mol_type = protein
                        organism = synthetic construct
SEQUENCE: 47
DIQLTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPLTFGQ GTKVEIKR              108

SEQ ID NO: 48           moltype = AA  length = 108
FEATURE                 Location/Qualifiers
REGION                  1..108
                        note = Light chain variable region sequence 21
source                  1..108
                        mol_type = protein
                        organism = synthetic construct
SEQUENCE: 48
DIQLTQSPSS LSASVGDRVT ITCRASQSVS SYLAWYQQKP GKAPKLLIYA ASSLQSGVPS  60
RFSGSGSGTD FTLTISSLQP EDFATYYCQQ SYSTPPTFGQ GTKVEIKR              108

SEQ ID NO: 49           moltype = AA  length = 108
FEATURE                 Location/Qualifiers
REGION                  1..108
                        note = Light chain variable region sequence 22
source                  1..108
                        mol_type = protein
                        organism = synthetic construct
SEQUENCE: 49
DIQLTQSPSS LSASVGDRVT ITCRASQSIS SYLNWYQQKP GKAPKLLIYD ASSLESGVPS  60
RFSGSGSGTD FTLTISSLQP EDFATYYCQQ WSSSPLTFGQ GTKVEIKR              108

SEQ ID NO: 50           moltype = AA  length = 108
FEATURE                 Location/Qualifiers
REGION                  1..108
                        note = Light chain variable region sequence 23
source                  1..108
                        mol_type = protein
                        organism = synthetic construct
SEQUENCE: 50
DIQLTQSPSS LSASVGDRVT ITCRASQSIS SYLNWYQQKP GKAPKLLIYD ASNRATGIPS  60
RFSGSGSGTD FTLTISSLQP EDFATYYCQQ SYSTPPTFGQ GTKVEIKR              108

SEQ ID NO: 51           moltype = AA  length = 120
FEATURE                 Location/Qualifiers
REGION                  1..120
                        note = Hit ID 3757 - VH
source                  1..120
                        mol_type = protein
                        organism = synthetic construct
SEQUENCE: 51
EVQLVESGGG LVQPGGSLRL SCAASGFTFT DYGIHWVRQA PGKGLEWIGW ISPSGGGTKY  60
AQKFQGRVTI SRDNSKNTLY LQLNSLRAED TAVYYCARHS YYGVGDFDYW GQGTLVTVSS  120

SEQ ID NO: 52           moltype = AA  length = 121
FEATURE                 Location/Qualifiers
REGION                  1..121
                        note = Hit ID 5905 - VH
source                  1..121
                        mol_type = protein
                        organism = synthetic construct
SEQUENCE: 52
EVQLVESGGG LVQPGGSLRL SCAASGFSLS TGGVGVGWIR QAPGKGLEWV SSISGYGGST  60
YYADSVKGRF TISRDNSKNT LYLQLNSLRA EDTAVYYCAR GYYSTRDFDV WGQGTLVTVS  120
S                                                                  121

SEQ ID NO: 53           moltype = AA  length = 118
FEATURE                 Location/Qualifiers
REGION                  1..118
                        note = Hit ID 7035 - VH
source                  1..118
                        mol_type = protein
                        organism = synthetic construct
SEQUENCE: 53
EVQLVESGGG LVQPGGSLRL SCAASGFTFS NYWIHWVRQA PGKGLEWIGW ISPSGGGTNY  60
AQKFQGRVTI SRDNSKNTLY LQLNSLRAED TAVYYCARDP TAGGFDVWGQ GTLVTVSS    118

SEQ ID NO: 54           moltype = AA  length = 121
FEATURE                 Location/Qualifiers
REGION                  1..121
                        note = Hit ID 4218 - VH
source                  1..121
```

```
                        mol_type = protein
                        organism = synthetic construct
SEQUENCE: 54
EVQLVESGGG LVQPGGSLRL SCAASGYSIS SGYYWDWIRQ APGKGLEWVS SISGDGDTTY  60
YADSVKGRFT ISRDNSKNTL YLQLNSLRAE DTAVYYCARE DYSYGYAFDY WGQGTLVTVS  120
S                                                                  121

SEQ ID NO: 55           moltype = AA  length = 118
FEATURE                 Location/Qualifiers
REGION                  1..118
                        note = Hit ID 5114 - VH
source                  1..118
                        mol_type = protein
                        organism = synthetic construct
SEQUENCE: 55
EVQLVESGGG LVQPGGSLRL SCAASGYSIS SGYYWDWIRQ APGKGLEWIG WISPSSGSTN  60
YAQKFQGRVT ISRDNSKNTL YLQLNSLRAE DTAVYYCARW VSGYFDYWGQ GTLVTVSS    118

SEQ ID NO: 56           moltype = AA  length = 118
FEATURE                 Location/Qualifiers
REGION                  1..118
                        note = Hit ID 5145 - VH
source                  1..118
                        mol_type = protein
                        organism = synthetic construct
SEQUENCE: 56
EVQLVESGGG LVQPGGSLRL SCAASGFTFT SYWIHWVRQA PGKGLEWIGW INPNFGSTKY  60
AQKFQGRVTI SRDNSKNTLY LQLNSLRAED TAVYYCARDI TAGGLDVWGQ GTLVTVSS    118

SEQ ID NO: 57           moltype = AA  length = 124
FEATURE                 Location/Qualifiers
REGION                  1..124
                        note = Hit ID 7077 - VH
source                  1..124
                        mol_type = protein
                        organism = synthetic construct
SEQUENCE: 57
EVQLVESGGG LVQPGGSLRL SCAASGFSLS TGGVGVAWIR QAPGKGLEWV SYISGSGDTT  60
YYADSVKGRF TISRDNSKNT LYLQLNSLRA EDTAVYYCAR EGSDTVVGDW FAYWGQGTLV  120
TVSS                                                               124

SEQ ID NO: 58           moltype = AA  length = 118
FEATURE                 Location/Qualifiers
REGION                  1..118
                        note = Hit ID 5930 - VH
source                  1..118
                        mol_type = protein
                        organism = synthetic construct
SEQUENCE: 58
EFQLVESGGG LVQPGGSLRL SCAASGYSIT SGHHWDWIRQ APGKGLEWIG WINPNRGGTN  60
YAQKFQGRVT ISRDNSKNTL YLQLNSLRAE DTAVYYCARD YYGDFDYWGQ GTLVTVSS    118

SEQ ID NO: 59           moltype = AA  length = 119
FEATURE                 Location/Qualifiers
REGION                  1..119
                        note = Hit ID 6008 - VH
source                  1..119
                        mol_type = protein
                        organism = synthetic construct
SEQUENCE: 59
EVQLVESGGG LVQPGGSLRL SCAASGFTFS SYGIHWVRQA PGKGLEWIGI ISPSGGGTKY  60
AQKFQGRVTI SRDNSKNTLY LQLNSLRAED TAVYYCARSN VYYYGFDVWG QGTLVTVSS   119

SEQ ID NO: 60           moltype = AA  length = 108
FEATURE                 Location/Qualifiers
REGION                  1..108
                        note = VL in FIG. 1B
source                  1..108
                        mol_type = protein
                        organism = synthetic construct
SEQUENCE: 60
DIQLTQSPSS LSASVGDRVT ITCRASQSVS SYLAWYQQKP GKAPKLLIYD ASNLETGVPS  60
RFSGSGSGTD FTLTISSLQP EDFATYYCQQ SYSTSHTFGQ GTKVEIKR               108

SEQ ID NO: 61           moltype = DNA  length = 23
FEATURE                 Location/Qualifiers
misc_feature            1..23
                        note = F_1999
source                  1..23
```

-continued

```
                        mol_type = other DNA
                        organism = synthetic construct
SEQUENCE: 61
cgtttgtcct gtgcagcttc cgg                                         23

SEQ ID NO: 62           moltype = DNA  length = 25
FEATURE                 Location/Qualifiers
misc_feature            1..25
                        note = R_1999
source                  1..25
                        mol_type = other DNA
                        organism = synthetic construct
SEQUENCE: 62
cgaggccctt acccggggcc tgacg                                       25

SEQ ID NO: 63           moltype = DNA  length = 21
FEATURE                 Location/Qualifiers
misc_feature            1..21
                        note = F_2003
source                  1..21
                        mol_type = other DNA
                        organism = synthetic construct
SEQUENCE: 63
ccgggtaagg gcctcgagtg g                                           21

SEQ ID NO: 64           moltype = DNA  length = 33
FEATURE                 Location/Qualifiers
misc_feature            1..33
                        note = R_2003
source                  1..33
                        mol_type = other DNA
                        organism = synthetic construct
SEQUENCE: 64
gagcacgtcc gttcgaattg tcgcgactta tag                              33

SEQ ID NO: 65           moltype = DNA  length = 45
FEATURE                 Location/Qualifiers
misc_feature            1..45
                        note = S1089
source                  1..45
                        mol_type = other DNA
                        organism = synthetic construct
SEQUENCE: 65
acaactgaac agcttaagag ctgaggacac tgccgtctat tattg                 45

SEQ ID NO: 66           moltype = DNA  length = 32
FEATURE                 Location/Qualifiers
misc_feature            1..32
                        note = S1090
source                  1..32
                        mol_type = other DNA
                        organism = synthetic construct
SEQUENCE: 66
gaggagacgg tgactagtgt tccttgaccc ca                               32
```